(12) United States Patent
Johnson et al.

(10) Patent No.: US 6,303,610 B1
(45) Date of Patent: Oct. 16, 2001

(54) METHOD OF TREATING GOUT WITH CERTAIN INDOLE COMPOUNDS

(75) Inventors: Douglas W Johnson, Zionsville; John M Morin, Jr., Brownsburg; Jason S Sawyer, Indianapolis, all of IN (US); Robert T Shuman, Sedona, AZ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/462,346

(22) PCT Filed: Jul. 8, 1998

(86) PCT No.: PCT/US98/14262

§ 371 Date: Mar. 6, 2000

§ 102(e) Date: Mar. 6, 2000

(87) PCT Pub. No.: WO99/02163

PCT Pub. Date: Jan. 21, 1999

Related U.S. Application Data

(60) Provisional application No. 60/052,117, filed on Jul. 10, 1997.

(51) Int. Cl.$^7$ .................. A61K 31/495; A61K 31/50; A61K 31/445; A61K 31/405

(52) U.S. Cl. .................. 514/254.01; 514/316; 514/323; 514/415

(58) Field of Search ............................. 514/415, 254.01, 514/316, 323

(56) References Cited

U.S. PATENT DOCUMENTS

| 5,670,499 | 9/1997 | Cho et al. | 514/231.5 |
| 5,684,033 | 11/1997 | Cho et al. | 514/415 |

FOREIGN PATENT DOCUMENTS

| 0 761 219 | 3/1997 | (EP) . |
| WO 95/14017 | 5/1995 | (WO) . |
| WO 96/24353 | 8/1996 | (WO) . |

*Primary Examiner*—William R. A. Jarvis
(74) *Attorney, Agent, or Firm*—Roger S. Benjamin

(57) ABSTRACT

This invention relates to a method of treating gout with certain indole compounds and other aromatic compounds.

15 Claims, No Drawings

METHOD OF TREATING GOUT WITH CERTAIN INDOLE COMPOUNDS

This application is a 371 of PCT/0598/14262, filed Jul. 8, 1998, which claims priority to prov. appln. No. 60/052,117, filed Jul. 10, 1997.

This invention relates to the use of tryptophan derivatives as inhibitors of neutrophil mediated oxidant production and their use in treating neutrophil associated diseases and disorders.

Neutrophils play a vital role in the resistance of a host to infection. Key characteristics of neutrophils in this role include their ability to adhere initially to the endothelium, to migrate into tissue, and to kill engulfed microbes with oxidants and proteolytic enzymes. Unfortunately, in certain disease states, neutrophils secrete these oxidants and proteolytic enzymes extracellularly resulting in inflammatory diseases and conditions.

The compounds of the present invention have been shown to effectively inhibit adhesion-dependent oxidant production. Accordingly, this invention provides methods of treating disease and conditions associated with excess neutrophil mediated oxidant production, including the following inflammatory diseases and other conditions: smoking, chronic bronchitis, emphysema, asthma, cystic fibrosis, cancer, adult respiratory distress syndrome, Wegener's granulomatosis, idiopathic pulmonary fibrosis, collagen vascular disorders, interstitial lung disease, hypersensitivity pneumonitis, sarcoidosis, bronchiolitis obliterans with organizing pneumonia, Crohn's Disease, Secondary Sjörgren's Syndrome, rheumatoid arthritis, progressive systemic sclerosis, dermatopolymyositis, mixed connective tissue disease, familial idiopathic pulmonary fibrosis, systemic lupus erythematosus, progressive systemic sclerosis, autoimmune thyroid disease, inflammatory bowel disease, juvenile periodontitis, myocardial infarction, hemorrhagic shock, septic shock, ischemic shock, cerebral ischemia, stroke, hypertension, unstable angina, diabetes complications, thrombotic stroke, fibrosing alveolitis, bronchiectasis, periodontal disease, glomerulonephritis, alcoholic hepatitis, Kawasaki Disease, gingivitis, chronic obstructive pulmonary disease, pulmonary infections (staphylococcal or klebsiella pneumonia), ulcerative colitis, psoriasis, artherosclerosis, gout, gastroesophageal reflux disease, carditis, Barrett's Esophagus, Behcet's Disease, iritis, acute glomerulonephritis, periarteritis nodosa, unstable angina, coronary artery disease, coronary angioplasty, immune complex disease, cryoglobulinemic glomerulonephritis, anti-gbm glomerulonephritis, Goodpasture's Syndrome, myositis, and acute pancreatitis.

The invention provides a method for inhibiting neutrophil mediated oxidant production, comprising administering to a mammal in need thereof, a pharmaceutically effective amount of a compound of the formula I:

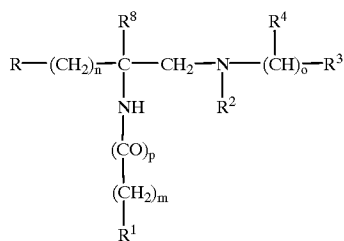

wherein
m is 0, 1, 2, or 3;
n is 0 or 1;
o is 0, 1, or 2;
p is 0 or 1;
R is phenyl, 2- or 3-indolyl, 2- or 3-indolinyl, benzothienyl, benzofuranyl, or naphthyl;
which groups may be substituted with one or two halo, $C_1$–$C_3$ alkoxy, trifluoromethyl, $C_1$–$C_4$ alkyl, phenyl-$C_1$–$C_3$ alkoxy, or $C_1$–$C_4$ alkanoyl groups;
$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_1$–$C_4$ alkyl)-, phenyl-($C_1$–$C_4$ alkoxy)quinolinyl-($C_1$–$C_4$ alkyl)-, isoquinolinyl-($C_1$–$C_4$ alkyl)-, reduced quinolinyl-($C_1$–$C_4$ alkyl)-, reduced isoquinolinyl-($C_1$–$C_4$ alkyl)-, benzoyl-($C_1$–$C_3$ alkyl)-, $C_1$–$C_4$ alkyl, or —NH—$CH_2$—$R^5$;
any one of which $R^1$ groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;
or any one of which $R^1$ groups may be substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;
any one of which groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;
or $R^1$ is amino, a leaving group, hydrogen, $C_1$–$C_4$ alkylamino, or di($C_1$–$C_4$ alkyl)amino;
$R^5$ is pyridyl, anilino-($C_1$–$C_3$ alkyl)-, or anilinocarbonyl;
$R^2$ is hydrogen, $C_1$–$C_4$ alkyl, $C_1$–$C_4$ alkylsulfonyl, carboxy-($C_1$–$C_3$ alkyl)-, $C_1$–$C_3$ alkoxycarbonyl-($C_1$–$C_3$ alkyl)-, or —CO—$R^6$;
$R^6$ is hydrogen, $C_1$–$C_4$ alkyl, $C_1$–$C_3$ haloalkyl, phenyl, $C_1$–$C_3$ alkoxy, $C_1$–$C_3$ hydroxyalkyl, amino, $C_1$–$C_4$ alkylamino, di($C_1$–$C_4$ alkyl)amino, or —$(CH_2)_q$—$R^7$;
q is 0 to 3;
$R^7$ is carboxy, $C_1$–$C_4$ alkoxycarbonyl, $C_1$–$C_4$ alkylcarbonyloxy, amino, $C_1$–$C_4$ alkylamino, di($C_1$–$C_4$ alkyl)amino, $C_1$–$C_6$ alkoxycarbonylamino, or
phenoxy, phenylthio, piperazinyl, piperidinyl, pyrrolidinyl, morpholinyl, indolinyl, indolyl, benzothienyl, benzofuranyl, quinolinyl, isoquinolinyl, reduced quinolinyl, reduced isoquinolinyl, phenyl-($C_1$–$C_4$ alkyl)-, quinolinyl-($C_1$–$C_4$ alkyl)-, isoquinolinyl-($C_1$–$C_4$ alkyl)-, reduced quinolinyl-($C_1$–$C_4$ alkyl)-, reduced isoquinolinyl-($C_1$–$C_4$ alkyl)-, benzoyl-$C_1$–$C_3$ alkyl;
any one of which $R^7$ groups may be substituted with halo, trifluoromethyl, $C_1$–$C_4$ alkoxy, $C_1$–$C_4$ alkyl, amino, $C_1$–$C_4$ alkylamino, di($C_1$–$C_4$ alkyl)amino, or $C_2$–$C_4$ alkanoylamino;
or any one of which $R^7$ groups may be substituted with phenyl, piperazinyl, $C_3$–$C_8$ cycloalkyl, benzyl, piperidinyl, pyridinyl, pyrimidinyl, pyrrolidinyl, $C_2$–$C_6$ alkanoyl, or $C_1$–$C_4$ alkoxycarbonyl;
any of which groups may be substituted with halo, trifluoromethyl, amino, $C_1$–$C_4$ alkoxy, $C_1$–$C_4$ alkyl, $C_1$–$C_4$ alkylamino, di($C_1$–$C_4$ alkyl)amino, or $C_2$–$C_4$ alkanoylamino;

$R^8$ is hydrogen or $C_1$–$C_6$ alkyl;

$R^3$ is phenyl, phenyl-($C_1$–$C_6$ alkyl)-, $C_3$–$C_8$ cycloalkyl, $C_5$–$C_8$ cycloalkenyl, $C_1$–$C_8$ alkyl, naphthyl, $C_2$–$C_8$ alkenyl, or hydrogen;

any one of which groups except hydrogen may be substituted with one or two halo, $C_1$–$C_3$ alkoxy, $C_1$–$C_3$ alkylthio, nitro, trifluoromethyl, or $C_1$–$C_3$ alkyl groups; and $R^4$ is hydrogen or $C_1$–$C_3$ alkyl;

with the proviso that if $R^1$ is hydrogen or halo, $R^3$ is phenyl, phenyl-($C_1$–$C_6$ alkyl)-, $C_3$–$C_8$ cycloalkyl, $C_5$–$C_8$ cycloalkenyl, or naphthyl;

with the proviso that if $R^1$ is hydrogen or halo, $R^3$ is phenyl, phenyl-($C_1$–$C_6$ alkyl)-, $C_3$–$C_8$ cycloalkyl, $C_5$–$C_8$ cycloalkenyl, or naphthyl;

or pharmaceutically acceptable salts, solvates, or prodrugs thereof.

All temperatures stated herein are in degrees Celsius (° C.). All units of measurement employed herein are in weight units except for liquids which are in volume units.

As used herein, the term "$C_1$–$C_8$ alkyl" refers to straight or branched, monovalent, saturated aliphatic chains of 1 to 8 carbon atoms and includes, but is not limited to, methyl, ethyl, propyl, isopropyl, butyl, isobutyl, t-butyl, pentyl, isopentyl, hexyl and the like. The term "$C_1$–$C_8$ alkyl" includes within its definition the terms "$C_1$–$C_6$ alkyl" and "$C_1$–$C_4$ alkyl".

"Divalent($C_1$–$C_4$) alkyl" represents a straight or branched divalent saturated aliphatic chain having from one to four carbon atoms. Typical divalent($C_1$–$C_4$) alkyl groups include methylene, ethylene, propylene, 2-methylpropylene, butylene and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Hydroxy($C_1$–$C_4$)alkyl" represents a straight or branched alkyl chain having from one to four carbon atoms with hydroxy group attached to it. Typical hydroxy($C_1$–$C_4$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl and the like.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_4$ alkylthio".

The term "$C_2$–$C_6$ alkenyl" as used herein represents a straight or branched, monovalent, unsaturated aliphatic chain having from two to six carbon atoms. Typical $C_2$–$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

"$C_5$–$C_8$ cycloalkenyl" represents a hydrocarbon ring structure containing from five to eight carbon atoms and having at least one double bond within that ring, which is unsubstituted or substituted with 1, 2 or 3 substituents independently selected from halo, halo($C_1$–$C_4$) alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or —($CH_2$)$_a$—$R^c$ where a is 1, 2, 3 or 4 and $R^c$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

"$C_1$–$C_4$ alkylamino" represents a straight or branched alkylamino chain having from one to four carbon atoms attached to an amino group. Typical $C_1$–$C_4$ alkyl-amino groups include methylamino, ethylamino, propylamino, isopropylamino, butylamino, sec-butylamino and the like.

"Di($C_1$–$C_4$ alkyl)amino" represents a straight or branched dialkylamino chain having two alkyl chains, each having independently from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"Arylsulfonyl" represents an aryl moiety attached to a sulfonyl group. "Aryl" as used in this term represents a phenyl, naphthyl, heterocycle, or unsaturated heterocycle moiety which is optionally substituted with 1, 2 or 3 substituents independently selected from halo, halo($C_1$–$C_4$) alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or —($CH_2$)$_a$—$R^b$ where a is 1, 2, 3 or 4; and $R^b$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$)-alkylcarbamoyl, amino, $C_1$–$C_4$ alkylamino, di($C_1$–$C_4$) alkylamino or —($CH_2$)$_a$—$R^d$ where a is 1, 2, 3 or 4; and $R^d$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$) alkylcarbamoyl, amino, $C_1$–$C_4$ alkylamino, di($C_1$–$C_4$) alkylamino or —($CH_2$)$_a$—$R^e$ where a is 1, 2, 3 or 4; and $R^e$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydroisoquinolinyl, 3-methylimidazolyl, 3-methoxypyridyl, 4-chloroquinolinyl, 4-aminothiazolyl, 8-methyiquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethyl-1naphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$–$C_8$ cycloalkyl" represents a saturated hydrocarbon ring structure containing from three to eight carbon atoms which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or —($CH_2$)$_a$—$R^f$ where a is 1, 2, 3 or 4 and $R^f$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical $C_3$–$C_8$ cycloalkyl groups include cyclopropyl, cyclopentyl, cyclohexyl, cycloheptyl, 3-methyl-cyclopentyl, 4-ethoxycyclohexyl, 4-carboxycycloheptyl, 2-chlorocyclohexyl, cyclobutyl, cyclooctyl, and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)eethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, "Protective Groups in Organic Synthesis" (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2', 4,4'-tetramethoxybenzhydryl, t-butyl, t-amyl, trityl, 4-methoxytrityl, 4,4'-dimethoxytrityl, 4,4', 4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al., supra, at Chapter 5.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The compounds used in the methods of the present invention have multiple asymmetric centers. As a consequence of these chiral centers, the compounds occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As noted suora, this invention includes the use of pharmaceutically acceptable salts of the compounds defined by Formula I. A compound of formula I can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the use of pharmaceutically acceptable solvates of the compounds of Formula I. Many of the Formula I compounds can combine with solvents such as water, methanol, ethanol and acetonitrile to form pharmaceutically acceptable solvates such as the corresponding hydrate, methanolate, ethanolate and acetonitrilate.

The especially preferred compounds used in the methods of this invention are those of Formula I wherein
  a) R is substituted or unsubstituted 2- or 3-indolyl, phenyl, or naphthyl;
  b) n is 1;
  c) $R^1$ is phenyl, substituted phenyl, piperidinyl, substituted piperidinyl, piperazinyl, substituted piperazinyl, pyrrolidinyl, pyridyl, benzoyl, or morpholinyl;
  d) $R^2$ is —CO—$R^6$, $C_1$–$C_4$ alkylsulfonyl, or $C_1$–$C_3$ alkoxycarbonyl-($C_1$–$C_3$ alkyl)-;
  e) $R^3$ is phenyl, substituted phenyl, $C_3$–$C_8$ cycloalkyl, substituted $C_3$–$C_8$ cycloalkyl, naphthyl or substituted naphthyl; and
  f) $R^8$ is hydrogen or methyl.

A most preferred group of compounds used in the methods of this invention are those of Formula I wherein R is optionally substituted indolyl, $R^1$ is substituted piperidinyl or substituted piperazinyl, $R^8$ is hydrogen, and $R^2$ is acetyl or methylsulfonyl. Another preferred group of compounds used in the methods of this invention are those of Formula I wherein R is naphthyl, $R^1$ is optionally substituted phenyl, substituted piperidinyl or substituted piperazinyl, $R^2$ is acetyl or methylsulfonyl, and $R^3$ is phenyl or substituted phenyl.

The especially preferred compounds employed in the present invention are those of Formula I wherein
  a) R is substituted or unsubstituted 2- or 3-indolyl, phenyl, or naphthyl;
  b) n is 1;
  c) $R^1$ is trityl, phenyl, substituted phenyl, piperidinyl, substituted piperidinyl, piperazinyl, substituted piperazinyl, pyrrolidinyl, pyridyl, benzoyl, or morpholinyl;
  d) $R^2$ is —CO—$R^6$, $C_1$–$C_4$ alkylsulfonyl, or $C_1$–$C_3$ alkoxycarbonyl-($C_1$–$C_3$ alkyl)-;
  e) $R^3$ is phenyl, substituted phenyl, $C_3$–$C_8$ cycloalkyl, substituted $C_3$–$C_8$ cycloalkyl, naphthyl or substituted naphthyl; and
  f) $R^8$ is hydrogen or methyl.

The compounds employed in the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

Examples of such protocols are depicted in Schemes I through IV. The coupling of the substituted amine to the compound of Formula II (Method A) can be performed by many means known in the art, the particular methods employed being dependent upon the particular compound of Formula II which is used as the starting material and the type of substituted amine used in the coupling reaction. These coupling reactions frequently employ commonly used coupling reagents such as 1,1-carbonyl diimidazole, dicyclohexylcarbodiimide, diethyl azodicarboxylate, 1-hydroxybenzotriazole, alkyl chloroformate and triethylamine, phenyldichlorophosphate, and chlorosulfonyl isocyanate. Examples of these methods are described infra. After deprotection of the amino group, the compounds of Formula III are obtained.

The compound of Formula III is then reduced, converting the amide into an amine (Method B). Amides can be reduced to amines using procedures well known in the art. These reductions can be performed using lithium aluminum hydride as well as by use of many other different aluminum-based hydrides. Alternatively, the amides can be reduced by catalytic hydrogenation, though high temperatures and pressures are usually required for this. Sodium borohydride in combination with other reagents may be used to reduce the amide. Borane complexes, such as a borane dimethylsulfide complex, are especially useful in this reduction reaction.

The next step in Scheme I (Method C) is the selective acylation of the primary amine using standard methods, as typified by Method C. Because of the higher steric demand of the secondary amine, the primary amine is readily available for selective substitution.

This acylation can be done using any of a large number of techniques regularly employed by those skilled in organic chemistry. One such reaction scheme is a substitution using an anhydride such as acetic anhydride. Another reaction scheme often employed to acylate a primary amine employs a carboxylic acid preferably with an activating agent as described for Method A, supra. An amino-de-alkoxylation type of reaction uses esters as a means of acylating the primary amine. Activated esters which are attenuated to provide enhanced selectivity are very efficient acylating agents.

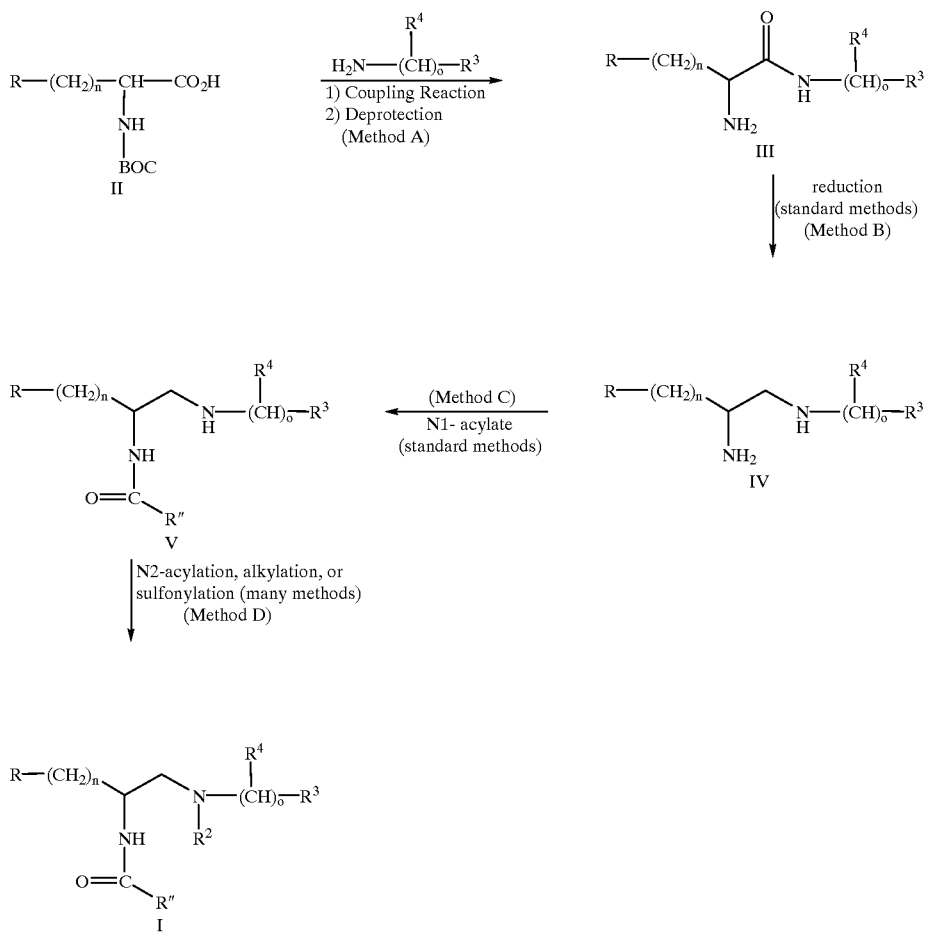

Scheme I wherein:

R″ is —(CH$_2$)$_m$—R$^1$; and

R$^2$ is not hydrogen.

Scheme II

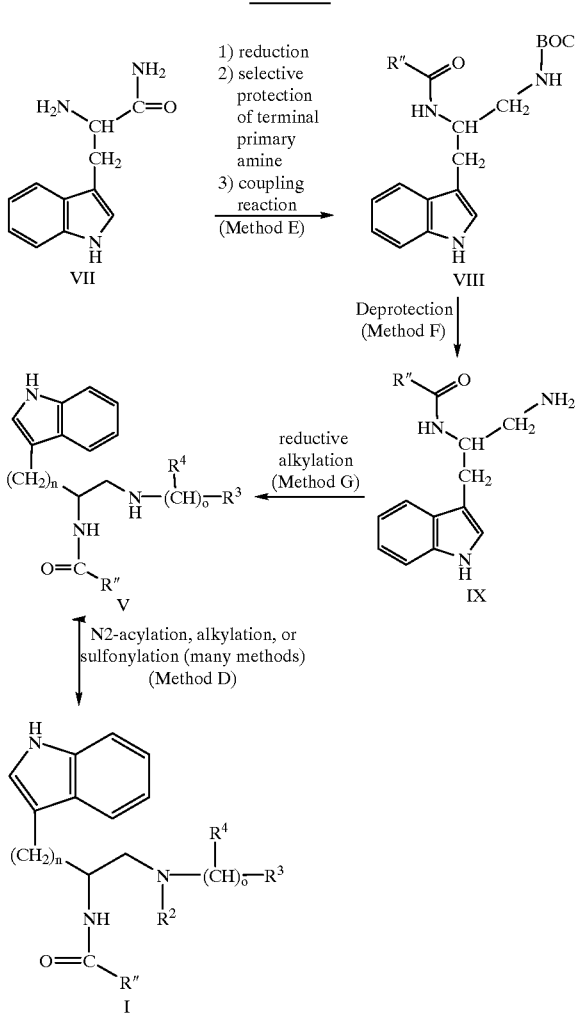

Scheme III

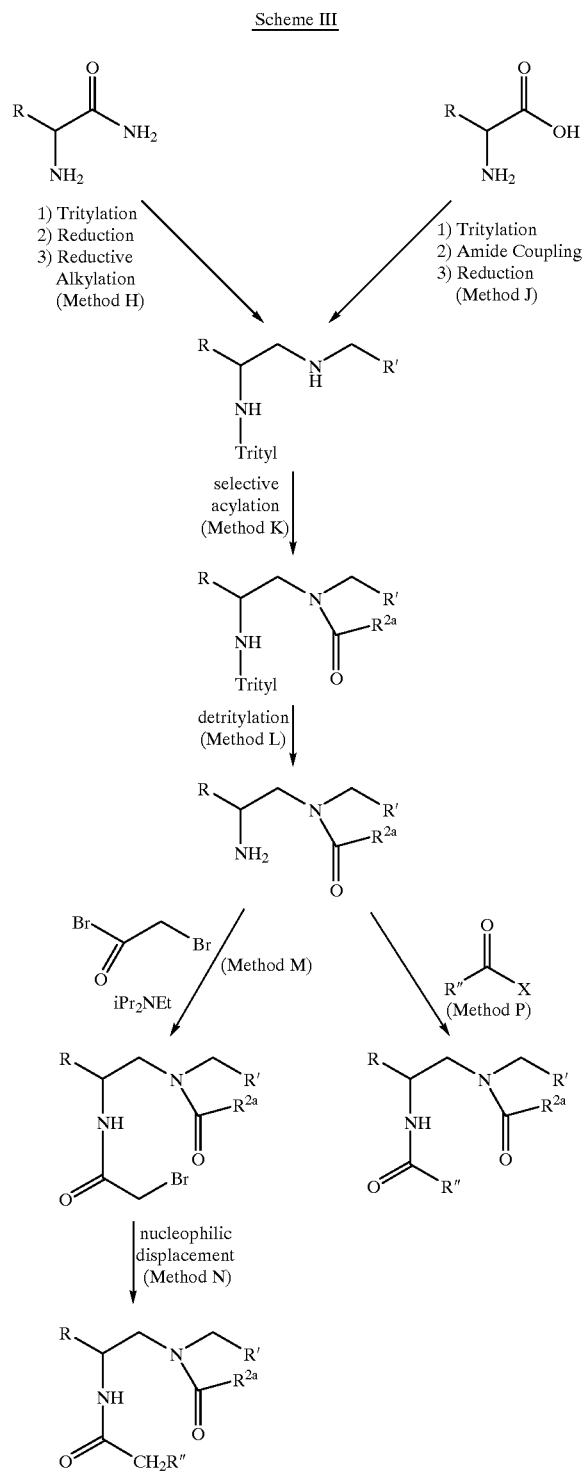

Schemes II and III depict alternative protocols and strategies for the synthesis of the compounds of Formula I. Many of the individual reactions are similar to those described in Scheme I but the reactions of Schemes II and III are done in a different, but yet well known to those skilled in the art, series of steps.

Primary amines can also be acylated using amides to perform what is essentially an exchange reaction. This reaction is usually carried out with the salt of the amine. Boron trifluoride, usually in the form of a boron trifluoride diethyl ether complex, is frequently added to this reaction to complex with the leaving ammonia.

The next procedure is one of substitution of the secondary amine (Method D). For most of the compounds of Formula I this substitution is one of alkylation, acylation, or sulfonation. This substitution is usually accomplished using well recognized means. Typically, alkylations can be achieved using alkyl halides and the like as well as the well-known reductive alkylation methods as seen in Method G, Scheme II, supra, employing aldehydes or ketones. Many of the acylating reaction protocols discussed suora efficiently acylate the secondary amine as well. Alkyl- and aryl-sulfonyl chlorides can be employed to sulfonate the secondary amine.

In many instances one of the later steps in the synthesis of the compounds of Formula I is the removal of an amino- or carboxy-protecting group. Such procedures, which vary, depending upon the type of protecting group employed as well as the relative lability of other moieties on the compound, are described in detail in many standard references works such as T. W. Greene, et al., Protective Groups in Organic Synthesis (1991).

wherein $R^{2a}$ coupled with the carbonyl group to which it is attached is equal to $R^2$.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., "Enantiomers, Racemates, and Resolutions", (1991).

In addition to the schemes described above, the practitioner of this invention may also choose an enantiospecific protocol for the preparation of the compounds of Formula I. Scheme IV, infra, depicts a typical such synthetic reaction design which maintains the chiral center present in the starting material in a desired orientation, in this case in the "R" configuration. These reaction schemes usually produce compounds in which greater than 95 percent of the title product is the desired enantiomer.

Many of the synthetic steps employed in Scheme IV are the same as used in other schemes, especially Scheme III.

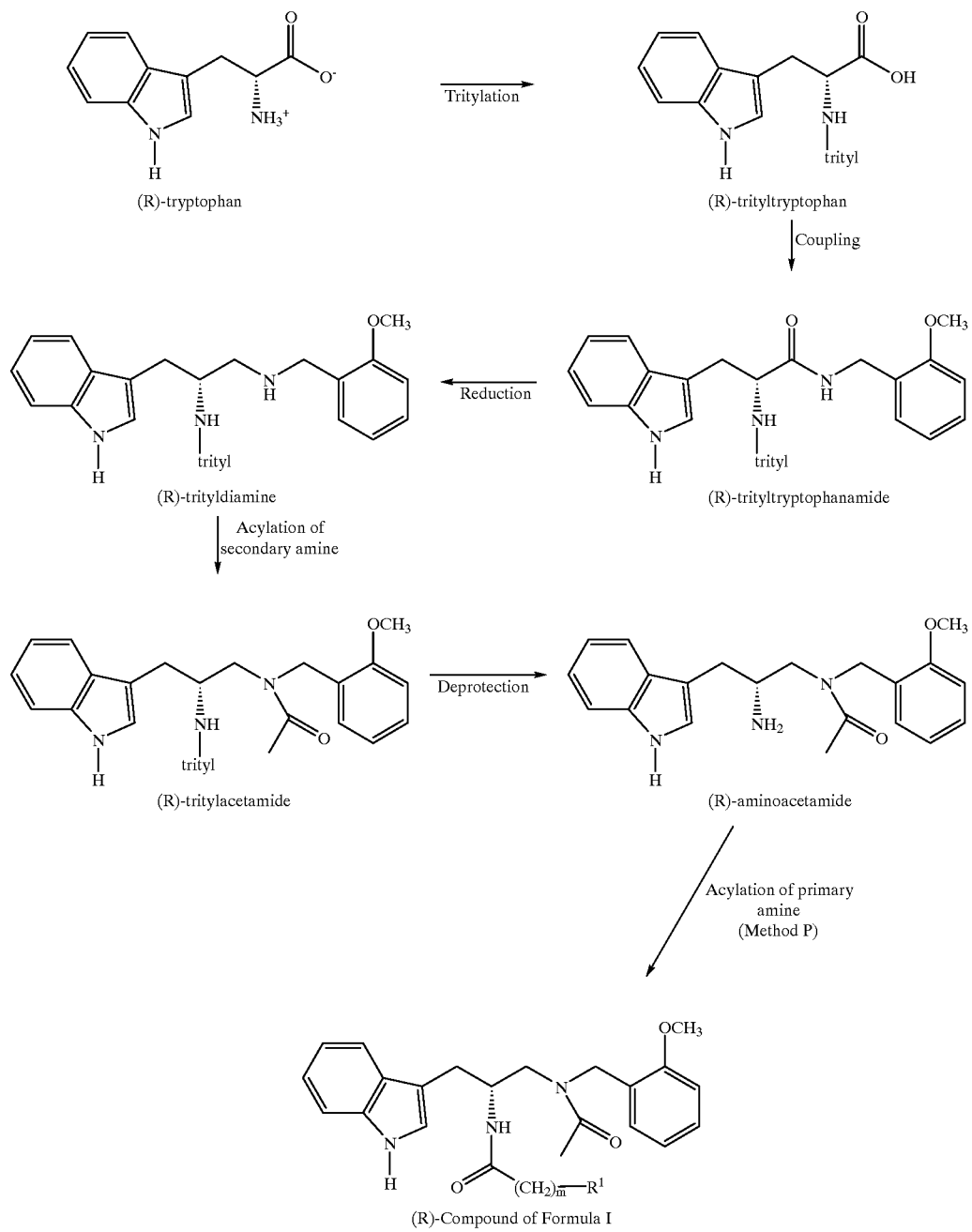

METHOD A

Coupling of Carboxylic Acid and Primary Amine to Form Amide

Preparation of 2-t-butoxycarbonylamino-3-(1H-indol-3-yl)-N-(2-methoxybenzyl)propanamide To a solution of N-(t-butoxycarbonyl)tryptophan (46.4 g, 152.6 mmoles) in 500 ml of dioxane was added carbonyl diumidazole (25.4 g, 156 mmoles) in a portionwise manner. The resulting mixture was stirred for about 2.5 hours at room temperature and then stirred at 450° C. for 30 minutes. Next, 2-methoxybenzylamine (20.7 ml, 158.7 mmoles) was added and the reaction mixture was then stirred for 16 hours at room temperature.

The dioxane was removed under reduced pressure. The product was partitioned between ethyl acetate and water and was washed successively with 1 N hydrochloric acid, saturated sodium bicarbonate solution, water, and brine, followed by drying over sodium sulfate and removal of the solvent. Final crystallization from methanol yielded 52.2 g of homogeneous product as yellow crystals. Yield 80.8%. m.p. 157–160° C.

Deprotection of Primary Amine

Synthesis of 2-amino-3-(1H-indol-3-yl)-N-(2-methoxybenzyl)propanamide

To a mixture of the 2-t-butoxycarbonylamino-3-(1H-indol-3-yl)-N-(2-methoxybenzyl)propanamide prepared supra (25.1 g, 59.2 mmoles) and anisole (12 ml, 110.4 mmoles) at 0° C. was added dropwise an aqueous solution of trifluoroacetic acid (118 ml, 1.53 moles) in 50 ml of water. This mixture was stirred for one hour at 0° C., followed by stirring for about 2.5 hours at ambient temperature. The mixture was then refrigerated for about 16 hours.

The volatiles were removed under reduced pressure. The product was partitioned between ethyl acetate and saturated sodium bicarbonate solution and was then washed with water followed by brine and then dried over sodium sulfate. The solvents were removed in vacuo. Recrystallization from a 1:1 diethyl ether/cyclohexane solution yielded 18.0 g (94.2%) of homogeneous product as an off-white powder. m.p. 104–180° C.

METHOD B

Reduction of Amide Carbonyl

Synthesis of 2-amino-3-(1H-indol-3-yl)-3-[N-(2-methoxybenzyl)amino]propane

To a refluxing solution of 2-amino-3-(1H-indol-3-yl)-N-(2-methoxybenzyl)propanamide (9.81 g, 30.3 mmoles), prepared as described supra, in 100 ml of anhydrous tetrahydrofuran was added dropwise a 10M borane-methyl sulfide complex (9.1 ml, 91.0 mmoles). The resulting mixture was refluxed for about 2 hours. The mixture was cooled to room temperature and the excess borane was quenched by the dropwise addition of 160 ml of methanol. The resulting mixture was refluxed for 15 minutes and the methanol was removed under reduced pressure.

The residue was dissolved in a saturated methanol solution of hydrochloric acid (250 ml) and the solution refluxed for about 1 hour. The methanol was removed in vacuo and the product was isolated the addition of 5 N sodium hydroxide followed by extraction with diethyl ether. The product was then dried over sodium sulfate. The solvents were removed in vacuo. Flash chromatography (silica gel, eluting with methanol:methylene chloride:ammonium hydroxide, 10:100:0.5) provided 7.1 g of a mixture of the title compound (75%) and the indoline derivative of the title product (25%) as an amber oil.

METHOD C

Acylation of Primary Amine

Preparation of 3-(1H-indol-3-yl)-1-[N-(2-methoxybenzyl)amino]-2-[N-(2-((4-phenyl)piperazin-1-yl)acetyl)amino]propane A mixture of 2-((4-phenyl)piperazin-1-yl)acetic acid, sodium salt (1.64 g, 6.8 mmoles) and triethylamine hydrobromide (1.24 g, 6.8 mmoles) in 35 ml of anhydrous dimethylformamide was heated to 50° C. and remained at that temperature for about 35 minutes. The mixture was allowed to cool to room temperature. 1,1-Carbonyl diumidazole (1.05 g, 6.5 mmoles) and 10 ml of anhydrous dimethylformamide were added to the mixture. The resulting mixture was stirred for about 3 hours at room temperature.

A solution of the 2-amino-3-(1H-indol-3-yl)-1-[N-(2-methoxybenzyl)amino]propane (75%) and the indoline derivative (25%) prepared sunra, dissolved in 10 ml of anhydrous dimethylformamide was added to the previous reaction mixture. The resulting mixture was stirred for about 16 hours at room temperature. The dimethylformamide was removed under reduced pressure.

The title product and its indoline derivative were partitioned between ethyl acetate and water and then washed with brine, and dried over sodium sulfate. The solvents were removed in vacua. This process yielded 3.2 g of a mixture of the title compound and its indoline derivative as a yellow oil. These two compounds were then separated using high performance liquid chromatography using a reverse phase column followed by a silica gel column to give the title product (5.2% yield) as a yellow foam.

METHOD D

Techniques of Acylation of Secondary Amine

Preparation of 1-[N-ethoxycarbonyl-N-(2-methoxybenzyl)amino]-3-(1H-indol-3-yl)-2-[N-(2-((4-phenyl)piperazin-1-yl)acetyl)amino]propane To a solution of the 3-(1H-indol-3-yl)1-[N-(2-methoxybenzyl)amino]-2-[N-(2-((4-phenyl)piperazin-1-yl)acetyl)amino]propane (0.43 g, 0.85 mmole) and triethylamine (130 μl, 0.93 mmole) in 5 ml of anhydrous tetrahydrofuran, was added dropwise ethylchloroformate (89 μl, 0.93 mmole). The resulting mixture was stirred for about 16 hours at room temperature. The tetrahydrofuran was removed under reduced pressure.

The acylated product was partitioned between ethyl acetate and 0.2 N sodium hydroxide, and was then washed with water and brine successively, then dried over sodium sulfate. Flash chromatography (silica gel, methanol:methylene chloride, 2.5:97.5) provided 390 mg of homogeneous title product as a white foam.

Preparation of 3-(1H-indol-3-yl)-1-[N-(2-methoxybenzyl)-N-(methylaminocarbonyl)amino]-2-[N-(2-((4-phenyl)piperazin-1-yl)acetyl)amino]propane To a room temperature solution of 3-(1H-indol-3-yl)-1-[N-(2-methoxybenzyl)amino]-2-[N-(2-((4-phenyl)

piperazin-1-yl)acetyl)amino]propane (0.40 g, 0.78 mmole) in 10 ml of anhydrous tetrahydrofuran was added dropwise methyl isocyanate (140 µl, 2.3 mmoles). The resulting mixture was then stirred for 16 hours at room temperature. The tetrahydrofuran was removed in vacuo. The title product was isolated by consecutive washes with ethyl acetate, water, and brine, and then dried over sodium sulfate. Flash chromatography using silica gel and a methanol/methylene chloride (5/95) eluant provided 396 mg of the homogeneous product as a yellow oil.

Alkylation of Secondary Amine

Preparation of 1-[N-ethyl-N-(2-methoxybenzyl) amino]-3-(1H-indol-3-yl)-2-[N-(2-((4 phenyl) piperazin-1-yl)acetyl)amino]propane To a room temperature solution of 3-(1H-indol-3-yl)-1-[N-(2-methoxybenzyl)amino]-2-[N-(2-((4-phenyl) piperazin-1-yl)acetyl)amino]propane (0.41 g, 0.80 mmole) in 5 ml of anhydrous N,N-dimethylformamide were added ethyl iodide (120 µl, 1.5 mmoles) and potassium carbonate (120 mg, 0.87 mmole). This mixture was then heated to 50° C. and maintained at that temperature for about 4 hours after which it was stirred at room temperature for about 16 hours. The N,N-dimethylformamide was then removed under reduced pressure. The product was partitioned between ethyl acetate and water, and then washed with brine, before drying over sodium sulfate. The solvents were removed in vacuo. Preparative thin layer chromatography provided 360 mg of the title product as a yellow foam.

METHOD E

Reduction of the Carbonyl of an Amide

Preparation of 1,2-diamino-3-(1H-indol-3-yl) propane

Boron trifluoride etherate (12.3 ml, 0.1 mmole) was added to a tetrahydrofuran (24.4 ml) solution of tryptophan amide (20.3 g, 0.1 mole) at room temperature with stirring. At reflux with constant stirring, borane methylsulfide (32.25 ml, 0.34 mole) was added dropwise. The reaction was heated at reflux with stirring for five hours. A tetrahydrofuran:water mixture (26 ml, 1:1) was carefully added dropwise. A sodium hydroxide solution (160 ml, 5N) was added and the mixture heated at reflux with stirring for sixteen hours.

The layers of the cooled mixture were separated and the aqueous was extracted twice with 40 ml each of tetrahydrofuran. These combined tetrahydrofuran extracts were evaporated. Ethyl acetate (800 ml) was added and this solution was washed three times with 80 ml saturated sodium chloride solution. The ethyl acetate extract was dried over sodium sulfate, filtered and evaporated to yield 18.4 g (97%) of the title compound.

Protection of Primary Amine

Preparation of the 2-amino-1-t-butoxycarbonylamino-3-(1H-indol-3-yl)propane.

Di-t-butyldicarbonate (0.90 ml, 3.9 mmoles) in 10 ml of tetrahydrofuran was added dropwise at room temperature to the 1,2-diamino-3-(1H-indol-3-yl)propane (1.06 g, 5.6 mmoles) produced supra, which was dissolved in 28 ml of tetrahydrofuran. This dropwise addition occurred over a 5 hour period. The solvent was evaporated. Flash chromatography using ethanol/ammonium hydroxide/ethylacetate yielded 0.51 g (1.76 mmoles, 31%) of the desired carbamate.

Acylation of the Secondary Amine

Preparation of 1-t-butoxycarbonylamino-3-(1H-indol-3-yl)-2-[N-(2-((4-phenyl)piperazin-1-yl)acetyl) amino]propane A slurry of 2-((4-phenyl)piperazin-1-yl)acetic acid (2.47 g, 11.2 mmoles) and triethylamine (3.13 ml, 22.5 mmoles) in acetonitrile (1200 ml) was heated to reflux briefly with stirring. While the resulting solution was still warm carbonyldiimidazole (1.82 g, 11.2 mmoles) was added and the mixture was heated at reflux for 10 minutes. The 2-amino-1-t-butoxycarbonylamino-3-(1H-indol-3yl)-propane (3.25 g, 11.2 mmoles) in 50 ml of acetonitrile was then added to the reaction. The resulting mixture was refluxed with stirring for 30 minutes and was then stirred at room temperature overnight.

The reaction mixture was then refluxed with stirring for 5 hours and the solvent was then removed in vacuo. The resulting oil was washed with a sodium carbonate solution, followed by six washes with water, which was followed by a wash with a saturated sodium chloride solution. The resulting liquid was dried over sodium sulfate and filtered. The retained residue was then dried in vacuo. The filtrate was reduced in volume and then partially purified by chromatography. The sample from the chromatography was pooled with the residue retained by the filter, combining for 3.94 grams (72% yield) of the title product.

METHOD F

Deprotection of Primary Amine

Synthesis of 1-amino-3-(1H-indol-3-yl)-2-[N-(2-((4-phenyl)piperazin-1-yl)acetyl)amino]propane To an ice cold solution of 70% aqueous trifluoroacetic acid (2.8 ml of trifluoroacetic acid in 4.0 ml total volume) were added 1-t-butoxycarbonylamino-3-(1H-indol-3-yl)-2-[N-(2-((4-phenyl)piperazin-1-yl)acetyl)amino]propane (0.80 g, 1.63 mmoles) and anisole (0.4 ml). This mixture was stirred for 35 minutes, resulting in a clear solution. The solution was then stirred for an additional hour and then evaporated.

Ethyl acetate was then added to the resulting liquid, followed by a wash with a sodium carbonate solution. This wash was then followed by three washes with a saturated sodium chloride solution. The resulting solution was then dried over sodium sulfate, filtered and evaporated, resulting in 0.576 g (90% yield) of the title product.

METHOD G

Reductive Alkylation of Primary Amine

Preparation of 1-[N-(2-chlorobenzyl)amino]-3-(1H-indol-3-yl)-2-[N-(2-((4-phenyl)piperazin-1-yl)acetyl) amino]propane 2-Chlorobenzaldehyde (0.112 g, 0.8 mmole) was combined with the 1-amino-3-(1H-indol-3-yl)-2-[N-(2-((4-phenyl)piperazin-1-yl)acetyl)amino]propane (0.156 g, 0.398 mmole) in toluene. The resulting mixture was then stirred and warmed, and then evaporated. Toluene was then added to the residue and this mixture was again evaporated. Tetrahydrofuran was added to the residue and the mixture was then cooled in an ice bath.

Sodium cyanoborohydride (0.025 g, 0.4 mmole) was then added to the reaction mixture. Gaseous hydrogen chloride was periodically added above the liquid mixture. The mixture was stirred at room temperature for 16 hours and then reduced in volume in vacuo.

A dilute hydrochloric acid solution was then added to the residue and the solution was then extracted twice with ether. The acidic aqueous extract was basified by the dropwise addition of 5N sodium hydroxide. This basified solution was then extracted three times with ethyl acetate. The combined ethyl acetate washes were washed with a saturated sodium chloride solution, dried over sodium sulfate, filtered and evaporated. This process was followed by chromatography yielding 0.163 g (79% yield) of the title product.

METHOD H

Tritylation

Preparation of 3-(1H-indol-3-yl)-2-(N-triphenylmethylamino)propanamide

Tryptophan amide (26.43 g, 0.130 mole) was suspended in 260 ml of methylene chloride and this mixture was flushed with nitrogen and then put under argon. Trityl chloride (38.06 g, 0.136 mole) was dissolved in 75 ml of methylene chloride. The trityl chloride solution was slowly added to the tryptophan amide solution which sat in an ice bath, the addition taking about 25 minutes. The reaction mixture was then allowed to stir overnight.

The reaction mixture was then poured into a separation funnel and was washed with 250 ml of water, followed by 250 ml of brine. As the organic layer was filtering through sodium sulfate to dry, a solid precipitated. The filtrate was collected and the solvent was evaporated.

Ethyl acetate was then added to the pooled solid and this mixture was stirred and then refrigerated overnight. The next day the resulting solid was washed several times with cold ethyl acetate and then dried in vacuo. Yield 49.76 g (85.9%).

Reduction of Carbonyl

Preparation of 1-amino-3-(1H-indol-3-yl)-2-(N-triphenylmethylamino)propane

Under argon the 3-(1H-indol-3-yl)-2-(N-triphenylmethylamino)propanamide (48.46 g, 0.108 mole) was suspended in 270 ml of tetrahydrofuran. This mixture was then heated to reflux. Borane-methyl sulfide complex (41.3 g, 0.543 mole) was then slowly added to the reaction mixture. All of the starting amide dissolved during the addition of the borane-methyl sulfide complex. This solution was then stirred overnight in an 83° C. oil bath.

After cooling a 1:1 mixture of tetrahydrofuran:water (75 ml total) was then added to the solution. Sodium hydroxide (5N, 230 ml) was then added to the mixture, which was then heated to reflux for about 30 minutes.

After partitioning the aqueous and organic layers, the organic layer was collected. The aqueous layer was then extracted with tetrahydrofuran. The organic layers were combined and the solvents were then removed by evaporation. The resulting liquid was then partitioned between ethyl acetate and brine and was washed a second time with brine. The solution was then dried over sodium sulfate and the solvents were removed in vacuo to yield 48.68 grams of the desired intermediate.

Substitution of Primary Amine

Preparation of 1-[N-(2-methoxybenzyl)amino]-3-(1H-indol-3-yl)-2-(N-triphenylmethylamino)propane To a mixture of 1-amino-3-(1H-indol-3-yl)-2-(N-triphenylmethylamino)propane (48.68 g, 0.109 mole) dissolved in toluene (1.13 l) was added 2-methoxybenzaldehyde (23.12 g, 0.169 mole), the 2-methoxybenzaldehyde having been previously purified by base wash. The reaction mixture was stirred overnight. The solvents were then removed in vacuo.

The recovered solid was dissolved in 376 ml of a 1:1 tetrahydrofuran:methanol mixture. To this solution was added sodium borohydride (6.83 g, 0.180 mole). This mixture was stirred on ice for about 4 hours. The solvents were removed by evaporation. The remaining liquid was partitioned between 1200 ml of ethyl acetate and 1000 ml of a 1:1 brine: 20N sodium hydroxide solution. This was extracted twice with 500 ml of ethyl acetate each and then dried over sodium sulfate. The solvents were then removed by evaporation overnight, yielding 67.60 grams (>99% yield) of the desired product.

METHOD J

Tritylation

Preparation of 3-(1H-indol-3-yl)-2-(N-triphenylmethylamino)propanoic acid [N-trityltryptophan]

Chlorotrimethylsilane (70.0 ml, 0.527 moles) was added at a moderate rate to a stirring slurry of tryptophan (100.0 g, 0.490 mole) in anhydrous methylene chloride (800 ml) under a nitrogen atmosphere. This mixture was continuously stirred for 4.25 hours. Triethylamine (147.0 ml, 1.055 moles) was added followed by the addition of a solution of triphenylmethyl chloride (147.0 g, 0.552 mole) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2x) and brine (2x) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mole) of analytically pure 3-(1H-indol-3-yl)-2-(N-triphenylmethylamino) propanoic acid was isolated as a light tan solid in two crops giving a total of 79% yield.

Coupling

Preparation of 3-(1H-indol-3-yl)-N-(2-methoxybenzyl)-2-(N-triphenylmethylamino) propanamide To a stirring solution of 3-(1H-indol-3-yl)-2-(N-triphenylmethylamino)propanoic acid (179.8 g, 0.403 mole), 2-methoxybenzylamine (56.0 ml, 0.429 mole), and hydroxybenzotriazole hydrate (57.97 g, 0.429 mole) in anhydrous tetrahydrofuran (1.7 L) and anhydrous N,N-dimethylformamide (500 ml) under a nitrogen atmosphere at 0° C., were added triethylamine (60.0 ml, 0.430 mole) and 1-(3-dimethylaminopropyl)-3-ethoxycarbodiimide hydrochloride (82.25 g, 0.429 mole). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2x), saturated sodium bicarbonate solution (2×), and brine (2×) was performed. The organic layer was dried over anhydrous sodium sulfate, filtered, and concentrated to dryness on a rotary evaporator. The title product was then filtered as a pink solid in two lots. Isolated 215.8 g (0.381 mole) of analytically pure material (95% yield).

Reduction

Preparation of 3-(1H-indol-3-yl)1-[N-(2-methoxybenzyl)amino]-2-(N-triphenylmethylamino)propane Red-Al®, [a 3.4 M, solution of sodium bis(2-methoxyethoxy)aluminum hydride in toluene] (535 ml, 1.819 moles), dissolved in anhydrous tetrahydrofuran (400 ml) was slowly added using an addition funnel to a refluxing solution of the acylation product, 3-(1H-indol-3-yl)-N-(2-methoxybenzyl)-2-(N-triphenylmethylamino)propanamide (228.6 g, 0.404 mols) produced supra, in anhydrous tetrahydrofuran (1.0 liter) under a nitrogen atmosphere. The reaction mixture became a purple solution. The reaction was quenched after at least 20 hours by the slow addition of excess saturated Rochelle salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

METHOD K

Acylation

Preparation of 3-(1H-indol-3-yl)-1-[N-(2-methoxybenzyl)acetylamino]-2-(N-triphenylmethylamino)propane To a stirring solution of 3-(1H-indol-3-yl)-1-[N-(2-methoxybenzyl)amino]-2-(N-triphenylmethylamino)propane (0.404 mole) in anhydrous tetrahydrofuran (1.2 liters) under a nitrogen atmosphere at 0° C. was added triethylamine (66.5 ml, 0.477 mole) and acetic anhydride (45.0 ml, 0.477 mole). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of 3-(1H-indol-3-yl)-1-[N-(2-methoxybenzyl)acetylamino]-2-(N-triphenylmethylamino)propane was crystallized and isolated over three crops giving 208.97 grams (87% yield) of analytically pure material.

METHOD L

Detritylation

Preparation of 2-amino-3-(1H-indol-3-yl)1-[N-(2-methoxybenzyl)acetylamino]propane Formic acid (9.0 ml, 238.540 mmoles) was added to a stirring solution of 3-(1H-indol-3-yl)-1-[N-(2-methoxybenzyl)acetylamino]-2-(N-triphenylmethylamino)propane (14.11 g, 23.763 mmoles) in anhydrous methylene chloride under a nitrogen atmosphere at 0° C. After 4 hours, the reaction mixture was concentrated to an oil on a rotary evaporator and redissolved in diethyl ether and 1.0 N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound 2-amino-3-(1H-indol-3-yl)-1-[N-(2-methoxybenzyl)acetylamino]propane (7.52 g, 21.397 mmols) was isolated giving a 90% yield. No further purification was necessary.

METHOD M

Bromoacetylation

Preparation of 2-[(2-bromo)acetyl]amino-3-(1H-indol-3-yl)-1-[N-(2-methoxybenzyl)acetylamino]propane To a stirring solution of 2-amino-3-(1H-indol-3-yl)-1-[N-(2-methoxybenzyl)acetylamino]propane (7.51 g, 21.369 mmoles) in anhydrous tetrahydrofuran (100 ml) under a nitrogen atmosphere at 0° C. was added diisopropylethylamine (4.1 ml, 23.537 mmoles) and bromoacetyl bromide (2.05 ml, 23.530 mmoles). After 2 hours, ethyl acetate was added and the reaction mixture washed with water twice, 1.0 N hydrochloric acid (2×), saturated sodium bicarbonate solution (2×), and brine. The organic layer was dried over anhydrous sodium sulfate, filtered, and concentrated to a tan foam on a rotary evaporator. In this manner the 2-[(2-bromo)acetyl]amino-3-(1H-indol-3-yl)1-[N-(2-methoxybenzyl)acetylamino]propane was obtained in quantitative yield. No further purification was necessary.

METHOD N

Nucleophilic Displacement

Preparation of 1-[N-(2-methoxybenzyl)acetylamino]-3-(1H-indol-3-yl)-2-[N-(2-((4-cyclohexyl)piperazin-1-yl)acetyl)amino]propane 1-Cyclohexylpiperazine (3.65 g, 22.492 mmoles) was added to a stirring solution of 2-[(2-bromo)acetyl]amino-3-(1H-indol-3-yl)-1-[N-(2-methoxybenzyl)acetylamino]propane (21.369 mmoles) and powdered potassium carbonate (3.56 g, 25.758 mmols) in methylene chloride under a nitrogen atmosphere. The reaction mixture was stirred overnight at room temperature. The salts were filtered and the solution concentrated to a brown foam on a rotary evaporator. The desired product was purified on a Prep 500 column using a 10 L gradient starting with 100% methylene chloride and ending with 5% methanol/94.5% methylene chloride/0.5% ammonium hydroxide. Impure fractions were combined and purified further by reverse phase preparative high performance liquid chromatography (methanol/acetonitrile/water/ammonium acetate). After combining the material from both chromatographic purifications the title compound (10.43 g, 18.663 mmoles) was isolated (87% yield).

An alternative means of acylation of the primary amine as shown in the final step of the synthesis protocol of Scheme IV is by means of reacting a compound of the formula

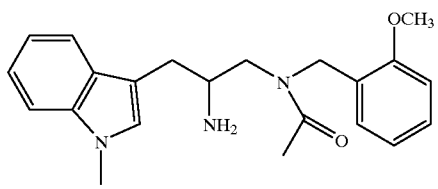

with a potassium carboxylate of the formula

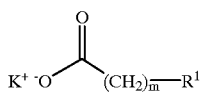

in the presence of isobutylchloroformate and N-methylmorpholine. This reaction is usually performed in the presence of a non-reactive solvent such as methylene chloride at cool temperatures, usually between −30° C. and 10° C., more preferably at temperatures between −20° C. and 0° C. In this reaction equimolar amounts of the two reactants are generally employed although other ratios are operable. An example of this preferred means of acylating the primary amine is shown in the following example.

METHOD P

Preparation of (R)-1-[N-(2-methoxybenzyl)acetylamino]-3-(1H-indol-3-yl)-2-[N-(2-((4-cyclohexyl)piperazin-1-yl)acetyl)amino]propane The title compound was prepared by first cooling 2-((4-cyclohexyl)piperazin-1-yl)acetic acid potassium salt to a temperature between −8° C. and −15° C. in 5 volumes of anhydrous methylene chloride. To this mixture was then added isobutylchloroformate at a rate such that the temperature did not exceed −8° C. This reaction mixture was then stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C.

The following table illustrates many of the compounds produced using essentially the steps described in Schemes I through IV. A person of ordinary skill in the art would readily understand that a certain order of steps must be employed in many instances to avoid reactions other than the one sought. For example, as in the above methods, it is frequently necessary to employ a protecting group in order to block a reaction at a particular moiety.

The abbreviations used in the following table are commonly used in the field and would be readily understood by a practitioner in the field. For example, the abbreviation "Ph" refers to a phenyl group, "i-Pr" refers to an isopropyl group, "Me" describes a methyl group, "Et" refers to an ethyl group, "t-Bu" describes a tert-butyl group, and the like.

In the following table, the first column gives the example number of the compound. The next columns (may be one, two, or three columns) describe the substitution patterns of the particular example. The column entitled "Mp° C." gives the melting point of the compound if it is a solid or notes the form of the substance at ambient temperature. The next column, entitled "MS", defines the mass of the compound as determined by mass spectroscopy. The following column gives the nuclear magnetic resonance profile of the example compound as synthesized. The final columns give the molecular formula of the example compound as well as its elemental analysis.

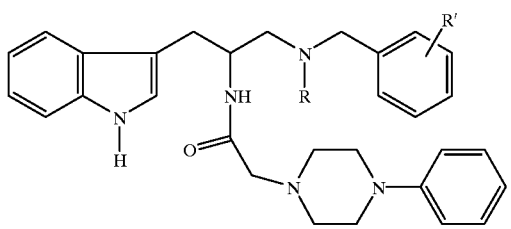

| Example No. | R | R' | Mp ° C. | MS | $^1$H NMR | Formula | Analysis % Theory/Found C | H | N |
|---|---|---|---|---|---|---|---|---|---|
| 1 | H | H | foam | 481 (M$^+$) | CDCl$_3$ 2.28(m, 1H), 2.32–2.45(m, 2H), 2.45–2.61(m, 2H), 2.73(m, 1H), 2.79–3.15 (m, 8H), 3.21(m, 1H), 3.96 (ABq, J=8 Hz, Δv=20 Hz, | C$_{30}$H$_{35}$N$_5$O | 74.81 74.83 | 7.32 7.38 | 14.54 14.67 |

-continued

| | | | | | | | | | |
|---|---|---|---|---|---|---|---|---|---|
| 2 | H | | 2-Cl | foam | 515, 517 (M+'s for Cl isotopes) | DMSO-$d_6$ 2.33–2.50(m, 4H), 2.56–2.75(m, 2H), 2.75–3.09(m, 8H), 3.20(m, 1H), 4.78(s, 2H), 5.21(m, 1H), 6.78(t, J=8 Hz, 1H), 6.88(d, J=8 Hz, 2H), 6.98 (t, J=8 Hz, 1H), 7.06(t, J=8 Hz, 1H), 7.13(m, 1H), 7.13–7.31(m, 4H), 7.34(d, J=7 Hz, 1H), 7.39(dd, J=2, 6 Hz, 1H), 7.50(dd J=2, 7 Hz, 1H), 7.55(d, J=8 Hz, 1H), 7.61(d, J=7 Hz, 1H), 10.81(br s, 1H) 2H), 4.50(m, 1H), 6.78–6.99 (m, 3H), 7.04(m, 1H), 7.10–7.59(m, 11H), 7.66(d, J=8 Hz, 1H), 8.10(br s, 1H) | | | |
| 3 | H | | 2-CF$_3$ | foam | 549 (M+) Exact Mass FAB theory 550.2794 found: 550.2801 | CDCl$_3$ 2.12(m, 1H), 2.36–2.44(m, 2H), 2.44–2.60(m, 2H), 2.77–3.09(m, 10H), 4.02(s, 2H), 4.50(m, 1H), 6.73–7.00(m, 3H), 7.00–7.56 (m, 9H), 7.56–7.85(m, 3H), 8.16(br s, 1H) | C$_{31}$H$_{34}$F$_3$N$_5$O | | |
| 4 | H | | 2-OMe (RS) | foam | 512 (M + 1+) | CDCl$_3$ 2.30–2.43(m, 2H), 2.43–2.54(m, 2H), 2.70–3.10 (m, 11H), 3.82(s, 3H), 3.84 (m, 2H), 4.44(m, 1H), 6.74–6.94(m, 6H), 7.04(m, 1H), 7.07–7.36(m, 7H), 7.64(d, J=8 Hz, 1H), 8.09(br s, 1H) | C$_{31}$H$_{37}$N$_5$O$_2$ | 72.77 7.29 13.69 | 72.49 7.33 13.90 |
| 5 | H | | 2-OMe (R) | foam | 512 (M + 1+) | CDCl$_3$ 2.30–2.43(m, 2H), 2.43–2.56(m, 2H), 2.64–3.12 (m, 11H), 3.59–3.93(m, 2H), 3.82(s, 3H), 4.43(m, 1H), 6.68–6.96(m, 6H), 7.03 (m, 1H), 7.07–7.45(m, 7H), 7.66(d, J=8 Hz, 1H), 8.04 (br s, 1H) | C$_{31}$H$_{37}$N$_5$O$_2$ | 72.77 7.29 13.69 | 72.58 7.39 13.65 |
| 6 | H | | 2-OMe (S) | foam | 512 (M + 1+) | CDCl$_3$ 2.22–2.38(m, 2H), 2.38–2.50(m, 2H), 2.50–3.27 (m, 11H), 3.84(s, 3H), 3.96 (ABq, J=13 Hz, Δv=21 Hz, 2H), 4.27(m, 1H), 6.75–6.97 (m, 6H), 6.99–7.39(m, 8H), 7.63(d, J=8 Hz, 1H), 8.12 (br s, 1H) | C$_{31}$H$_{37}$N$_5$O$_2$ | 72.77 7.29 13.69 | 73.01 7.50 13.69 |
| 7 | H | | 3-OMe | foam | 511 (M+) | CDCl$_3$ 7:3 mixture of amide rotamers 2.20–3.74(m, 14H), 3.74(m, 1H), 3.76(s, 3/10.3H), 3.80(s, 7/10.3H), 4.13(ABq, J=14 Hz, Δv=50 Hz, 7/10.2H), 4.67(m, 1H), 4.70(ABq, J=14 Hz, Δv=160 Hz, 3/10.2H), 6.82–7.00(m, 6H), 7.00–7.45(m, 8H), 7.59 (d, J=8 Hz, 1H), 8.10(br s, 3/10.1H), 8.41(br s, 7/10.1H) | C$_{31}$H$_{37}$N$_5$O$_2$ | 72.77 7.29 13.69 | 73.00 7.19 13.91 |
| 8 | H | | 4-OMe | foam | 511 (M+) | CDCl$_3$ 2.21–2.63(m, 4H), 2.63–2.90(m, 4H), 2.90–3.40 (m, 6H), 3.75(m, 1H), 3.77 (s, 3H), 4.04(ABq, J=12 Hz, Δv=54 Hz, 2H), 4.64 (m, 1H), 6.83–6.95(m, 5H), 6.95–7.48(m, 8H), 7.50–7.75 (m, 2H), 8,23(br s, 1H) | C$_{31}$H$_{37}$N$_5$O$_2$ | 72.77 7.29 13.69 | 72.58 7.35 13.70 |
| 9 | Et | | 2-OMe | foam | 540 (M + 1+) | CDCl$_3$ 1.04(t, J=8 Hz, 3H), 2.32–2.43(m, 2H), 2.43–2.66 (m, 6H), 2.83–2.91(m, 4H), 2.94(d, J=5 Hz, 2H), 3.08 (t, J=6 Hz, 2H), 3.65(ABq, J=14 Hz, Δv=22 Hz, 2H), 3.77(s, 3H), 4.41(q, J=6 Hz, 1H), 6.78–6.96(m, 6H), 7.06–7.29(m, 6H), 7.33(d, | C$_{33}$H$_{41}$N$_5$O$_2$ | 73.44 7.66 12.98 | 73.21 7.63 13.14 |

-continued

| # | R1 | R2 | state | MS | NMR | Formula | C | H | N |
|---|---|---|---|---|---|---|---|---|---|
| | | | | | J=8 Hz, 1H), 7.40(d, J=7 Hz, 1H), 7.64(d, J=8 Hz, 1H), 7.99(br s, 1H) | | | | |
| 10 | MeO(OC)CH₂ | 2-OMe | foam | 584 (M + 1⁺) | CDCl₃ 2.37–2.47(m, 2H), 2.50–2.58(m, 2H), 2.78–2.98 (m, 6H), 3.00(s, 2H), 3.12 (t, J=6 Hz, 2H), 3.37(ABq, J=18 Hz, Δν=26 Hz, 2H), 3.65(s, 3H), 3.77(s, 3H), 3.83(s, 2H), 4.45(m, 1H), 6.80–6.92(m, 5H), 7.00(s, 1H), 7.10–7.40(m, 8H), 7.70 (d, J=9 Hz, 1H), 8.08(s, 1H) | C₃₄H₄₁N₅O₄ | 69.96 69.69 | 7.08 6.98 | 11.99 11.87 |
| 11 | HO(OC)CH₂ | 2-OMe | 95–100 | 570 (M + 1⁺) | DMSO-d₆ 2.31–2.49(m, 4H), 2.75(d, J=8 Hz, 2H), 2.81–3.05(m, 7H), 3.13–3.49 (m, 3H), 3.65–3.80(m, 2H), 3.71(s, 3H), 4.20(m, 1H), 6.78(t, J=8 Hz, 1H), 6.83–6.98(m, 5H), 7.00–7.10(m, 2H), 7.21(t, J=8 Hz, 3H), 7.30(t, J=9 Hz, 2H), 7.56 (br d, J=8 Hz, 2H), 10.81 (br s, 1H) | C₃₃H₃₉N₅O₄ | 69.57 69.80 | 6.90 6.79 | 12.29 11.99 |
| 12 | MeCO | H | foam | 523 (M⁺) | DMSO-d₆ 1:1 mixture of amide rotamers 1.99(s, 1/2.3H), 2.07(s, 1/2.3H), 2.20–2.50(m, 4H), 2.69–2.95 (m, 4H), 2.95–3.12(m, 4H), 3.12–3.52(m, 1/2.1H+1H), 3.63(m, 1/2.1H), 4.40(m, 1H), 4.51(ABq, J=16 Hz, Δν=140 Hz, 1/2.2H), 4.54 (ABq, J=16 Hz, Δν=30 Hz, 1/2.2H), 6.78(t, J=8 Hz, 1H), 6.86–6.94(m, 2H), 6,98 (m, 1H), 7.03–7.15(m, 4H), 7.15–7.38(m, 6H), 7.50–7.60 (m, 1.5H), 7.74(d, J=8 Hz, 1/2.1H), 10.93(br s, 1H) | C₃₂H₃₇N₅O₂ | 73.39 73.67 | 7.12 7.23 | 13.37 13.60 |
| 13 | MeCO | 2-Cl | foam | 557 (M⁺) | DMSO-d₆ 3.2 mixture of amide rotamers 1.93(s, 2/5.3H), 2.09(s, 3/5.3H), 2.25–2.50(m, 4H), 2.70–2.96 (m, 4H), 2.96–3.19(m, 4H), 3.20–3.64(m, 2H), 4.50(m, 1H), 4.59(ABq, J=16 Hz, Δν=70 Hz, 3/5.2H), 4.64(s, 2/5.2H), 6.78(t, J=7 Hz, 1H), 6.91(d, J=8 Hz, 2H), 6.98(t, J=7 Hz, 1H), 7.02–7.10(m, 2H), 7.12(m, 1H), 7.16–7.37(m, 5H), 7.44(m, 1H), 7.50–7.62(m, 2/5.1H+ 1H), 7.75(d, J=8 Hz, 3/5.1H), 10.83(br s, 1H) | C₃₂H₃₆ClN₅O₂ | 68.86 69.06 | 6.50 6.48 | 12.55 12.56 |
| 14 | MeCO | 2-Me | | 538 (M + 1⁺) | CDCl₃ 2.06(s, 3H), 2.21(s, 3H), 2.1–2.6(m, 2H), 2.9–3.3(m, 12H), 3.58(m, 1H), 4.4–4.6(m, 2H), 6.8–7.0(m, 5H), 7.0–7.4(m, 9H), 7.62 (d, J=7 Hz, 1H), 8.15(br s, 1H) | C₃₃H₃₉N₅O₂ | 73.71 74.00 | 7.31 7.37 | 13.02 13.21 |
| 15 | MeCO | 2-CF₃ | foam | 592 (M + 1⁺) | CDCl₃ 2.03(s, 3H), 2.15–2.80(m, 5H), 2.80–3.73(m. 8H), 3.88(m, 1H), 4.47–4.93 (m, 3H), 6.72–7.03(m, 4H), 7.03–7.45(m, 7H), 7.45–7.76 (m, 4H), 8.22(br s, 1H) | C₃₃H₃₆F₃N₅O₂ | 66.99 66.83 | 6.13 6.20 | 11.84 12.10 |
| 16 | MeCO | 2-NO₂ | foam | 569 (M + 1⁺) | CDCl₃ 2.05(s, 3H), 2.28(m, 1H), 2.3–2.7(m, 4H), 2.8–3.2(m, 8H), 3.2–3.9(m, 2H), 4.58(m, 1H), 4.97(m, 1H), 6.8–7.0(m, 2H), 7.0–7.5(m, 10H), 7.5–7.7(m, 2H), 8.12(d, J=7 Hz, 1H), 8.15(br s, 1H) | C₃₂H₃₆N₆O₄ | 67.59 67.32 | 6.38 6.35 | 14.78 14.56 |

-continued

| | | | | | | | | |
|---|---|---|---|---|---|---|---|---|
| 17 | MeCO | 2-OMe (RS) | foam | 553 (M+) | DMSO-d₆ 3:2 mixture of amide rotamers 1.97(s, 1.8H), 2.07(s, 1.2H), 2.26–2.50(m, 4H), 2.70–2.96(m, 4H), 2.96–3.16(m, 4H), 3.16–3.65(m, 2H), 3.72(s, 2/5.3H), 3.74(s, 3/5.3H), 4.40(m, 1H), 4.42(ABq, J=18 Hz, Δν=30 Hz, 3/5.2H), 4.46(ABq, J=16 Hz, Δν=62 Hz, 2/5.2H), 6.70–7.03(m, 7H), 7.03–7.13(m, 2H), 7.13–7.29(m, 3H), 7.34(d, J=8 Hz, 1H), 7.49–7.62(m, 3/5H+1H), 7.72(d, J=6 Hz, 2/5H), 10.98(br s, 1H) | C₃₃H₃₉N₅O₃ | 71.58 7.10 12.65<br>71.50 7.18 12.73 |
| 18 | MeCO | 2-OMe (R) | foam | 553 (M+) Exact Mass FAB (M + 1): calc.: 554.3131 found:. 554.3144 | CDCl₃ 2.11(s, 3H), 2.41–2.43(m, 2H), 2.50–2.55(m, 2H), 2.87–3.18(m, 9H), 3.78(s, 3H), 4.02(dd, J=10, 14 Hz, 1H), 4.51(ABq, J=17 Hz, Δν=42 Hz, 2H), 4.59(m, 1H), 6.80–6.98(m, 6H), 7.07–7.45(m, 8H), 7.68(d, J=8 Hz, 1H), 8.14(s, 1H) | C₃₃H₃₉N₅O₃ | 71.58 7.10 12.65<br>72.19 7.25 12.93 |
| 19 | MeCO | 2-OMe (S) | foam | 553 (M+) | DMSO-d₆ 3:2 mixture of amide rotamers 1.97(s, 3/5.3), 2.07(s, 2/5.3), 2.23–2.60(m, 4H), 2.71–2.95(m, 4H), 2.95–3.17(m, 4H), 3.17–3.80(m, 2H), 3.71(s, 3/5.2H), 3.74(s, 3/5.3H), 4.26(m, 1H), 4.44(ABq, J=16 Hz, Δν=26 Hz, 3/5.2H), 4.45(ABq, J=16 Hz, Δν=60 Hz, 2/5.2H), 6.70–7.02(m, 7H), 7.02–7.12(m, 2H), 7.12–7.30(m, 3H), 7.34(d, J=8 Hz, 1H), 7.56(d, J=10 Hz, 3/5H+1H), 7.70(d, J=10 Hz, 2/5.1H), 10.82(br s, 1H) | C₃₃H₃₉N₅O₃ | 71.58 7.10 12.65<br>71.62 7.28 12.38 |
| 20 | MeCO | 3-F | 86–88 | 541 (M+) | CDCl₃ 2.09(s, 3H), 2.23(m, 1H), 2.3–2.7(m, 2H), 2.7–3.2(m, 8H), 3.30(m, 1H), 3.60(m, 1H), 4.02(m, 1H), 4.2–4.7(m, 3H), 6.7–7.0(m, 6H), 7.0–7.5(m, 8H), 7.66(d, J=7 Hz, 1H), 8.16(br s, 1H) | | |
| 21 | MeCO | 3-OMe | foam | 553 (M+) | CDCl₃ 2.08(s, 3H), 2.15–2.63(m, 4H), 2.72–3.27(m, 8H), 3.75(m, 1H), 3.78(s, 3H), 4.04(m, 1H), 4.51 (ABq, J=16 Hz, Δν=46 Hz, 2H), 4.56(m, 1H), 6.60–6.70(m, 2H), 6.72–6.94(m, 5H), 7.04–7.46(m, 7H), 7.65(d, J=8 Hz, 1H), 8.04(br s, 1H) | C₃₃H₃₉N₅O₃ | 71.58 7.10 12.65<br>71.32 7.01 12.65 |
| 22 | MeCO | 4-OMe | foam | 553 (M+) | DMSO-d₆ 1:1 mixture of amide rotamers 2.01(s, 1/2.3H), 2.05(s, 1/2.3H), 2.23–2.60(m, 4H), 2.74–3.30(m, 8H), 3.69(m, 1H), 3.72(s, 1/2.3H), 3.74(s, 1/2.3H), 4.23(ABq, J=16 Hz, Δν=42 Hz, 1/2.2H), 4.52(m, 1H), 4.36(ABq, J=14 Hz, Δν=164 Hz, 1/2.2H), 6.70–7.16(m, 10H), 7.24(m, 2H), 7.35(m, 1H), 7.55(m, 1/2.1H+1H), 7.73(m, 1/2.1H), 10.84(br s, 1H) | C₃₃H₃₉N₅O₃ | 71.58 7.10 12.65<br>71.85 7.24 12.65 |
| 23 | MeCO | 4-SMe | dec 138 | 569 (M+) | CDCl₃ 2.09(s, 3H), 2.1–2.6(m, 3H), 2.46(s, 3H), 2.8–3.1(m, 8H), 3.30(m, 1H), 3.55(m, 1H), 3.98(m, 1H), | C₃₃H₃₉N₅O₂S | 69.57 6.90 12.29<br>69.86 6.93 12.33 |

-continued

| | | | | | | |
|---|---|---|---|---|---|---|
| | | | | 4.47(ABq, J=12 Hz, Δν=52 Hz, 2H), 4.58(m, 1H), 6.8–6.9(m, 3H), 6.95(d, J=8 Hz, 2H), 7.0–7.4(m, 9H), 7.66(d, J=8 Hz, 1H), 8.08 (br s, 1H) | | |
| 24 | HCO | 2-OMe | foam 540 (M + 1) | CDCl$_3$ 2.33–2.47(m, 2H), 2.50–2.65(m, 2H), 2.87–3.10 (m, 9H), 3.75(s, 3H), 3.77 (m, 1H), 4.40(ABq, J=15 Hz, Δν=35 Hz, 2H), 4.65 (m, 1H), 6.75–6.95(m, 6H), 7.08–7.42(m, 8H), 7.67(d, J=9 Hz, 1H), 8.20(br s, 1H), 8.33(s, 1H) | C$_{32}$H$_{37}$N$_5$O$_3$ | 71.21 6.91 12.98<br>70.99 6.96 13.25 |
| 25 | BrCH$_2$CO | 2-OMe | foam 631, 638 (M$^{+}$'s for Br isotopes) Exact Mass FAB (M + 1): calc.: 632.2236 found:. 632.2213 | CDCl$_3$ 2.37–2.47(m, 2H), 2.53–2.63(m, 2H), 2.90–3.17 (m, 8H), 3.80(s, 3H), 3.95–4.13(m, 2H), 3.98(ABq, J=11 Hz, Δν=61 Hz, 2H), 4.57(ABq, J=18 Hz, Δν=80 Hz, 2H), 4.67(m, 1H), 6.78 (d, J=5 Hz, 1H), 6.80–6.90 (m, 4H), 7.07(d, J=3 Hz, 1H), 7.10–7.30(m, 6H), 7.37 (d, J=8 Hz, 1H), 7.50(d, J=10 Hz, 1H), 7.70(d, J=9 Hz, 1H), 8.07(s, 1H) | C$_{33}$H$_{38}$BrN$_5$O$_3$ | |
| 26 | EtCO | 2-OMe | oil 568 (M + 1$^+$) | CDCl$_3$ 1.12(t, J=9 Hz, 3H), 2.38(q, J=9 Hz, 2H), 2.33–2.60(m, 4H), 2.83–3.13(m, 8H), 3.22(br d, J=13 Hz, 1H), 3.80(s, 3H,), 4.03(br t, J=13 Hz, 1H), 4.55(ABq, J=20 Hz, Δν=40 Hz, 2H), 4.60(m, 1H), 6.83–6.97(m, 6H), 7.10–7.57(m, 8H), 7.68 (d, J=8 Hz, 1H), 8.24(br s, 1H) | C$_{34}$H$_{41}$N$_5$O$_3$ | 71.93 7.28 12.34<br>72.17 7.42 12.10 |
| 27 | PhCO | 2-OMe | foam 615 (M$^+$) | CDCl$_3$ 2.28–2.57(m, 4H), 2.77–3.17(m, 9H), 3.65(s, 3H), 4.22(t, J=13 Hz, 1H), 4.60(ABq, J=15 Hz, Δν=30 Hz, 2H), 4.82(m, 1H), 6.70–6.92(m, 5H), 7.02–7.55(m, 14H), 7.68(d, J=7 Hz, 1H), 8.22(br s, 1H) | C$_{38}$H$_{41}$N$_5$O$_3$ | 74.12 6.71 11.37<br>74.88 6.87 11.32 |
| 28 | EtOCO | 2-OMe | foam 584 (M + 1) | DMSO-d$_6$ 1.05(t, J=8 Hz, 3H), 2.31–2.45(m, 4H), 2.73–2.90(m 4H), 2.93–3.10 (m 4H), 3.22–3.48(m, 2H), 3.66(s, 3H), 3.87–4.03(m, 2H), 4.26–4.55(m, 3H), 6.77 (t, J=7 Hz, 1H), 6.80–7.00 (m, 6H), 7.05(t, J=8 Hz, 1H), 7.11(br s, 1H), 7.20(t, J=9 Hz, 3H), 7.32(d, J=10 Hz, 1H), 7.52(br d, J=6 Hz, 2H) | C$_{34}$H$_{41}$N$_5$O$_4$ | 69.96 7.08 12.00<br>69.85 7.19 11.98 |
| 29 | MeNHCO | 2-OMe | oil 568 (M$^+$) | DMSO-d$_6$ 2.32–2.46(m, 4H), 2.55(d, J=5 Hz, 3H), 2.78–2.90(m, 4H), 2.96–3.10 (m, 4H), 3.18(dd, J=5, 14 Hz, 1H), 3.44(dd, J=8, 13 Hz, 1H), 3.70(s, 3H), 4.30 (m, 1H), 4.37(ABq, J=18 Hz, Δν=42 Hz, 2H), 6.32(br d, J=5 Hz, 1H), 6.77(t, J=7 Hz, 1H), 6.82–7.00(m, 6H), 7.05(t, J=8 Hz, 1H), 7.11 (d, J=3 Hz, 1H), 7.16–7.25 (m, 3H), 7.32(d, J=9 Hz, 1H), 7,53(d, J=8 Hz, 1H), 7.61(d, J=9 Hz, 1H), 10.82 (br s, 1H) | C$_{33}$H$_{40}$N$_6$O$_3$ | 69.69 7.09 14.78<br>69.94 7.13 14.83 |
| 30 | MeO(OC)CH$_2$CO | 2-OMe | foam 611 (M$^+$) | CDCl$_3$ 2.37–2.47(m, 2H), 2.50–2.60(m, 2H), 2.82–3.18 (m, 9H), 3.57(s, 2H), 3.72 (s, 3H), 3.78(s, 3H), 4.02 | C$_{35}$H$_{41}$N$_5$O$_5$ | 68.72 6.76 11.45<br>68.44 6.76 11.44 |

| No. | | | | | NMR | Formula | C | H | N |
|---|---|---|---|---|---|---|---|---|---|
| | | | | | (dd, J=10, 14 Hz, 1H), 4.47 (ABq, J=20 Hz, Δν=40 Hz, 2H), 4.60(m, 1H), 6.77–6.92 (m, 6H), 7.03–7.30(m, 6H), 7.37(d, J=7 Hz, 1H), 7.45 (d, J=10 Hz, 1H), 7.68(d, J=9 Hz, 1H), 8.12(s, 1H) | | | | |
| 31 | HO(OC)CH$_2$CO | 2-OMe | 103–107 | 598 (M + 1$^+$) Exact Mass FAB (M + 1): calc.: 598.3029 found:. 598.3046 | CDCl$_3$ 2.68–2.90(m, 4H), 2.90–3.37(m, 9H), 3.57(br s, 2H), 3.78(s, 3H), 3.93(t, J=12 Hz, 1H), 4.53(ABq, J=17 Hz, Δν=47 Hz, 2H), 4.70(m, 1H), 6.77–6.97(m, 6H), 7.07–7.33(m, 7H), 7.37 (d, J=8 Hz, 1H), 7.63(d, J=8 Hz, 1H), 7.85(br s, 1H), 8.33(br s, 1H) | C$_{34}$H$_{39}$N$_5$O$_5$ | | | |
| 32 | Me(CO)OCH$_2$CO | 2-OMe | foam | 612 (M + 1$^+$) | CDCl$_3$ 2.10(s, 3H), 2.35–2.43(m, 2H), 2.47–2.57(m, 2H), 2.90–3.13(m, 9H), 3.80 (s, 3H), 4.03(dd, J=10, 15 Hz, 1H), 4.40(ABq, J=19 Hz, Δν=30 Hz, 2H), 4.57 (m, 1H), 4.85(ABq, J=15 Hz, Δν=19 Hz, 2H), 6.75–6.90(m, 6H), 7.03(d, J=2 Hz, 1H), 7.10–7.30(m, 5H), 7.35–7.43(m, 2H), 7.66(d, J=9 Hz, 1H), 8.32(br s, 1H) | C$_{35}$H$_{41}$N$_5$O$_5$ | 68.72 68.50 | 6.76 6.86 | 11.45 11.20 |
| 33 | HOCH$_2$CO | 2-OMe | foam | 569 (M$^+$) | CDCl$_3$ 2.35–2.57(m, 2H), 2.80–3.17(m, 9H), 3.52(t, J=5 Hz, 1H), 3.75(s, 3H), 4.08(m, 1H), 4.27(dd, J=5, 10 Hz, 2H), 4.33(d, J=5 Hz, 2H), 4.63(m, 1H), 6.73–6.92 (m, 6H), 7.03(d, J=3 Hz, 1H), 7.12–7.32(m, 5H), 7.33–7.40(m, 2H), 7.67(d, J=10 Hz, 1H), 8.07(br s, 1H) | C$_{33}$H$_{39}$N$_5$O$_4$·0.5 H$_2$O | 68.49 68.51 | 6.97 6.86 | 12.10 11.91 |
| 34 | H$_2$NCH$_2$CO | 2-OMe | foam | 568 (M$^+$) | CDCl$_3$ 2.20(m, 2H), 2.35–2.45(m, 2H), 2.45–2.53(m, 2H), 2.80–3.07(m, 8H), 3.30 (dd, J=5, 15 Hz, 1H), 3.47–3.57(m, 2H), 3.77(s, 3H), 3.93(dd, J=10, 15 Hz, 1H), 4.42(ABq, J=20 Hz, Δν=30 Hz, 2H), 4.62(m, 1H), 6.77–6.90(m, 5H), 7.03–7.40(m, 9H), 7.65(d, J=8 Hz, 1H), 8.12(br s, 1H) | C$_{33}$H$_{40}$N$_6$O$_3$ | 69.69 69.82 | 7.09 7.14 | 14.78 14.49 |
| 35 | Me$_2$NCH$_2$CO | 2-OMe | foam | 596 (M$^+$) | CDCl$_3$ 2.30(s, 6H), 2.32–2.50(m, 4H), 2.87–3.05(m, 8H), 3.20(s, 2H), 3.33(dd, J=6, 9 Hz, 1H), 3.78(s, 3H), 3.85(m, 1H), 4.58(m, 1H) 4.65(ABq, J=18 Hz, Δν=42 Hz, 2H), 6.81–6.93 (m, 6H), 7.10–7.40(m, 8H), 7.65(d, J=11 Hz, 1H), 8.17 (br s, 1H) | C$_{35}$H$_{44}$N$_6$O$_3$ | 70.44 70.15 | 7.43 7.39 | 14.08 14.02 |
| 36 | t-Bu-O(CO)NH—CH$_2$CO | 2-OMe | foam | 668 (M$^+$) | CDCl$_3$ 1.43(s, 9H), 2.33–2.57(m, 4H), 2.82–3.12(m, 8H), 3.17(dd, J=5, 15 Hz, 1H), 3.77(s, 3H), 3.93–4.10 (m, 3H), 4.42(ABq, J=18 Hz, Δν=41 Hz, 2H), 4.60 (m, 1H), 5.50(br s, 1H), 6.73–6.92(m, 6H), 7.05(s, 1H), 7.08–7.32(m, 5H), 7.35 (d, J=10 Hz, 2H), 7.65(d, J=10 Hz, 1H), 8.10(br s, 1H) | C$_{38}$H$_{48}$N$_6$O$_5$ | 68.24 68.44 | 7.23 7.50 | 12.57 12.61 |

-continued

| | | | | | | | | | | |
|---|---|---|---|---|---|---|---|---|---|---|
| 37 | MeSO$_2$ | | 2-OMe | foam | 589 (M$^+$) | DMSO-d$_6$ 2.28–2.46(m, 4H), 2.83(d, J=7 Hz, 4H), 2.90(s, 3H), 2.98–3.04(m, 4H), 3.26–3.34(m, 2H), 3.67 (s, 3H), 4.30(m, 1H), 4.36 (d, J=5 Hz, 2H), 6.77(t, J=8 Hz, 1H), 6.84–6.92(m, 3H), 6.92–7.00(m, 2H), 7.08–7.09(m, 2H), 7.18–7.30 (m, 4H), 7.33(d, J=8 Hz, 1H), 7.46(d, J=8 Hz, 1H), 7.54(d, J=9 Hz, 1H), 10.82 (br s, 1H) | C$_{32}$H$_{39}$N$_5$O$_4$S | 65.17 64.88 | 6.67 6.72 | 11.88 11.60 |

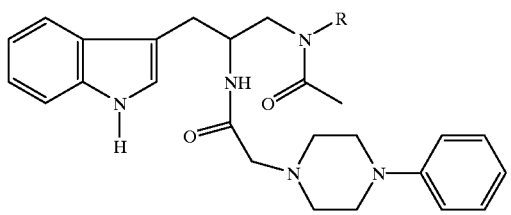

| Example No. | R | Mp °C. | MS | $^1$H NMR | Formula | Analysis Theory/Found | | |
|---|---|---|---|---|---|---|---|---|
| | | | | | | C | H | N |
| 38 | Me | 128–129 | 447 (M$^+$) | CDCl$_3$ 2.07(s, 3H), 2.38–2.78(m, 3H), 2.8–3.3(m, 11H), 3.42(m, 1H), 3.67(m, 1H), 3.95(m, 1H), 4.58(m, 1H), 6.8–7.0 (m, 3H), 7.1–7.4(m, 7H), 7.68(d, J=7 Hz, 1H), 8.21(br s, 1H) | C$_{26}$H$_{33}$N$_5$O$_2$ | 69.77 69.59 | 7.43 7.52 | 15.65 15.65 |
| 39 | n-Bu | foam | 489 (M$^+$) | $^1$H CDCl$_3$ 0.88(t, J=6 Hz, 3H), 1.1–1.40 (m, 2H), 1.4–1.6(m, 2H), 2.08(s, 3H), 2.2–2.4(m, 4H), 2.8–3.1(m, 8H), 3.1–3.4 (m, 3H), 3.9(m, 1H), 4.5(br s, 1H), 6.8–7.0(m, 3H), 7.0–7.5(m, 7H), 7.68(d, J=6 Hz, 1H), 8.31(br s, 1H). | C$_{29}$H$_{39}$N$_5$O$_2$ | 71.13 71.40 | 8.03 8.05 | 14.30 14.41 |
| 40 | n-Hex | foam | 517 (M$^+$) | $^1$H CDCl$_3$ 0.82–0.92(m, 3H), 1.12–1.36 (m, 6H), 1.40–1.70(m, 3H), 2.05(s, 3H), 2.31–2.61(m, 3H), 2.80–3.11(m, 8H), 3.11–3.42(m, 3H), 3.9(m, 1H), 4.5(m, 1H), 6.75–6.98(m, 3H), 7.08–7.48(m, 7H), 7.7(m, 1H), 8.1(br s, 1H). | C$_{31}$H$_{43}$N$_5$O$_2$ | 71.92 71.85 | 8.37 8.35 | 13.53 13.59 |
| 41 | (c-hexyl)CH$_2$ | foam | 530 (M + 1$^+$) | CDCl$_3$ 0.65–1.02(m, 2H), 1.02–1.36(m, 3H), 1.36–1.87(m, 9H), 2.07(s, 3H), 2.15–3.70 m, 12H), 3.95(m, 1H), 4.57(m, 1H), 6.70–7.03(m, 4H), 7.03–7.23(m, 4H), 7.31–7.44(m, 2H), 7.69(d, J=10 Hz, 1H), 8.16(br s, 1H) | C$_{32}$H$_{43}$N$_5$O$_2$ | 72.56 72.46 | 8.18 8.12 | 13.22 13.07 |
| 42 | Ph | 183–184 | 509 (M$^+$) | $^1$H DMSO 1.71(s, 3H), 2.23–2.43(m, 4H), 2.71–2.94(m, 4H), 2.94–3.10(m, 4H), 3.61(m, 1H), 4.03(m, 1H), 4.24(m, 1H), 6.77(t, J=8 Hz, 1H), 6.92–6.99(m, 3H), 6.99–7.12(m, 2H), 7.21(t, J=8 Hz, 2H), 7.24–7.35(m, 3H), 7.4(m, 1H), 7.40–7.54(m, 4H), 10.92(br s, 1H). | C$_{31}$H$_{35}$N$_5$O$_2$ | 73.04 73.30 | 6.92 7.11 | 13.74 13.73 |
| 43 | PhCH$_2$CH$_2$ | | 537 (M$^+$) | $^1$H DMSO (3:2 mixture of amide rotamers) 1.69(s, 3/5.3H), 2.00(s, 2/5.3H), 2.50–2.60(m, 5H), 2.70–3.05(m, 5H), 3.05–3.19(m, 4H), 3.19–3.36(m, 2H), 3.36–3.64(m, 2H), 4.32(m, 1H), 6.76 (t, J=8 Hz, 1H), 6.90(d, J=8 Hz, 2H), 6.95–7.39(m, 11H), 7.56(m, 1H), 7.76 (m, 2/5.1H), 7.92(m, 3/5.1H), 10.81(br s, 2/5.1H), 10.85(br s, 3/5.1H). | C$_{33}$H$_{39}$N$_5$O$_2$ | 73.71 73.95 | 7.31 7.45 | 13.02 13.07 |

-continued

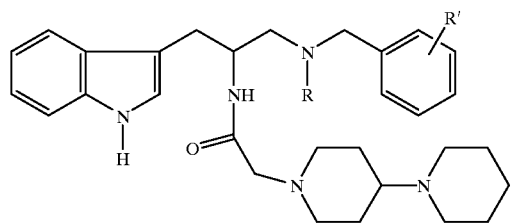

| Example No. | R | R' | Mp °C. | MS | ¹H NMR | Formula | Analysis % Theory/Found | | |
|---|---|---|---|---|---|---|---|---|---|
| | | | | | | | C | H | N |
| 44 | H | 2-OMe (R) | foam | 517 (M⁺) | CDCl₃ 1.10–2.18 (m, 12H), 2.18–3.18(m, 14H), 3.61–3.95(m, 2H), 3.93(s, 3H), 4.36 (m, 1H), 6.76–6.96 (m, 3H), 7.04–7.44 (m, 5H), 7.42(d, J=8 Hz, 1H), 7.65 (d, J=8 Hz, 1H), 9.13(br s, 1H) | $C_{31}H_{43}N_5O_2$ | 71.92 71.69 | 8.37 8.25 | 13.53 13.26 |
| 45 | H | 2-OMe (S) | foam | 517 (M⁺) | CDCl₃ 1.13–2.18 (m, 12H), 2.18–3.33(m, 14H), 3.61–3.96(m, 2H), 3.85(s, 3H), 4.36 (m, 1H), 6.80–6.97 (m, 3H), 6.97–7.36 (m, 6H), 7.44(d, J=8 Hz, 1H), 9.60 (br s, 1H) | $C_{31}H_{43}N_5O_2$ | 71.92 71.91 | 8.37 8.25 | 13.53 13.42 |
| 46 | MeCO | H | foam | 530 (M + 1⁺) | CDCl₃ 3:1 mixture of amide rotamers 1.21–1.69(m, 10H), 1.90–2.19(m, 3H), 2.07(s, 3/4.3H), 2.10(s, 1/4.3H), 2.37–2.55(m, 5H), 2.65–3.18(m, 6H), 4.02(dd, J=13 Hz, J=10 Hz, 1H), 4.50(ABq, J=17 Hz, Δν=52 Hz, 3/4.2H), 4.67(ABq, J=17 Hz, Δν=228 Hz, 1/4.2H), 4.55(m, 1H), 6.94–7.44(m, 10H), 7.65(d, J=8 Hz, 3/4.1H), 7.53(d, J=8 Hz, 1/4.1H), 8.08(br s, 3/4.1H), 8.22 (br s, 1/4.1H). | $C_{32}H_{43}N_5O_2$ | 72.56 72.36 | 8.18 8.17 | 13.22 13.12 |
| 47 | MeCO | 2-Cl (RS) | foam | 563 (M⁺) Exact Mass FAB theory 564.3105 found: 564.3130 (M⁺¹) | CDCl₃ 1.17–1.80(m, 10H), 1.90–2.27(m, 3H), 2.03(s, 3H), 2.35–2.59(m, 5H), 2.67–3.23,(m, 6H), 3.97(dd, J=10, 15 Hz, 1H), 4.53 (m, 1H), 4.58(ABq, J=17 Hz, Δν=21 Hz, 2H), 6.95–7.29(m, 6H), 7.34(d, J=8 Hz, 2H), 7.42(d, J=9 Hz, 1H), 7.63(d, J=8 Hz, 1H), 8.19(br s, 1H) | $C_{32}H_{42}ClN_5O_2$ | | | |
| 48 | MeCO | 2-Cl (R) | foam | 563 (M⁺) | ¹H CDCl₃ 1.1–1.8(m, 10H), 1.8–2.3(m, 4H), 2.04(s, 3H), 2.4–2.6 (m, 3H), 2.6–2.8(m, 2H), 2.8–2.9 (m, 2H), 2.9–3.1(m, 2H), 3.2(m, 1H), 3.9(m, 1H), 4.5–4.7(m, 3H), 7.0–7.6(m, 9H), 7.62(d, J=6 Hz, 1H), 8.32(br s, 1H). | $C_{32}H_{42}ClN_5O_2$ | 68.13 68.20 | 7.50 7.60 | 12.41 12.17 |
| 49 | MeCO | 2-Cl (S) | foam | 563 (M⁺) | ¹H CDCl₃ 1.3–1.8(m, 6H), 2.04 (s, 3H), 1.8–2.1(m, 3H), 2.1–2.3 (m, 3H), 2.4–2.6(m, 5H), 2.7–2.8 (m, 2H), 2.86(d, J=2 Hz, 2H), 2.9–3.1(m,2H), 3.2(m, 1H), 3.9(m, 1H), 4.5–4.7(m, 3H), 7.0–7.5(m, 9H), 7.63(d, J=7 Hz, 1H), 8.38(br s, 1H) | $C_{32}H_{42}ClN_5O_2$ | 68.13 68.40 | 7.50 7.61 | 12.41 12.60 |
| 50 | MeCO | 2-OMe (RS) | foam | 559 (M⁺) | CDCl₃ 1.30–1.86(m, 10H), 1.93–2.32(m, 3H), 2.10(s, 3H), 2.45–2.67(m, 4H), 2.71–3.18(m, 5H), 2.87(s, 2H), 3.76(s, 3H), 3.99(dd, J=14 Hz, J=10 Hz, 1H), 4.49, | $C_{33}H_{45}N_5O_3$ | 70.81 70.95 | 8.10 8.05 | 12.51 12.45 |

-continued

| | | | | | | | | |
|---|---|---|---|---|---|---|---|---|
| 51 | MeCO | 2-OMe (R) | 559 (M + 1⁺) | (ABq, J=17 Hz, Δv=41 Hz, 2H), 4.55(m, 1H), 6.79–6.93(m, 3H), 7.06–7.27(m, 4H), 7.36(d, J=8 Hz, 1H), 7.45(d, J=9 Hz, 1H), 7.66(d, J=8 Hz, 1H), 8.28(br s, 1H) DMSO-$d_6$ 3:2 mixture of amide rotamers, 1.25–1.70(m, 10H), 1.77–2.00(m, 2H), 1.95 (s, 3/5.3HH), 2.04(s, 2/5.3HH), 2.10–2.97 (m, 9H), 3.10–3.65(m, 3H), 3.72(s, 2/5.3HH), 3.74(s, 3/5.3HH), 4.26–4.58(m, 3H), 6.76–7.12(m, 6H), 7.13–7.35(m, 2H), 7.42–7.66(m, 2H), 10.80(br s, 1H) | $C_{33}H_{45}N_5O_3$ | 70.81 70.57 | 8.10 8.05 | 12.51 12.39 |
| 52 | MeCO | 2-OMe (S) | 559 (M + 1⁺) | DMSO-$d_6$ 3:2 mixt. of amide rotamers, 1.15–1.68(m, 10H), 1.68–2.20(m, 3H), 1.95 (s, 3/5.3HH), 2.04(s, 2/5.3HH), 2.20–3.00 (m, 9H), 3.00–3.65(m, 3H), 3.74(s, 2/5.3HH), 3.76(s, 3/5.3HH), 4.20–4.60(m, 3H), 6.75–7.15(m, 6H), 7.15–7.40(m, 2H), 7.40–7.68(m, 2H), 10.78(br s, 1H) | $C_{33}H_{45}N_5O_3$ | 70.81 71.01 | 8.10 8.39 | 12.51 12.63 |

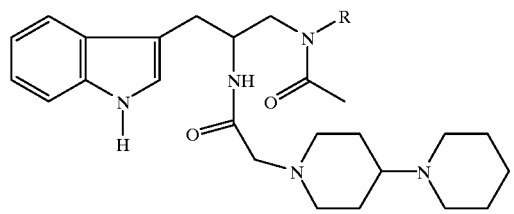

| Example No. | R | Mp °C. | MS | ¹H NMR | Formula | Analysis Theory/Found | | |
|---|---|---|---|---|---|---|---|---|
| | | | | | | C | H | N |
| 53 | Ph | 140–141 | 515 (M⁺) | ¹H DMSO 1.21–1.58(m, 10H), 1.70(s, 3H), 1.87(ABq, J=8 Hz, Δv=20 Hz, 2H), 2.04(m, 1H), 2.29–2.49(m, 4H), 2.45–2.64(m, 2H), 2.63–2.79(m, 2H), 2.79–2.95(m, 2H), 3.58(m, 1H), 4.02(t, J=12 Hz, 1H), 4.20(m, 1H), 6.93(t, J=8 Hz, 1H), 6.98–7.11(m, 2H), 7.17–7.53(m, 8H), 10.91(br s, 1H). | $C_{31}H_{41}N_5O_2$ | 72.20 71.98 | 8.01 8.07 | 13.58 13.53 |
| 54 | PhCH₂CH₂ | foam | 543 (M⁺) | ¹H DMSO (3:2 mixture of amide rotamers) 1.23–1.57(m, 10H), 1.75–1.97 (m, 2H), 1.84(s, 3/5.3H), 1.93(s, 2/5.3H), 2.05(m, 1H), 2.23–2.47(m, 4H), 2.50–2.77(m, 6H), 2.77–2.95(m, 2H), 3.20–3.35(m, 1H), 3.36–3.52(m, 2H), 3.62(m, 1H), 4.39(m, 1H), 6.97 (m, 1H), 7.02–7.31(m, 7H), 7.34(d, J=8 Hz, 1H), 7.45(d, J=8 Hz, 3/5H), 7.53–7.67(m, 2/5.1H+1H), 10.84(br s, 1H). | $C_{33}H_{45}N_5O_2$ | 72.89 72.60 | 8.34 8.29 | 12.88 12.64 |

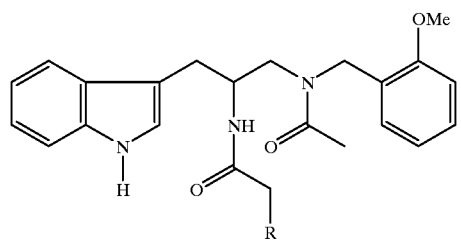

| Example No. | R | Mp °C. | MS | ¹H NMR | Formula | Analysis Theory/Found | | |
|---|---|---|---|---|---|---|---|---|
| | | | | | | C | H | N |
| 55 | Br (R) | foam | 473 (M⁺) | CDCl₃ 2.15(s, 3H), 2.81–2.96(m, 2H), 3.15(ABq, J=4.3 Hz, Δv=14.6 Hz, 1H), 3.72(s, 3H), 3.79(s, 2H), 4.06–4.15(m, 1H), 4.30(m, 1H), 4.38(ABq, J=16.7 Hz, Δv=49.0 Hz, 2H), 6.72–6.81(m, 3H), 7.01(s, 1H), 7.13–7.30(m, 3H), 7.35– | $C_{23}H_{26}N_3O_{32}Br$ | 58.48 58.69 | 5.55 5.66 | 8.90 8.94 |

-continued

| | | | | | | | | |
|---|---|---|---|---|---|---|---|---|
| 56 | PhO | foam | 485 (M+) | CDCl₃ 2.00(s, 3H), 2.86(dd, J=8, 14 Hz, 1H), 3.01(dd, J=5, 14 Hz, 1H), 3.20(dd, J=5, 15 Hz, 1H), 3.70(s, 3H), 4.04(dd, J=10, 14 Hz, 1H), 4.34(ABq, J=18 Hz, Δv=44 Hz, 2H), 4.44(ABq, J=15 Hz, Δv=25 Hz, 2H), 4.42(m, 1H), 6.70–6.85(m, 3H), 6.85–7.06(m, 4H), 7.06–7.45(m, 6H), 7.54(m, 1H), 7.71(d, J=8 Hz, 1H), 7.97(br s, 1H) | C₂₉H₃₁N₃O₄ | 71.73 6.43 8.65 | 71.48 6.59 8.46 |
| 57 | PhS | foam | 501 (M+) | CDCl₃ 1.92(s, 3H), 2.76(dd, J=8, 14 Hz, 1H), 2.92(dd, J=4, 14 Hz, 1H), 3.06(dd, J=4, 14 Hz, 1H), 3.57(s, 2H), 3.69(s, 3H), 3.99(dd, J=8, 14 Hz, 1H), 4.29(ABq, J=16 Hz, Δv=44 Hz, 2H), 4.36(m, 1H), 6.65(m, 3H), 6.85(d, J=3 Hz, 1H), 7.05–7.37(m, 9H), 7.42 (m, 1H), 7.67(d, J=8 Hz, 1H), 7.85(br s, 1H) | C₂₉H₃₁N₃O₃S | 69.44 6.23 8.38 | 69.55 6.49 8.10 |
| 58 | PhNHCH₂CH₂NH | foam | 528 (M +1+) | CDCl₃ 2.11(s, 3H), 2.72–2.95 (m, 4H), 3.00–3.34(m, 6H), 3.72(s, 3H), 4.14(dd, J=11, 13 Hz, 1H), 4.40(ABq, J=17 Hz, Δv=63 Hz, 2H), 4.42(m, 1H), 4.78(br s, 1H), 6.65–6.84(m, 6H), 6.95(d, J=3 Hz, 1H), 7.07–7.35(m, 6H), 7.67 (d, J=8 Hz, 1H), 7.80–7.91(m, 2H). | C₃₁H₃₇N₅O₃ | 70.56 7.07 13.27 | 70.35 7.03 13.06 |
| 59 | 1-pyrrolidinyl | foam | 463 (M + 1+) | CDCl₃ 1.66–1.74(m, 4H), 2.11(s, 3H), 2.47(J=19 Hz, 4H), 2.86–3.17(m, 5H), 3.74(s, 3H), 4.00(dd, J=11, 14 Hz, 1H), 4.46(ABq, J=17 Hz, Δv=46 Hz, 2H), 4.52(br s, 1H), 6.76–6.83(m, 2H), 7.08–7.28(m, 3H), 7.18(s, 1H), 7.35(d, J=8 Hz, 1H), 7.52(d, J=8 Hz, 1H), 7.69(d, J=8 Hz, 1H), 8.38(br s, 1H) | C₂₇H₃₄N₄O₃ | 70.10 7.41 12.11 | 70.42 7.29 11.75 |
| 60 | 1-piperidinyl | foam | 476 (M+) | CDCl₃ 1.37–1.56(m, 6H), 2.09(s, 3H), 2.30(br s, 4H), 280–3.19(m, 5H), 3.75(s, 3H), 3.95(dd, J=11, 13 Hz, 1H), 4.46(ABq, J=17 Hz, Δv=44 Hz, 2H), 4.53(m, 1H), 6.75–6.88(m, 3H), 7.04–7.24 (m, 5H), 7.34(d, J=8 Hz, 1H), 7.68(d, J=7 Hz, 1H), 8.04(br, 1H) | C₂₈H₃₆N₄O₃ | 70.56 7.61 11.58 | 70.68 7.70 11.58 |
| 61 | 1-hexamethylene-iminyl | foam | 490 (M+) | CDCl₃ 1.52(br s, 8H), 2.09(s, 3H), 2.54(br s, 4H), 2.87–3.10 (m, 4H), 3.21(dd, J=5, 13 Hz, 1H), 3.76(s, 3H), 3.92(dd, J=10, 13 Hz, 1H), 4.48(ABq, J=17 Hz, Δv=41 Hz, 2H), 4.53 (m, 1H), 6.73–6.89(m, 3H), 7.04–7.25(m, 4H), 7.34(d, J=6 Hz, 1H), 7.58(m, 1H), 7.66(d, J=7 Hz, 1H), 8.04(br s, 1H) | C₂₉H₃₈N₄O₃ | 70.99 7.81 11.42 | 71.27 7.98 11.39 |
| 62 | 4-morpholinyl | foam | 478 (M+) | CDCl₃ 2.07(s, 3H), 2.20–2.29 (m, 2H), 2.31–2.41(m, 2H), 2.85–2.97(m, 3H), 3.01–3.13 (m, 2H), 3.46–3.67(m, 4H), 3.77(s, 3H), 4.15(dd, J=10, 13 Hz, 1H), 4.47(ABq, J=17 Hz, Δv=48 Hz, 2H), 4.52(m, 1H), 6.77–6.89(m, 3H), 7.02–7.28(m, 4H), 7.36(d, J=6 Hz, 1H), 7.46(d, J=8 Hz, 1H), 7.68(d, J=7 Hz, 1H), 8.02(br s, 1H) | C₂₇H₃₄N₄O₄ | 67.76 7.16 11.71 | 67.54 7.18 11.58 |

| | | | | | | | | |
|---|---|---|---|---|---|---|---|---|
| 63 | 1-indolinyl | foam | 510 (M+) | CDCl₃ 1.85(s, 3H), 2.85–3.41 (m, 7H), 3.60(ABq, J=17 Hz, Δv=42 Hz, 2H), 3.73(s, 3H), 4.00(dd, J=12, 13 Hz, 1H), 4.38(ABq, J=17 Hz, Δv=48 Hz, 2H), 4.43–4.48(m, 1H), 6.32(d, J=8 Hz, 1H), 6.76(m, 3H), 6.97–7.24(m, 7H), 7.35 (d, J=8 Hz, 1H), 7.54(d, J=8 Hz, 1H), 7.70(d, J=8 Hz, 1H), 7.99(br s, 1H) | $C_{31}H_{34}N_4O_3$ | 72.92 73.21 | 6.71 6.54 | 10.97 11.03 |
| 64 | 1,2,3,4-tetrahydroisoquinolin-4-yl | foam | 524 (M+), 525 (M + 1+) | CDCl₃ 2.06(s, 3H), 2.61–3.28 (m, 9H), 3.48–3.94(m, 3H), 3.77(s, 3H), 4.50(ABq J=17 Hz, Δv=36 Hz, 2H), 4.57(m, 1H), 6.78–6.92(m, 4H), 6.98–7.26(m, 8H), 7.34(d, J=9 Hz, 1H), 7.62(d, J=8 Hz, 1H), 7.98(br s, 1H) | $C_{32}H_{36}N_4O_3$ | 73.26 73.31 | 6.92 6.95 | 10.68 10.43 |
| 65 | 1-(4-Ph-piperidinyl) | foam | 552 (M+) | CDCl₃ 1.50–1.91(m, 4H), 2.08(s, 3H), 2.06–2.22(m, 2H), 2.40(m, 1H), 2.64(br d, J=11 Hz, 1H), 2.80(br d, J=12 Hz, 1H), 2.86–2.98(m, 3H), 3.04–3.18(m, 2H), 3.73(s, 3H), 4.01(dd, J=10, 14 Hz, 1H), 4.46(ABq, J=17 Hz,, Δv=45 Hz, 2H), 4.54(m, 1H), 6.76–6.85(m, 3H), 7.02–7.36(m, 10H), 7.54(d, J=8 Hz, 1H), 7.70(d, J=8 Hz, 1H), 8.01(br s, 1H) | $C_{34}H_{40}N_4O_3$ | 73.89 73.69 | 7.30 7.25 | 10.14 10.31 |
| 66 | 1-(4-Me₂N-piperidinyl) | foam | 519 (M+) | CDCl₃ 1.26(m, 1H), 1.48–1.76(m, 3H), 1.90–2.11(m, 3H), 2.09(s, 3H), 2.25(s, 6H), 2.51(br d, J=13 Hz, 1H), 2.73(br d, J=12 Hz, 1H), 2.85(s, 2H), 2.85–3.23 (m, 3H), 3.75(s, 3H), 3.94(dd, J=10, 14 Hz, 1H), 4.47 (ABq, J=17 Hz, Δv=43 Hz, 2H), 4.51(m, 1H), 6.77–6.88(m, 3H), 7.01–7.28(m, 4H), 7.35(d, J=8 Hz, 1H), 7.41(d, J=9 Hz, 1H), 7.66(d, J=7 Hz, 1H), 8.09(br s, 1H) | $C_{30}H_{41}N_5O_3$ | 69.34 69.58 | 7.95 8.01 | 13.48 13.52 |
| 67 | 1-(4-Ph-Δ³-piperidinyl) | foam | 550 (M+) | CDCl₃ 2.12(s, 3H), 2.21–2.70(m, 4H), 2.90–3.25(m, 7H), 3.77(s, 3H), 3.95(dd, J=10, 14 Hz, 1H), 4.52 (ABq, J=17 Hz, Δv=38 Hz, 2H), 4.61(m, 1H), 5.95(br s, 1H), 6.85(m, 3H), 7.00–7.54(m, 11H), 7.67(d, J=8 Hz, 1H), 8.08(br s, 1H) | $C_{34}H_{38}N_4O_3$ | 73.06 73.03 | 6.87 6.95 | 9.99 10.03 |
| 68 | 1-(4-AcNH-4-Ph-piperidinyl) | foam | 609 (M+) | ¹H CDCl₃ 1.87–2.50(m, 7H), 2.00(s, 3H), 2.07(s, 3H), 2.60(m, 1H), 2.87–3.19(m, 5H), 3.73(s, 3H), 4.06(dd, J=10, 14 Hz, 1H), 4.46(ABq, J=17 Hz, Δv= 47 Hz, 2H), 4.52(m, 1H), 5.43(br s, 1H), 6.75–6.90 (m, 3H), 7.04–7.48(m, 10 H), 7.56(d, J=8 Hz, 1H), 7.69(d, J=8 Hz, 1H), 8.10(br s, 1H). | $C_{36}H_{43}N_5O_4$ | 70.91 70.68 | 7.11 7.13 | 11.48 11.49 |
| 69 | 1-(4-(4-Cl-Ph)-piperazinyl) | foam | 587 (M+) | CDCl₃ 2.11(s, 3H), 2.20–2.42(m, 2H), 2.42–2.58(m, 2H), 2.82–3.20(m, 9H), 3.76(s, 3H), 4.01(m, 1H), 4.50 (ABq, J=16 Hz, Δv=42 Hz, 2H), 4.54(m, 1H), 6.68–6.90(m, 5H), 7.04–7.32(m, 6H), 7.35 (d, J=8 Hz, 1H), 7.40(m, 1H), 7.66 (d, J=9 Hz, 1H), 8.03(br s, 1H) | $C_{33}H_{38}N_5O_3Cl$ | 67.39 67.10 | 6.51 6.77 | 11.91 12.11 |
| 70 | 1-(4-(3-CF₃-Ph)-piperazinyl) | foam | 621 (M+) | CDCl₃ 2.10(s, 3H), 2.28–2.42(m, 2H), 2.42–2.56(m, 2H), 2.84–3.20(m, 9H), 3.77(s, 3H), 4.01(m, 1H), 4.49 (ABq, J=18 Hz, Δv=42 Hz, 2H), 4.56(m 1H), 6.76–6.90(m, 3H), 6.90–7.27(m, 7H), 7.28–7.46(m, 3H), 7.66 (d, J=7 Hz, 1H), 8.06(br s, 1H) | $C_{34}H_{38}N_5O_3F_3$ | 65.69 65.47 | 6.16 6.28 | 11.27 11.34 |
| 71 | 1-(4-Me-piperazinyl) | foam | 492 (M + 1+) | CDCl₃ 2.09(s, 3H), 2.11–2.52(m, 11H), 2.82–2.97 (m, 3H), 2.99–3.15 (m, 2H), 3.75(s, | $C_{28}H_{37}N_5O_3$ Exact Mass Data (M + 1) Calc'd: 492.2975 Meas: 492.2977 | | | |

|   |   |   |   |   |   |   |   |   |
|---|---|---|---|---|---|---|---|---|
|   |   |   |   | 3H), 4.01(dd, J=11, 14 Hz, 1H), 4.45(ABq, J=16 Hz, Δν=46 Hz, 2H), 4.51(m, 1H), 6.76–6.88(m, 8H), 7.02–7.24(m, 4H), 7.34(d, J=8 Hz, 1H), 7.41(d, J=8 Hz, 1H), 7.68(d, J=8 Hz, 1H), 8.01 (br s, 1H) |   |   |   |   |
| 73 | 1-(4-i-Pr-piperazinyl) | foam | 519 (M⁺) | CDCl₃ 1.07(br d, J=6 Hz, 6H), 2.08(s, 3H), 2.20–2.80(m, 9H), 2.83–3.16(m, 5H), 3.77(s, 3H), 4.00(dd, J=10, 14 Hz, 1H), 4.47(ABq, J=8 Hz, Δν=42 Hz, 2H), 4.53(m, 1H), 6.73–6.94(m, 3H), 6.94–7.30(m, 4H), 7.30–7.42(m, 2H), 7.65(d, J=10 Hz, 1H), 8.06(br s, 1H) | C₃₀H₄₁N₅O₃ | 69.34 69.60 | 7.95 8.09 | 13.48 13.49 |
| 74 | 1-(4-cyclohexyl-piperazinyl) (RS) | foam | 559 (M⁺) | CDCl₃ 1.05–1.34(m, 6H), 1.55–1.95(m, 4H), 2.09(s, 3H), 2.20–2.60(m, 9H), 2.90(s, 2H), 2.85–3.16(m, 3H), 3.77(s, 3H), 4.02(dd, J=11, 13 Hz, 1H), 4.47(ABq, J=16 Hz, Δν=44 Hz, 2H), 4.54(m, 1H), 6.77–6.88(m, 3H), 7.05–7.25(m, 4H), 7.31–7.42(m, 2H), 7.66(d, J=7 Hz, 1H), 8.08(br s, 1H) | C₃₃H₄₅N₅O₃ | 70.81 71.10 | 8.10 8.28 | 12.51 12.53 |
| 75 | 1-(4-cyclohexyl-piperazinyl) (R) | foam | 560 (M + 1⁺) | CDCl₃ 1.09–1.28(m, 5H), 1.64(d, J=10 Hz, 1H), 1.80–1.89(m, 4H), 2.10(s, 3H), 2.24–2.52(m, 9H), 2.90(s, 2H), 2.95(d, J=7 Hz, 1H), 3.02(d, J=7 Hz, 1H), 3.12(dd, J=5, 14 Hz, 1H), 3.77(s, 3H), 4.01(dd, J=10, 14 Hz, 1H), 4.49(ABq, J=17 Hz, Δν=43 Hz, 2H), 4.56(m, 1H), 6.79–6.87(m, 3H), 7.05–7.24(m, 4H), 7.34–7.41(m, 2H), 7.67(d, J=8 Hz, 1H), 8.22(s, 1H) | C₃₃H₄₅N₅O₃ | 70.81 70.71 | 8.10 8.21 | 12.51 12.42 |
| 76 | 1-(4-cyclohexyl-piperazinyl) (S) | foam | 559 (M⁺) | ¹H CDCl₃ 1.05–1.31(m, 5H), 1.64(m, 1H), 1.75–1.90(m, 4H), 2.10(s, 8H), 2.24–2.52(m, 9H), 2.87(s, 2H), 2.95(d, J=7 Hz, 1H), 3.01 (d, J=7 Hz, 1H), 3.12(dd, J=5, 14 Hz, 1H), 3.77(s, 3H), 3.99(dd, J=10, 14 Hz, 1H), 4.46 (ABq, J=17 Hz, Δν=48 Hz, 2H), 4.56(m, 1H), 6.75–6.90(m, 3H), 7.05–7.24(m, 4H), 7.34–7.41(m, 2H), 7.67(d, J=8 Hz, 1H), 8.14(s, 1H) | C₃₃H₄₅N₅O₃ | 70.81 70.99 | 8.10 8.27 | 12.51 12.76 |
| 77 | 1-(4-PhCH₂-piperazinyl) | foam | 568 (M + 1⁺) | CDCl₃ 2.08(s, 3H), 2.16–2.62 m, 8H), 2.82–2.97(m, 3H), 2.99–3.18(m, 2H), 3.41–3.62(m, 2H), 3.76(s, 3H), 4.02(dd, J=10, 13 Hz, 1H), 4.49(ABq, J=18 Hz, Δν=48 Hz, 2H), 4.53(m, 1H), 6.76–6.88(m, 3H), 7.06(d, J=3 Hz, 1H), 7.06–7.45(m, 10H), 7.68(d, J=8 Hz, 1H), 8.06(br s, 1H) | C₃₄H₄₁N₅O₃ | 71.93 72.15 | 7.28 7.37 | 12.34 12.56 |
| 78 | 1-(4-(2-pyrimidinyl)-piperazinyl) | foam | 555 (M⁺) | CDCl₃ 2.11(s, 3H), 2.28–2.55(m, 4H), 2.88–3.12(m, 5H), 3.56–3.86(m, 4H), 3.77(s, 3H), 4.02(m, 1H), 4.47(ABq, J=17 Hz, Δν=41 Hz, 2H), 4.52(m, 1H), 6.50(br s, 1H), 6.76–6.86 (m, 3H), 7.04–7.28(m, 4H), 7.36(d, J=7 Hz, 1H), 7.61(br s, 1H), 7.67(d, J=7 Hz, 1H), 8.10(br s, 1H), 8.30(d, J=5 Hz, 1H) | C₃₁H₃₇N₇O₃ | 67.01 66.90 | 6.71 6.85 | 17.64 17.43 |
| 79 | 1-(4-MeCO-piperazinyl) | foam | 519 (M⁺), 520 (M + 1⁺) | CDCl₃ 2.04(s, 3H), 2.09(s, 3H), 2.16–2.48 (m, 4H), 2.86–3.11(m, 4H), 3.21–3.65(m, 5H), 3.78(s, 3H), 4.04(m, 1H), 4.46(ABq, J=17 Hz, Δν=26 Hz, 2H), 4.50(m, 1H), 6.76–6.86(m, 3H), 7.02–7.28(m, 4H), 7.36(d, J=7 Hz, 1H), 7.50(br s, 1H), 7.66(d, J=7 Hz, 1H), 8.11(br s, 1H) | C₂₉H₃₇N₅O₄ | 67.03 66.81 | 7.18 7.20 | 13.48 13.30 |
| 80 | 1-(4-EtO(CO)-piperazinyl) | foam | 549 (M⁺) | CDCl₃ 1.23(t, J=7 Hz, 3H), 2.08(s, 3H), 2.12–2.40(m, 4H), 2.85–2.97(m, 3H), 2.98–3.12(m, 2H), 3.22–3.49(m, 4H), 3.75(s, 3H), 4.03(m, 1H), 4.11(q, J=7 Hz, 2H), 4.44(ABq, J=17 Hz, Δν=45 Hz, 2H), 4.48(m, 1H), 6.76–6.86 (m, 3H), 7.04–7.25(m, 4H), 7.34(d, J=8 Hz, 1H), 7.46(br s, 1H), 7.66(d, J=8 Hz, 1H), 8.04(br s, 1H) | C₃₀H₃₉N₅O₅ | 65.55 65.29 | 7.15 7.19 | 12.74 12.59 |
| 81 | (2-pyridyl)CH₂NH | foam | 499 (M⁺) | CDCl₃ 2.10(s, 3H), 2.91(m, 1H), 3.00–3.16 (m, 2H), 3.30(s, 2H), 3.65–3.88(m, 1H), 3.77 (s, 3H), 4.01(dd, J=10, 16 Hz, 1H), 4.46 (ABq, J=17 Hz, Δν=53 Hz, 2H), 4.54(m, 1H), 6.74–6.86(m, 2H), 7.02–7.28(m, 7H), 7.34(d, J=8 Hz, 1H), 7.56–7.72(m, 3H), 8.06(br s, 1H), 8.55(d, J=6 Hz, 1H) | C₂₉H₃₃N₅O₃ | 69.72 69.75 | 6.66 6.84 | 14.02 13.88 |

-continued

| | | | | | | | | |
|---|---|---|---|---|---|---|---|---|
| 82 | (3-pyridyl)CH$_2$NH | foam | 499 (M$^+$) | CDCl$_3$ 2.08(s, 3H), 2.90(dd, J=8, 15 Hz, 1H), 2.97–3.10(m, 2H), 3.24(s, 2H), 3.69(ABq, J=14 Hz, Δv=25 Hz, 2H), 3.74(s, 3H), 4.04 (dd, J=13, 16 Hz, 1H), 4.45(ABq, J=18 Hz, Δv=53 Hz, 2H), 4.50(m, 1H), 6.74–6.87(m, 3H), 7.04(d, J=4 Hz, 1H), 7.08–7.30(m, 4H), 7.35(d, J=8 Hz, 1H), 7.49(d, J=8 Hz, 1H), 7.60–7.70(m, 2H), 8.12(br s, 1H), 8.48–8.52 (m, 2H) | C$_{29}$H$_{33}$N$_5$O$_3$ | 69.72 69.51 | 6.66 6.79 | 14.02 13.90 |
| 83 | (4-pyridyl)CH$_2$NH | foam | 499 (M$^+$) | CDCl$_3$ 2.09(s, 3H), 2.84–3.10(m, 3H), 3.20(s, 2H), 3.65(ABq, J=14 Hz, Δv=25 Hz, 2H), 3.72(s, 3H), 4.08(dd, J=12, 15 Hz, 1H), 4.40(ABq, J=16 Hz, Δv=51 Hz, 2H), 4.48(m, 1H), 6.73–6.84(m, 3H), 7.00 (d, J=3 Hz, 1H), 7.08–7.25(m, 5H), 7.32(d, J=8 Hz, 1H), 7.45(d, J=8 Hz, 1H), 7.67(d, J=8 Hz, 1H), 8.01 (br s, 1H), 8.51(d, J=7 Hz, 2H) | C$_{29}$H$_{33}$N$_5$O$_3$ | 69.72 69.99 | 6.66 6.77 | 14.02 13.79 |
| 84 | PhNHCOCH$_2$NH | foam | 541 (M$^+$) | $^1$H DMSO (3:2 mixture of amide rotamers) 1.95(s, 3/5.3H), 2.20(s, 2/5.3H), 2.75–2.93(m, 2H), 3.07–3.17(m, 2H), 3.17–3.30(m, 3H), 3.39(m, 1H), 3.53 (m, 1H), 3.67(s, 2/5.3H), 3.72(s, 3/5.3H), 4.25–4.61 (m, 3H), 6.77–6.87(m, 2H), 6.87–7.09(m, 4H), 7.12 (m, 1H), 7.14–7.36(m, 4H), 7.55(d, J=8 Hz, 1H), 7.63 (t, J=8 Hz, 2H), 7.91(d, J=9 Hz, 3/5.1H), 8.05(d, J=9 Hz, 2/5.1H), 9.92(br s, 0.4H), 9.94(br s, 0.6 H), 10.78(br s, 0.6H), 10.80(br s, 0.4H). | C$_{31}$H$_{35}$N$_5$O$_4$ | 68.74 68.51 | 6.51 6.56 | 12.93 12.78 |

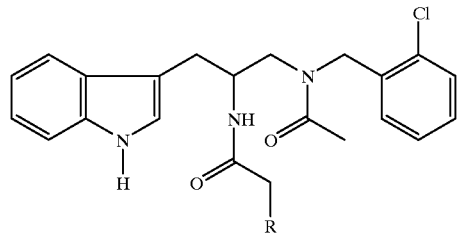

| Example | | Mp | | | | Analysis Theory/Found | | |
|---|---|---|---|---|---|---|---|---|
| No. | R | ° C. | MS | $^1$H NMR | Formula | C | H | N |
| 86 | 1-(4-i-Pr-piperazinyl) (R) | foam | 528 (M$^+$) | $^1$H CDCl$_3$ 0.9–1.1(m, 6H), 2.05(s, 3H), 2.1–2.5(m, 11H), 2.8–3.1(m, 3H), 3.2 (m, 1H), 4.0(m, 1H), 4.5–4.7 (m, 2H), 6.9–7.4(m, 9H), 7.63(d, J=6 Hz, 1H), 8.23 (br s, 1H). | C$_{29}$H$_{38}$ClN$_5$O$_2$ | 66.46 66.72 | 7.31 7.33 | 13.36 13.30 |
| 87 | 1-(4-cyclohexyl-piperazinyl) (R) | foam | 563 (M$^+$) | $^1$H CDCl$_3$ 1.0–1.4(m, 6H), 1.6(m, 1H), 1.7–1.9(m, 4H), 2.08(s, 3H), 2.1–2.6(m, 9H), 2.8–3.1(m, 4H), 4.0(m, 1H), 4.5–4.7(m, 3H), 7.0–7.4(m, 9H), 7.63(d, J=6 Hz, 1H), 8.18(br s, 1H). | C$_{32}$H$_{42}$ClN$_5$O$_2$ | 68.18 67.93 | 7.50 7.53 | 12.41 12.43 |

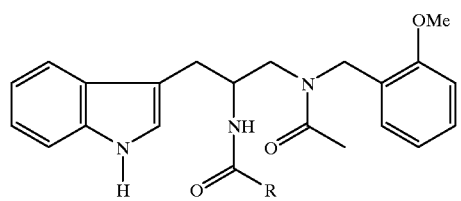

| Example | | Mp | | | | Analysis Theory/Found | | |
|---|---|---|---|---|---|---|---|---|
| No. | R | ° C. | MS | $^1$H NMR | Formula | C | H | N |
| 88 | Ph | foam | 455 (M$^+$) | CDCl$_3$ 2.10(s, 3H), 2.81–2.94(m, 2H), 3.32(dd, J=5, 15 Hz, 1H), 3.66(s, 3H), 4.21(dd, J=13, 15 Hz, 1H), 4.36(ABq, J=15 Hz, Δv=43 | C$_{28}$H$_{29}$N$_3$O$_3$ | 73.82 73.86 | 6.42 6.44 | 9.22 9.36 |

-continued

| | | | | | | | | |
|---|---|---|---|---|---|---|---|---|
| | | | | Hz, 2H), 4.46(m, 1H), 6.61–6.80(m, 3H), 7.00(d, J=5 Hz, 1H), 7.10–7.50(m, 7H), 7.70(d, J=8 Hz, 1H), 7.80 (d, J=6 Hz, 1H), 7.87(d, J=6 Hz, 2H), 7.96(br s, 1H) | | | | |
| 89 | Ph(CH$_2$)$_2$ (RS) | foam | 483 (M$^+$) | CDCl$_3$ 2.05(s, 3H), 2.45(t, J=9 Hz, 2H), 2.72–3.12(m, 5H), 3.71(s, 3H), 4.01(dd, J=12, 14 Hz, 1H), 4.33(ABq, J=16 Hz, Δv=60 Hz, 2H), 4.38(m, 1H), 6.58(d, J=9 Hz, 1H), 6.66–6.81(m, 3H), 6.88(d, J=3 Hz, 1H), 7.09–7.38(m, 9H), 7.68(d, J=7 Hz, 1H), 7.98(br s, 1H) | C$_{30}$H$_{33}$N$_3$O$_3$ | 74.51 74.81 | 6.88 7.06 | 8.69 8.39 |
| 90 | Ph(CH$_2$)$_2$(R) | foam | 283 (M$^+$) | $^1$H CDCl$_3$ 2.05(s, 3H), 2.46 (t, J=8 Hz, 2H), 2.70–2.90 (m, 2H), 2.96(t, J=8 Hz, 2H), 3.10(m, 1H), 3.71(s, 3H), 4.03(m, 1H), 4.24(d, J=17 Hz, 1H), 4.33–4.50(m, 2H), 6.60–6.86(m, 4H), 6.89 (s, 1H), 7.05–7.40(m, 9H), 7.69(d, J=8 Hz, 1H), 8.03(s, 1H) | C$_{30}$H$_{33}$N$_3$O$_3$ | 74.51 74.30 | 6.88 6.66 | 8.69 8.46 |
| 91 | Ph(CH$_2$)$_2$(S) | foam | 483 (M$^+$) | $^1$H CDCl$_3$ 2.04(s, 3H), 2.45 (t, J=8 Hz, 2H), 2.73–2.89 (m, 2H), 2.96(t, J=8 Hz, 2H), 3.06(dd, J=4, 10Hz, 1H), 3.71(s, 3H), 4.03(m, 1H), 4.20–4.50(m, 3H), 6.58–6.88(m, 4H), 6.89(s, 1H), 7.07–7.40(m, 9H), 7.69(d, J=8 Hz, 1H), 8.03(s, 1H) | C$_{30}$H$_{33}$N$_3$O$_3$ | 74.51 74.60 | 6.88 6.96 | 8.69 8.70 |
| 92 | PhCH$_2$O (R) | foam | 485 (M$^+$) | $^1$H CDCl$_3$ 2.09(s, 3H), 2.83 (dd, J=7, 15 Hz, 1H), 2.95 (dd, J=3, 14 Hz, 1H), 3.10 (dd, J=3, 14 Hz, 1H), 3.70(s, 3H), 3.96(m, 1H), 4.22(m, 1H), 4.26(m, 1H), 4.72(s, 1H), 5.12(s, 2H), 5.68(m, 1H), 6.68–6.83(m, 2H), 6.97 (m, 1H), 7.07–7.46(m, 10H), 7.66(d, J=8 Hz, 1H), 8.02(s, 1H) | C$_{29}$H$_{31}$N$_3$O$_4$ | 71.73 71.61 | 6.43 6.21 | 8.65 8.67 |
| 93 | PhCH$_2$O (S) | oil | 485 (M$^+$) | $^1$H CDCl$_3$ 1.70–2.10(m, 3H), 2.75–3.00(m, 2H), 3.10 (m, 1H), 3.70(s, 3H), 3.95 (m, 1H), 4.10(m, 1H), 4.45 (m, 1H), 4.61(s, 1H), 5.13 (s, 2H), 5.73(m, 1H), 6.66–6.85(m, 2H), 6.95(m, 1H), 7.03–7.50(m, 10H), 7.66(d, J=8 Hz, 1H), 8.02(br s, 1H). | C$_{29}$H$_{31}$N$_3$O$_4$ | 71.73 71.90 | 6.43 6.60 | 8.65 8.51 |
| 94 | Ph(CH$_2$)$_3$ | foam | 497 (M$^+$) | CDCl$_3$ 1.88–2.00(m, 2H), 2.09(s, 3H), 2.13–2.23(m, 2H), 2.61(t, J=8 Hz, 2H), 2.78–2.92(m, 2H), 3.12(dd, J=4, 9 Hz, 1H), 3.69(s, 3H), 4.10(dd, J=7, 9 Hz, 1H), 4.40(ABq, J=17 Hz, , Δv=56 Hz, 2H), 4.40(m, 1H), 6.61 (br s, 1H), 6.67–6.81(m, 3H), 6.99(s, 1H), 7.04–7.36 (m, 9H), 7.70(d, J=8 Hz, 1H), 7.98(br s, 1H) | C$_{31}$H$_{35}$N$_3$O$_3$ | 74.82 74.58 | 7.09 7.13 | 8.44 8.32 |
| 95 | PhCO(CH$_2$)$_2$ (RS) | foam | 511 (M$^+$) | CDCl$_3$ 2.17(s, 3H), 2.57(t, J=7 Hz, 2H), 2.79–2.89(m, 2H), 3.11(dd, J=6, 14 Hz, 1H), 3.21–3.45(m, 2H), 3.68 (s, 3H), 4.09(dd, J=12, 14 Hz, 1H), 4.38(ABq, J=16 Hz, Δv=75 Hz, 2H), 4.40(m, 1H), 6.71–6.79(m, 4H), 7.01 (d, J=3 Hz, 1H), 7.09–7.22 (m, 3H), 7.34(d, J=7 Hz, 1H), 7.46(t, J=8 Hz, 2H), 7.56(m, 1H), 7.70(d, J=8 | C$_{31}$H$_{33}$N$_3$O$_4$ | 72.78 72.71 | 6.50 6.38 | 8.21 7.95 |

-continued

| | | | | | | | | | |
|---|---|---|---|---|---|---|---|---|---|
| | | | | Hz, 1H), 8.00(d, J=8 Hz, 3H) | | | | | |
| 96 | PhCO(CH$_2$)$_2$ (R) | | oil | 511 (M$^+$) | $^1$H CDCl$_3$ 2.19(s, 3H), 2.58(t, J=4 Hz, 1H), 2.80–2.93(m, 2H), 3.05(m, 1H), 3.20–3.46(m, 3H), 3.70(s, 3H), 4.05(m, 1H), 4.26(m, 1H), 4.33–4.60(m, 2H), 6.66–6.86(m, 4H), 7.00(s, 1H), 7.06–7.23(m, 3H), 7.30(d, J=8 Hz, 1H), 7.43–7.53(m, 2H), 7.58(d, J=8 Hz, 1H), 7.70(d, J=8 Hz, 1H), 7.97(d, J=8 Hz, 2H), 8.12(s, 1H). | C$_{31}$H$_{33}$N$_3$O$_4$ | 72.78 72.84 | 6.50 6.61 | 8.21 8.22 |
| 97 | PhCO(CH$_2$)$_2$ (S) | | oil | 511 (M$^+$) | $^1$H DMSO (4:3 mixture of amide rotamers) 1.70 (s, 4/7.1H), 1.77(s, 3/7.1H), 1.92(s, 4/7.3H), 2.00(s, 3/7.3H), 2.40(m, 1H), 2.60–2.80 (m, 2H), 3.10–3.25(m, 3H), 3.50(m, 1H), 3.65 (s, 3/7.3H), 3.72(s, 4/7.3H), 4.25–4.60(m, 3H), 6.75–7.35(m, 8H), 7.45–7.70(m, 4H), 7.74 (d, J=8 Hz, 1H), 7.80–8.00(m, 2H), 10.77(m, 1H). | C$_{31}$H$_{33}$N$_3$O$_4$ | 72.78 72.86 | 6.50 6.50 | 8.21 8.17 |
| 98 | PhCO(CH$_2$)$_3$ | | foam | 525 (M$^+$) | CDCl$_3$ 2.00–2.11(m, 2H), 2.11(s, 3H), 2.25(t, J=7 Hz, 2H), 2.76–2.91(m, 2H), 2.98–3.16(m, 3H), 3.71(s, 3H), 4.04(dd, J=11, 13 Hz, 1H), 4.38(ABq, J=17 Hz, Δν=54 Hz, 2H), 4.39(m, 1H), 6.60–6.81(m, 4H), 6.98(s, 1H), 7.08–7.24 (m, 3H), 7.34(d, J=9 Hz, 1H), 7.45(t, J=9 Hz, 2H), 7.55(m, 1H), 7.70(d, J=9 Hz, 1H), 7.96(d, J=8 Hz, 2H), 8.01(br s, 1H) | C$_{32}$H$_{35}$N$_3$O$_4$ | 73.12 72.86 | 6.71 6.66 | 7.99 7.73 |

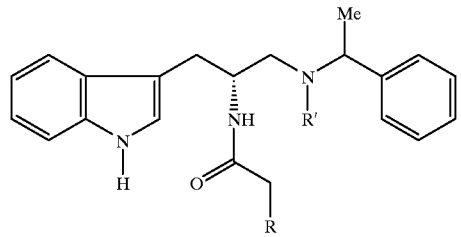

| | | | Mp | | | | Analysis % Theory/Found | | |
|---|---|---|---|---|---|---|---|---|---|
| Example No. | R | R' | °C. | MS | $^1$H NMR | Formula | C | H | N |
| 99 | H (RS) | MeCO | foam | 377 (M$^+$) | CDCl$_3$ 1.42(d, J=8 Hz, 3H), 1.92(s, 3H), 2.23(s, 3H), 2.53(dd, J=8, 14 Hz, 1H), 2.85–3.05(m, 2H), 3.28(m, 1H), 3.81(dd, J=10, 14 Hz, 1H), 4.94(q, J=8 Hz, 1H), 6.82(m, 1H), 6.82–7.27(m, 7H), 7.27–7.45(m, 2H), 7.54 (d, J=8 Hz, 1H), 8.01(br s, 1H) | C$_{23}$H$_{27}$N$_3$O$_2$ | 73.18 73.35 | 7.21 7.46 | 11.13 10.90 |
| 100 | H (RR) | MeCO | foam | 377 (M$^+$) | CDCl$_3$ 1.38(d, J=8 Hz, 3H), 1.93(s, 3H), 2.17(s, 3H), 2.68(dd, J=8, 14 Hz, 1H), 2.74(dd, J=4, 14 Hz, 1H), 3.20(dd, J=4, 14 Hz, 1H), 3.91(dd, J=10, 14 Hz, 1H), 4.37(m, 1H), 4.92(m, 1H), 6.78–7.27(m Hz, 9H), 7.37 (d, J=8 Hz, 1H), 7.75(d, J=8 Hz, 1H), 7.98(br s, 1H) | C$_{23}$H$_{27}$N$_3$O$_2$ | 73.18 73.39 | 7.21 7.33 | 11.13 10.96 |
| 101 | 1-(4-(1-piperidinyl)-piperidinyl) (RS) | H | foam | 501 (M$^+$) | CDCl$_3$ 1.32(d, J=7 Hz, 3H), 1.15–1.91(m, 11H), 1.91–2.23(m, 3H), 2.30–2.60(m, 6H), 2.65(dd, J=6, 14 Hz, 1H), 2.72–2.94(m, 4H), 3.01 (dd, J=6, 14 Hz, 1H), 3.72 (q, J=7 Hz, 1H), 4.35(m, 1H), 6.95(d, J=2 Hz, 1H), 7.03–7.42(m, 9H), 7.64(d, J=8 Hz, 1H), 8.08(br s, 1H) | C$_{31}$H$_{43}$N$_5$O | 74.21 74.50 | 8.64 8.49 | 13.96 13.94 |
| 102 | 1-4-(1-piperidinyl)-piperidinyl) (RR) | H | foam | 501 (M$^+$) | DMSO d$_6$ 1.23(d, J=6 Hz, 3H), 1.12–1.70(m, 11H), 1.89–2.01(m, 2H), 2.01–2.17 (m, 2H), 2.23–2.43(m, 5H), 2.52(m, 1H), 2.72(m, 1H), | C$_{31}$H$_{43}$N$_5$O | 74.21 73.93 | 8.64 8.65 | 13.96 13.89 |

-continued

| No. | | | | | | | | | | |
|---|---|---|---|---|---|---|---|---|---|---|
| | | | | | 2.75(ABq, J=15 Hz, Δν=30 Hz, 2H), 2.83(dd, J=8, 14 Hz, 1H), 2.95(dd, J=6, 14 Hz, 1H), 3.66(q, J=6 Hz, 1H), 4.06(m, 1H), 6.95(t, J=8 Hz, 1H), 6.99–7.10(m, 2H), 7.10–7.41(m, 6H), 7.49 (d, J=9 Hz, 1H), 7.56(d, J=8 Hz, 1H), 10.78(br s, 1H) | | | | | |
| 103 | 1-(4-(1-piperidinyl)-piperidinyl) (RS) | | MeCO | foam | 543 (M+) | CDCl$_3$ 1.29–1.88(m, 12H), 1.88–2.08(m, 2H), 2.15(s, 3H), 2.21(m, 1H), 2.36–2.62 (m, 6H), 2.62–2.88(m, 4H), 2.96(dd, J=6, 14 Hz, 1H), 3.28(dd, J=6, 14 Hz, 1H), 3.65(dd, J=10, 14 Hz, 1H), 3.82(m, 1H), 4.98(m, 1H), 6.85–7.45(m, 9H), 7.48–7.59 (m, 2H), 8.10(br s, 1H) | C$_{33}$H$_{45}$N$_5$O$_2$ | 72.89 73.13 | 8.34 8.27 | 12.88 12.91 |
| 104 | 1-(4-(1-piperidinyl)-pipendinyl) (RR) | | MeCO | foam | 543 (M+) | DMSO-d$_6$ 2:1 mixture of amide rotamers 1.19–1.84 (m, 12H), 1.84–2.16(m, 3H), 2.06(s, 3H), 2.32–2.52 (m, 5H), 2.57–3.00(m, 6H), 3.20(m, 1H), 3.79(dd, J=11, 14 Hz, 1H), 4.28(m, 1H), 5.04(m, 2/3.1H), 5.49 (m, 1/3.1H), 6.89–7.15(m, 5H), 7.15–7.28(m, 3H), 7.32 (d, J=8 Hz, 1H), 7.47(m, 1H), 8.41(m, 1H), 10.77 (br s, 1H) | C$_{33}$H$_{45}$N$_5$O$_2$ | 72.89 72.65 | 8.34 8.14 | 12.88 12.71 |

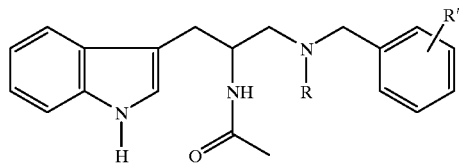

| Example No. | R | R' | Mp °C. | MS | $^1$H NMR | Formula | Analysis % Theory/Found | | |
|---|---|---|---|---|---|---|---|---|---|
| | | | | | | | C | H | N |
| 105 | H | 2-OMe | foam | 351 (M+) | CDCl$_3$ 1.97(s, 3H), 2.38(m, 1H), 2.73(dd, J=6, 12 Hz, 1H), 2.82(dd, J=6, 12 Hz, 1H), 2.97 (dd, J=8, 14 Hz, 1H), 3.10(dd, J=6, 14 Hz, 1H), 3.75–3.94(m, 2H), 3.82(s, 3H), 4.42(m, 1H), 6.34(br d, J=8 Hz, 1H), 6.77–6.95(m, 2H), 7.01(d, J=2 Hz, 1H), 7.07–7.38(m, 4H), 7.37(d, J=8 Hz, 1H), 7.68(d, J=8 Hz, 1H), 8.13(br s, 1H) | C$_{21}$H$_{25}$N$_3$O$_2$ | 71.77 71.48 | 7.17 6.90 | 11.96 12.09 |
| 106 | MeCO | 2-OMe | 147–148 | 393 (M+) | CDCl$_3$/DMSOd$_6$ 1.95(s, 3H), 2.13(s, 3H), 2.81(dd, J=8, 16 Hz, 1H), 2.89(dd, J=4, 14 Hz, 1H), 3.72(s, 3H), 3.99(t, J=10 Hz, 1H), 4.35(m, 1H), 4.37 (ABq, J=16 Hz, Δν=58 Hz, 2H), 7.65–7.82(m, 4H), 6.99(s, 1H), 7.01–7.22(m, 3H), 7.37(d, J=7 Hz, 1H), 7.66(d, J=8 Hz, 1H), 9.19(br s, 1H) | C$_{23}$H$_{27}$N$_3$O$_3$ | 70.21 69.93 | 6.92 7.06 | 10.68 10.58 |

-continued

| | | | | | | | | | | |
|---|---|---|---|---|---|---|---|---|---|---|
| 107 | 1-(4-Ph-piperazinyl)CH$_2$CO | 2-OMe | foam | 558 (M$^+$) | CDCl$_3$ 1.93(s, 3H), 2.72–2.98 (m, 6H), 3.08(dd, J=6, 15 Hz, 1H), 3.18–3.52(m, 6H), 3.73(s, 3H), 4.02(t, J=13 Hz, 1H), 4.33 (d, J=16 Hz, 1H), 4.42(m, 1H), 4.64(d, J=16 Hz, 1H), 6.45(d, J=8 Hz, 1H), 6.66–6.95(m, 6H), 7.00(d, J=3 Hz, 1H), 7.04–7.30 (m, 5H), 7.36(d, J=9 Hz, 1H), 7.67(d, J=8 Hz, 1H), 8.07(br s, 1H) | C$_{33}$H$_{39}$N$_5$O$_3$ | 71.58 71.33 | 7.10 7.09 | 12.65 12.51 |
| 108 | 1-(4-(1-piperidinyl)-piperidinyl)CH$_2$CO | H | foam | 530 (M + 1) | CDCl$_3$ 2:1 mixture of amide rotamers 1.24–1.89(m, 10H), 1.90(s, 2/3.3H), 1.96(s, 1/3.3H), 1.92–2.10(m, 2H), 2.23(m, 1H), 2.34(m, 1H), 2.42–2.53(m, 2H), 2.62–2.94 (m, 5H), 3.01–3.23(m, 3H), 3.57(dd, J=12, 14 Hz, 1/3.1H), 4.06(dd, J=12, 15 Hz, 2/3.1H), 4.43(br s, 2/3.1H), 4.57(ABq, J=16 Hz, Δν=169 Hz, 2/3.2H), 4.58 (ABq, J=16 Hz, Δν=273 Hz, 1/3.2H), 4.63(br s, 1/3.1H), 6.38(d, J=8 Hz, 2/3.1H), 6.73 (d, J=8 Hz, 1/3.1H), 6.84–6.98 (m, 2H), 7.05–7.30(m, 6H), 7.34(d, J=7 Hz, 1H), 7.53(d, J=8 Hz, 1/3.1H), 7.66(d, J=8 Hz, 2/3.1H), 7.99(br s, 2/3.1H), 8.13(br s, 1/3.1H) | C$_{32}$H$_{43}$N$_5$O$_2$ | 72.56 72.29 | 8.18 8.04 | 13.22 13.21 |
| 109 | 1-(4-(1-piperidinyl)-piperidinyl)CH$_2$CO | 2-Cl | foam | 563 (M$^+$) | CDCl$_3$ 3:1 mixture of amide rotamers 1.38–1.86(m, 11H), 1.98(s, 3/4.3H), 1.98(s, 1/4.3H), 1.86–2.12(m, 2H), 2.18–2.73(m, 5H), 2.77–2.98 (m, 3H), 2.99–3.19(m, 3H), 3.57(dd, J=12, 14 Hz, 1/4.1H), 4.10(dd, J=12, 14 Hz, 3/4.1H), 4.41(m, 3/4.1H), 4.65(m, 1/4.1H), 4.66(ABq, J=18 Hz, Δν=107 Hz, 3/4.2H), 4.72 (ABq, J=15 Hz, Δν=157 Hz, 1/4.2H), 6.40(br d, J=7 Hz, 1H), 6.90(d, J=7 Hz, 1H), 7.02 (br s, 1H), 7.06–7.40(m, 6H), 7.55(d, J=8 Hz, 1/4.1H), 7.64 (d, J=8 Hz, 3/4.1H), 8.04(br s, 1H) | C$_{32}$H$_{42}$ClN$_5$O$_2$ | 68.13 66.92 | 7.50 7.48 | 12.41 12.32 |

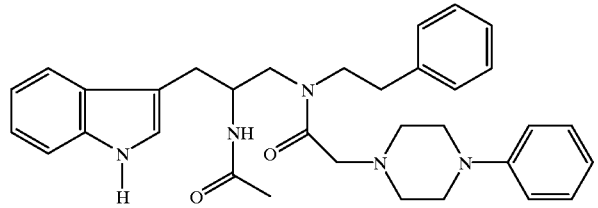

| Example No. | Mp ° C. | MS | $^1$H NMR | Formula | Analysis, Theory/Found | | |
|---|---|---|---|---|---|---|---|
| | | | | | C | H | N |
| 110 | | foam | 537 (M$^+$) | $^1$H DMSO (3:2 mixture of amide rotamers) 1.79(s, 3/5.3H), 1.81(s, 2/5.3H), 2.25–2.46(m, 4H), 2.59–3.21(m, 10H), 3.23–3.67(m, 4H), 4.46(m, 1H), 6.76(t, J=8 Hz, 1H), 6.91(d, J=8 Hz, 2H), 6.94–7.40(m, 11H), 7.60(m, 1H), 7.81–8.05(m, 1H), 10.81(br s, 2/5.1H), 10.84(br s, 3/5.1H). | C$_{33}$H$_{39}$N$_5$O$_2$ | 73.71 73.64 | 7.31 7.33 | 13.02 13.08 |

-continued

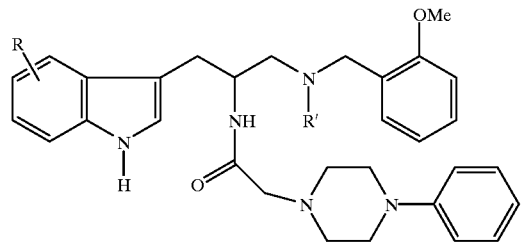

| Example No. | R | R' | Mp °C. | MS | ¹H NMR | Formula | Analysis % Theory/Found | | |
|---|---|---|---|---|---|---|---|---|---|
| | | | | | | | C | H | N |
| 111 | 5-Br | H | oil | 590, 592 (M + 1) for Br isotopes) | CDCl₃ 2.33–2.45(m, 2H), 2.45–2.53 (m, 2H), 2.80–3.10(m, 11H), 3.75(s, 1H), 3.88(s, 3H), 3.94(d, J=4 Hz, 2H), 6.80–6.96(m, 6H), 7.10(s, 1H), 7.20–7.36(m, 5H), 7.40(m, 1H), 7.75(s, 1H), 8.20(s, 1H) | $C_{31}H_{36}N_5O_2Br$ | 63.05 63.21 | 6.14 6.21 | 11.86 11.59 |
| 112 | 5-OCH₂Ph | H | oil | 617 (M⁺) | DMSO-d₆ 2.30–2.65(m, 8H), 2.80–3.15(m, 8H), 3.31(s, 1H), 3.64(s, 2H), 3.72(s, 3H), 4.15(m, 1H), 6.65–6.95(m, 6H), 7.05(s, 1H), 7.10–7.25(m, 5H), 7.25–7.40(m, 4H), 7.43(d, J=9 Hz, 2H), 7.50(d, J=9 Hz, 1H), 10.70(s, 1H) | $C_{38}H_{43}N_5O_3$ | 73.88 74.09 | 7.02 7.03 | 11.34 11.31 |
| 113 | 1-Me | MeCO | oil | 567 (M⁺) | CDCl₃ 2.11(s, 3H), 2.36–2.60(m, 3H), 2.85–3.20(m, 10H), 3.71(s, 3H), 3.77(s, 3H), 3.97(br s, 1H), 4.36–4.60(m, 3H), 6.78–7.00(m, 7H), 7.10(s, 1H), 7.20–7.35(m, 6H), 7.66(d, J=8 Hz, 1H) | $C_{34}H_{41}N_5O_3$ | 71.93 71.69 | 7.28 7.36 | 12.34 12.28 |
| 114 | 6-Me | MeCO | oil | FD-MS 567 (M⁺) | ¹H CDCl₃ 2.10(s, 3H), 2.10(m, 1H), 2.40–2.70(m, 7H), 2.90–3.10(m, 7H), 3.16(dd, J=4, 13 Hz, 1H), 3.78(s, 3H), 3.97(m, 1H), 4.40–4.70(m, 3H), 6.80–7.10(m, 8H), 7.16(s, 1H), 7.20–7.40(m, 3H), 7.45(m, 1H), 7.54(d, J=8 Hz, 1H), 7.94(m, 1H). | $C_{34}H_{41}N_5O_3$ | 71.93 71.72 | 7.28 6.99 | 12.34 12.10 |
| 115 | 7-Me | MeCO | foam | 567 (M⁺) | ¹H CDCl₃ 2.08(s, 3H), 2.35–2.53(m, 7H), 2.88–3.15(m, 10H), 3.76(s, 3H), 4.48(ABq, J=17.1 Hz, Δν=41.2 Hz, 2H), 4.55(m, 1H), 6.78–6.90(m, 6H), 6.96–7.08(m, 3H), 7.22(m, 3H), 7.40(m, 1H), 7.50(d, J=8.0 Hz, 1H), 7.95(s, 1H). | $C_{34}H_{41}N_5O_3$ | 71.93 71.82 | 7.28 7.31 | 12.34 12.32 |
| 116 | 5-Br | MeCO | 124–126 | 631, 633 (M⁺'s for Br isotopes) | CDCl₃ 2.12(s, 3H), 2.40–2.66(m, 4H), 2.83–3.20(m, 9H), 3.80(s, 3H), 3.96(m, 1H), 4.43–4.60(m, 3H), 6.83–6.96 (m, 6H), 7.10(s, 1H), 7.20–7.33(m, 5H), 7.46(br s, 1H), 7.75(s, 1H), 8.44(s, 1H) | $C_{33}H_{38}N_5O_3Br$ | 62.66 62.92 | 6.05 6.04 | 11.07 11.25 |
| 117 | 5-OMe | MeCO | oil | 583 (M⁺) Exact Mass FAB (M + 1) theory: 584.3237 found: 584.3214 | DMSO-d₆ 1:1 mixture of amide rotamers 1.86(s, 1/2.3H), 1.94(s, 1/2.3H), 2.23–2.43(m, 4H), 2.73–2.93(m, 4H), 2.93–3.10(m, 4H), 3.16(m, 1H), 3.56(m, 1H), 3.66(s, 1/2.3H), 3.69(s, 1/2.3H), 3.71(s, 1/2.3H), 3.72(s, 1/2.3H), 4.23–4.60(m, 3H), 6.66–7.00(m, 7H), 7.08(s, 2H), 7.15–7.26(m, 4H), 7.59(d, J=8 Hz, 1/2.1H), 7.77(d, J=8 Hz, 1/2.1H), 10.65(s, 1H) | $C_{34}H_{41}N_5O_4$ | | | |
| 118 | 5-OCH₂Ph | MeCO | oil | 660 (M + 1⁺) | DMSO-d₆ 3:2 mixture of amide rotamers 1.94(s, 3/5.3H), 2.04(s, 2/5.3H), 2.23–2.56(m, 5H), 2.66–2.93(m, 4H), 2.93–3.13(m, 3H), 3.30–3.50(m, 3H), 3.58(m, 1H), 3.68(s, 2/5.3H), 3.70(s, 3/5.3H), 4.24–4.60(m, 3H), 6.70–7.00(m, 7H), 7.06(s, 1H), 7.13–7.50(m, 10H), 7.55(d, J=8 Hz, 3/5.1H), 7.66(d, J=8 Hz, 2/5.1H), 10.70(s, 1H) | $C_{40}H_{45}N_5O_4$ | 72.81 72.58 | 6.87 6.85 | 10.61 10.37 |

-continued

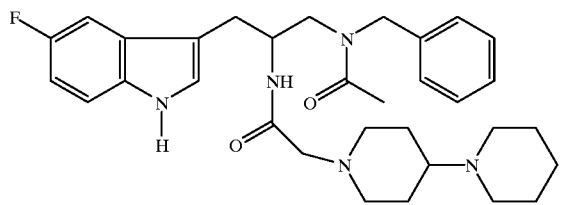

| Example No. | Mp °C. | MS | ¹H NMR | Formula | Analysis % Theory/Found | | |
|---|---|---|---|---|---|---|---|
| | | | | | C | H | N |
| 119 | foam | 548 (M⁺) | ¹H CDCl₃ 1.30–1.72(m, 10H), 1.96–2.24(m, 6H), 2.41–2.56(m, 5H), 2.70–2.77(m, 1H), 2.85(s, 2H), 2.87–3.00(m, 2H), 3.16 (dd, J=4.7, 13.8 Hz, 1H), 4.00 (dd, J=10.1, 13.8 Hz, 1H), 4.48–4.57(m, 1H), 4.55(ABq, J=17.0 Hz, Δν=47.7 Hz, 2H), 6.93(m, 1H), 7.08–7.16(m, 3H), 7.21–7.41(m, 6H), 8.27(s, 1H). | $C_{32}H_{42}FN_5O_2$ | 70.17 69.94 | 7.73 7.80 | 12.79 12.74 |

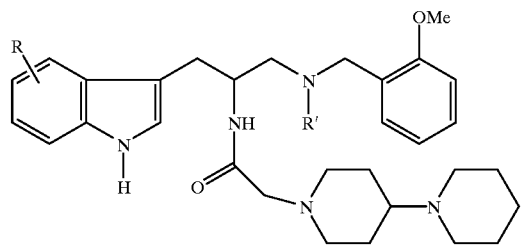

| Example No. | R | R' | Mp °C. | MS | ¹H NMR | Formula | Analysis % Theory/Found | | |
|---|---|---|---|---|---|---|---|---|---|
| | | | | | | | C | H | N |
| 120 | 5-Br | H | oil | 596, 598 (M + 1) for Br isotopes) | DMSO-d₆ 1.20–1.56(m, 12H), 1.75–2.00(m, 2H), 2.20–2.40(m, 7H), 2.60–2.80(m, 3H), 2.85(d, J=6 Hz, 2H), 3.63(br s, 2H), 3.74 (s, 3H), 4.10(m, 1H), 6.83–6.93 (m, 2H), 7.10–7.23(m, 8H), 7.23–7.30(m, 2H), 7.45(d, J=8 Hz, 1H), 7.55(s, 1H), 11.10(s, 1H) | $C_{31}H_{42}BrN_5O_2$ | 62.41 62.63 | 7.10 6.96 | 11.74 12.01 |
| 121 | 5-OMe | H | oil | 547 (M⁺) | DMSO-d₆ 1.20–1.70(m, 11H), 1.66–2.20(m, 4H), 2.20–2.43(m, 4H), 2.43–2.65(m, 3H), 2.65–2.90 (m, 4H), 3.61(s, 2H), 3.77(s, 3H), 3.80(s, 3H), 4.13(m, 1H), 6.70 (m, 1H), 6.80–7.00(m, 2H), 7.02 (s, 1H), 7.08(s, 1H), 7.10–7.40(m, 3H), 7.45(d, J=8 Hz, 1H), 10.65 (s, 1H) | $C_{32}H_{45}N_5O_3$ | 70.17 70.29 | 8.28 8.09 | 12.79 12.56 |
| 122 | 5-OCH₂Ph | H | oil | 624 (M + 1⁺) | DMSO-d₆ 1.20–1.33(m, 11H), 1.80–2.10(m, 4H), 2.25–2.40(m, 5H), 2.50–2.60(m, 3H), 2.65–2.90 (m, 5H), 3.63(s, 2H), 3.74(s, 3H), 4.08(m, 1H), 6.77(d, J=2 Hz, 1H), 6.80–7.00(m, 2H), 7.03(s, 1H), 7.13–7.25(m, 3H), 7.25–7.50 (m, 7H), 10.70(s, 1H) | $C_{38}H_{49}N_5O_3$ | 73.16 73.45 | 7.92 7.92 | 11.23 11.14 |
| 123 | 6-F | H | foam | 536 (M + 1) | ¹H CDCl₃ 1.22–1.78(m, 12H), 1.95–2.15(m, 3H), 2.43–2.57(m, 4H), 2.69–3.08(m, 7H), 3.74–3.88 (m, 5H), 4.39(m, 1H), 6.85–7.13 (m, 5H), 7.21–7.27(m, 2H), 7.33 (d, J=4.9 Hz, 1H), 7.58(m, 1H), 8.25(s, 1H). | $C_{31}H_{42}FN_5O_2$ | 71.17 70.89 | 8.26 8.26 | 12.21 11.91 |

-continued

| No. | Sub | R | Form | MS | NMR | Formula | C | H | N |
|---|---|---|---|---|---|---|---|---|---|
| 124 | 1-Me | MeCO | oil | 573 (M+) | DMSO-d6 3:2 mixture of amide rotamers 1.30–1.60(m, 11H), 1.80–1.95(m, 2H), 1.93(s, 3/5.3H), 2.03(s, 2/5.3H), 2.05 (m, 1H), 2.40(br s, 3H), 2.50–2.86 (m, 6H), 3.14(m, 1H), 3.67(m, 1H), 3.68(s, 3/5.6H), 3.71(s, 2/5.6H), 4.23–4.56(m, 3H), 6.79 (m, 1H), 6.86–7.28(m, 5H), 7.34 (d, J=8Hz, 1H), 7.53(m, 3/5.2H), 7.63(m, 2/5.2H), 8.30(s, 1H) | C34H47N5O3 | 71.17 71.30 | 8.25 7.97 | 12.21 12.09 |
| 125 | 4-Me | MeCO | foam | 573 (M+) | 1H CDCl3 1.46(m, 3H), 1.51–1.81 (m, 7H), 2.01–2.26(m, 6H), 2.43–2.68(m, 5H), 2.70–2.84(m, 4H), 2.87(s, 2H), 3.07–3.24(m, 3H), 3.78(s, 3H), 3.98(dd, J=9.8, 13.6 Hz, 1H), 4.45–4.61(m, 3H), 6.84 (m, 3H), 6.88–6.94(m, 1H), 7.03–7.10(m, 2H), 7.15–7.39(m, 3H), 8.07(s, 1H). | C34H47N5O3 | 71.17 70.84 | 8.26 8.26 | 12.21 11.91 |
| 126 | 5-Me | MeCO | foam | 573 (M+) | 1H CDCl3 1.25–1.72(m, 11H), 1.99–2.17(m, 6H), 2.46(m, 7H), 2.75(dd, J=1.4, 9.7 Hz, 1H), 2.86 (s, 2H), 2.91(d, J=7.0 Hz, 1H), 2.99(d, J=6.3 Hz, 1H), 3.14(dd, J=4.7, 13.8 Hz, 1H), 3.77(s, 3H), 3.96(dd, J=10.1, 13.8 Hz, 1H), 4.49(ABq, J=17.0 Hz, Δν=40.3 Hz, 2H), 4.54(m, 1H), 6.82–6.89 (m, 3H), 7.02(m, 2H), 7.23(d, H=8.1 Hz, 2H), 7.42(m, 2H), 7.95 (s, 1H) | C34H47N5O3 | 71.17 71.45 | 8.26 8.33 | 12.21 11.96 |
| 127 | 6-Me | MeCO | oil | 573 (M+) | 1H CDCl3 1.25–1.40(m, 2H), 1.40–1.52(m, 3H), 1.52–1.80(m, 6H), 2.02(d, J=12 Hz, 2H), 2.09(s, 3H), 2.46(s, 3H), 2.46–2.60(m, 5H), 2.75(m, 1H), 2.86(s, 2H), 2.90(d, J=15 Hz, 1H), 2.95(d, J=15 Hz, 1H), 3.15(dd, J=9, 18 Hz, 1H), 3.70(s, 3H), 3.95(m, 1H), 4.44(s, 1H), 4.50–4.63(m, 2H), 6.80–6.93(m, 3H), 6.93–7.00(m, 2H), 7.14(s, 1H), 7.25 (s, 1H), 7.42(d, J=9 Hz, 1H), 7.53(d, J=8 Hz, 1H), 8.03(brs, 1H) | C34H47N5O3 | 71.17 70.99 | 8.26 8.05 | 12.21 12.41 |
| 128 | 7-Me | MeCO | foam | 573 (M+) | 1H CDCl3 1.32–1.41(m, 4H), 1.45–1.66(m, 6H), 1.96–2.07(m, 2H), 2.09(s, 3H), 2.19(m, 1H), 2.48–2.58(m, 8H), 2.74(m, 1H), 2.81–3.07(m, 4 H), 3.14(dd, J=4.6, 13.8 Hz, 1H), 3.76(s, 3H), 3.97 (dd, J=10.2,18.8 Hz, 1H), 4.47(ABq, J=17.1 Hz, Δν=42.3 Hz, 2H), 4.55(m, 1H), 6.78–6.87(m, 3H), 6.96–7.07(m, 3H), 7.23(m, 1H), 7.45(d, J=8.6 Hz, 1H), 7.51(d, J=7.6 Hz, 1H), 8.18(s, 1H) | C34H47N5O3 | 71.17 71.33 | 8.26 8.20 | 12.21 12.29 |
| 129 | 5-Br | MeCO | Oil | 638, 640 (M + 1+'s for Br isotopes) Exact Mass FAB (M + 1): theory 638.2706 found: 638.2729 | DMSO-d6 2:1 mixture of amide rotamers 1.20–1.60 (m, 3H), 1.60–1.90(m, 6H), 1.95(s, 2/3.3H), 2.07(s, 1/3.3H), 1.90–2.07(m, 3H), 2.55–2.90(m, 5H), 2.90–3.20(m, 4H), 3.20–3.50(m, 3H), 3.62(m, 1H), 3.73 (s, 3H), 4.20–4.42(m, 3H), 6.85(m, 1H), 6.90–7.00 (m, 2H), 7.10–7.30(m, 4H), 7.50(m, 1H), 7.70(s, 2/3.1H), 7.75(s, 1/3.1H), 11.10(s, 1H) | C33H44BrN5O3 | | | |
| 130 | 5-OMe | MeCO | oil | 590 (M + 1+) | DMSO-d6 3:2 mixture of amide rotamers 1.20–1.60 (m, 12H), 1.73–1.96(m, 2H), 1.93(s, 3/5.3H), 2.02 (s, 2/5.3H), 2.33–2.43(m, 4H), 2.60–2.90(m, 6H), 3.57(m, 1H), 3.70(s, 3H), 3.71(s, 8H), 4.26–4.56 (m, 3H), 6.66(d, J=6 Hz, 1H), 6.82(m, 1H), 6.93(m, 2H), 7.03(s, 2H), 7.20(m, 2H), 7.44(d, J=6 Hz, 3/5.1H), 7.68(d, J=6 Hz, 2/5.1H), 10.65(s, 1H) | C34H47N5O4 | 69.24 69.52 | 8.03 8.14 | 11.87 11.92 |
| 131 | 5-OCH2Ph | MeCO | oil | 666 (M + 1+) | DMSO-d6 1.16–1.80(m, 12H), 1.90(m, 6H), 2.20–2.43(m, 3H), 2.53–2.90(m, 6H), 3.16(m, 1H), 3.43 (m, 1H), 3.60(m, 1H), 3.70(d, J=6 Hz, 3H), 4.20–4.60(m, 3H), 6.73–6.88(m, 3H), 6.88–7.00(m, 2H), 7.04(s, 1H), 7.15–7.26(m, 3H), 7.26–7.40(m, 3H), 7.40–7.53(m, 2H), 10.70(s, 1H) | C40H51N5O4 | 72.15 71.95 | 7.72 7.66 | 10.52 10.31 |
| 131a | 6-F | MeCO | foam | 577 (M+) | CDCl3 δ 1.32–1.46(m, 4H), 1.58–1.66(m, 6H), 1.97–2.08(m, 2H), 2.11(s, 3H), 2.19(m, 1H), 2.49(m, 5H), 2.72–3.04(m, 5H), 3.13(dd, J=4.5 Hz, Δν=13.9 Hz, 1H), 3.76(s, 3H), 3.97(dd, J=10.3 Hz, Δν=13.7 Hz, 1H), 4.47(ABq, J=17.0 Hz, Δν=42.7 Hz, 2H), 4.49(m, 1H), 6.78–6.90(m, 1H), 7.00(s, 1H), 7.04 | C33H44FN5O3 | 68.61 68.76 | 7.68 7.86 | 12.12 12.28 |

-continued (d, 2.2 Hz, 1H), 7.23(m, 1H), 7.47(d, J=8.5Hz, 1H),
7.57(dd, J=5.3Hz, Δν=8.7Hz, 1H), 8.62(s, 1H)

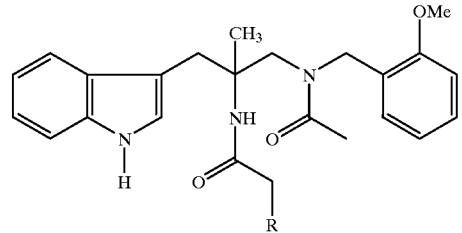

| Example No. | R | Mp °C. | MS | ¹H NMR | Formula | Analysis Theory/Found | | |
|---|---|---|---|---|---|---|---|---|
| | | | | | | C | H | N |
| 132 | 1-(4-(1-piperidinyl)-piperidinyl) | foam | 574 (M + 1⁺) | ¹H CDCl₃ 1.44(s, 3H),1.40–2.00(m, 13H), 2.08(s, 3H), 2.20–2.40(m, 2H), 2.45–2.80 (m, 6H), 3.16–3.35(m, 2H), 3.66(d,J=14Hz, 1H), 3.81(s, 3H), 4.23(d, J=14 Hz, 1H), 4.60(ABq, J=14 Hz, Δν=28 Hz, 2H), 6.86(d, J=8 Hz, 1H), 6.96(d, J=8 Hz, 1H), 7.03–7.20 (m, 4H), 7.27(s, 2H), 7.40(d, J=8 Hz, 1H), 7.60(d, J=6 Hz, 2H) | $C_{34}H_{47}N_5O_3$ | 71.17 70.94 | 8.26 8.38 | 12.21 12.28 |
| 133 | 1-(4-phenyl)-piperazinyl | foam | 568 (M + 1⁺) | ¹H CDCl₃ 1.56(s, 3H), 2.09(s, 3H), 2.43–2.85(m, 3H), 2.85–3.20(m, 7H), 3.20–3.50(m, 3H), 3.81(s, 3H), 4.20(d, J=14 Hz, 1H), 4.60(ABq, J=18 Hz, Δν=56 Hz, 2H), 6.80–7.00(m, 6H), 7.00–7.20(m, 3H), 7.20–7.36(m, 5H), 7.59(d, J=7 Hz, 1H), 8.24(s, 1H). | $C_{34}H_{41}N_5O_3$ | 71.93 71.68 | 7.28 7.49 | 12.34 12.29 |

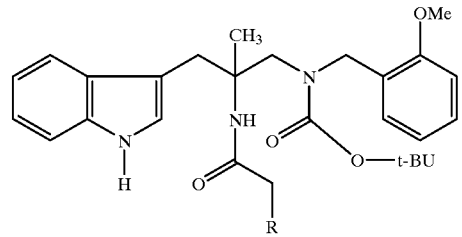

| Example No. | R | Mp °C. | MS | ¹H NMR | Formula | Analysis Theory/Found | | |
|---|---|---|---|---|---|---|---|---|
| | | | | | | C | H | N |
| 134 | Br | foam | 543, 545 (M+'s for Br isotopes) | CDCl₃ 1.31(s, 12H), 3.07(d, J=14 Hz, 1H), 3.25(d, J=14 Hz, 1H), 3.40(d, J=14 Hz, 1H), 3.66(s, 3H), 3.68(d, J=14 Hz, 1H), 3.80–3.95(m, 2H), 4.23(d, J=16 Hz, 1H), 4.64(d, J=16 Hz, 1H), 6.82(d, J=18 Hz, 1H), 6.90(m, 1H), 7.00–7.15(m, 2H), 7.15–7.30 (m, 3H), 7.30–7.40(m, 2H), 7.55(d, J=8 Hz, 1H), 8.07 (brs, 1H). | $C_{27}H_{34}BrN_3O_4$ | 59.56 58.80 | 6.29 6.21 | 7.72 7.47 |

-continued

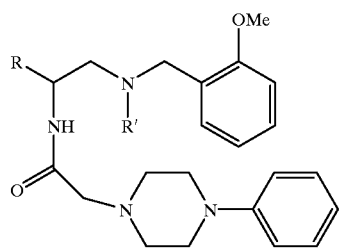

| Example No. | R | R' | Mp °C. | MS | $^1$H NMR | Formula | Analysis % Theory/Found | | |
|---|---|---|---|---|---|---|---|---|---|
| | | | | | | | C | H | N |
| 135 | 1-naphthyl-CH$_2$ | H | foam | 523 (M + 1$^+$) | CDCl$_3$ 2.32–2.45(m, 2H), 2.40 (m, 1H), 2.45–2.57(m, 2H), 2.75–3.10(m, 8H), 3.36(m, 2H), 3.84(s, 3H), 3.92(ABq, J=12 Hz, Δν=22 Hz, 2H), 4.48 (m, 1H), 6.75–7.00(m, 5H), 7.15–7.42(m, 6H), 7.42–7.64 (m, 3H), 7.74(d, J=8 Hz, 1H), 7.83(d, J=8 Hz, 1H), 8.28(d, J=8 Hz, 1H) | C$_{33}$H$_{38}$N$_4$O$_2$ | 75.83 75.55 | 7.33 7.26 | 10.72 10.60 |
| 136 | 2-naphthyl-CH$_2$ | H | foam | 522 (M$^+$) | CDCl$_3$ 2.03(m, 1H), 2.26–2.35 (m, 2H), 2.35–2.55(m, 2H), 2.65–2.95(m, 7H), 2.95–3.10 (m, 2H), 3.18(dd, J=8, 14 Hz, 1H), 3.74–4.03(m, 2H), 3.85 (s, 3H), 4.45(m, 1H), 6.75(d, J=9 Hz, 2H), 6.78–6.97(m, 3H), 7.03–7.40(m, 6H), 7.40–7.52(m, 2H), 7.63(s, 1H), 7.66–7.83(m, 3H) | C$_{33}$H$_{38}$N$_4$O$_2$ | 75.83 76.07 | 7.33 7.25 | 10.72 10.66 |
| 137 | 3-indolinyl-CH$_2$ | H | foam | 514 (M + 1$^+$) | DMSO-d$_6$ 1:1 mixture of diastereomers 1.54–1.70(m, 1H), 1.86–1.98(m, 1H), 2.52–2.64(m, 6H), 2.84–3.18(m, 8H) 3.32(br s, 1H), 3.54(m, 1H), 3.64–3.70(m, 2H), 3.76 (s, 1/2.3H), 3.78(s, 1/2.3H), 4.03(m, 1H), 5.40(br s, 1H), 6.44–6.56(m, 2H), 6.77(t, J=7 Hz, 1H), 6.82–6.98(m, 6H), 7.10–7.24(m, 3H), 7.30(br d, J=8 Hz, 1H), 7.65(t, J=9 Hz, 1H) | C$_{31}$H$_{39}$N$_5$O$_2$ | 72.48 72.57 | 7.65 7.50 | 13.63 13.70 |
| 138 | Pb | MeCO | oil | 500 (M$^+$) | CDCl$_3$ 2.14(s, 3H), 2.60–2.80 (m, 4H), 3.00–3.20(m, 2H), 3.20–3.43(m, 5H), 3.82(s, 3H),4.30(m, 1H), 4.40–4.63 (m, 2H), 5.18(m, 1H), 6.80–7.06(m, 6H), 7.03–7.40(m, 8H), 8.24(br s, 1H) | C$_{30}$H$_{36}$N$_4$O$_3$ | 71.97 71.67 | 7.25 7.29 | 11.19 11.18 |
| 139 | 3,4-diCl Ph | MeCO | oil | 568 (M$^+$) | $^1$H CDCl$_3$ 2.19(s, 3H), 2.63–2.83(m, 2H), 2.93–3.20(m, 4H), 3.20–3.50(m, 3H), 3.50–3.70(m, 2H), 3.85(s, 3H), 4.23(m, 1H), 4.30–4.60(m, 2H), 5.00(m, 1H), 6.85–7.06 (m, 5H), 7.13(m, 1H), 7.20–7.45(m, 6H), 8.41(br s, 1H,). | C$_{30}$H$_{34}$Cl$_2$N$_4$O$_3$ | 63.27 63.12 | 6.02 5.82 | 9.84 9.55 |
| 140 | PhCH$_2$ | MeCO | oil | 514 (M$^+$) | DMSO-d$_6$ 3:2 mixture of amide rotamers 1.93(s, 3/5.3H), 2.09(s, 2/5.3H), 2.23–2.46(m, 4H), 2.60–2.90 (m, 4H), 3.00–3.20(m, 2H), 3.30–3.53(m, 4H), 3.75(s, 3H), 4.20–4.60(m, 3H), 6.70–7.04(m, 7H), 7.04–7.30(m, 7H), 7.57(d, J=9 Hz, 3/5.1H), 7.71(d, J=9 Hz, 2/5.1H) | C$_{31}$H$_{38}$N$_4$O$_3$ | 72.35 72.57 | 7.44 7.47 | 10.89 10.69 |
| 141 | 1-naphthyl-CH$_2$ | MeCO | foam | 564 (M$^+$) | CDCl$_3$ 2.13(s, 3H), 2.38–2.70(m, 4H), 2.82–3.07(m, 4H), 3.07–3.30(m, 4H), 3.56(dd, J=7, 14 Hz, 1H), 3.66(s, 3H), 4.14(m, 1H), 4.34 | C$_{35}$H$_{40}$N$_4$O$_3$ | 74.44 74.50 | 7.14 7.25 | 9.92 9.94 |

-continued

| No. | R | | Mp °C. | MS | ¹H NMR | Formula | C | H | N |
|---|---|---|---|---|---|---|---|---|---|
| 142 | 2-naphthyl-CH₂ | MeCO | foam | 564 (M⁺) | (ABq, J=16 Hz, Δν=58 Hz, 2H), 4.47(m, 1H), 6.52–6.67(m, 2H), 6.73(d, J=8 Hz, 1H), 6.77–7.00(m, 3H), 7.09–7.20(m, 1H), 7.20–7.40(m, 4H), 7.43–7.70(m, 3H), 7.73(d, J=8 Hz, 1H), 7.86(d, J=8 Hz, 1H), 8.34(d, J=8 Hz, 1H) CDCl₃ 2.12(s, 3H), 2.26–2.50(m, 4H), 2.59–3.30(m, 9H), 3.78(s, 3H), 3.98(m, 1H), 4.51 (ABq, J=17 Hz, Δν=30 Hz, 2H), 4.53(m, 1H), 6.55–7.03(m, 6H), 7.05–7.39(m, 5H), 7.39–7.58(m, 2H), 7.60(m, 1H), 7.71–7.85(m, 3H) | C₃₅H₄₀N₄O₃ | 74.44 74.46 | 7.14 7.31 | 9.92 9.94 |
| 143 | 3-benzo[b]thienyl-CH₂ | MeCO | foam | 571 (M + 1⁺) | ¹H CDCl₃ 2.15(s, 3H), 2.44–2.60(m, 4H), 2.89–3.26(m, 9H), 3.73(s, 3H), 4.07(dd, J=10.4, 13.9 Hz, 1H), 4.43(ABq, J=16.5 Hz, Δν=45.4 Hz, 2H), 4.50(m, 1H), 6.74–6.92(m, 6H), 7.15(s, 1H), 7.18–7.30(m, 3H), 7.39(m, 2 H), 7.57(d, J=8.1 Hz, 1H), 7.87(d, J=7.4 Hz, 1H), 7.98(d, J=7.6 Hz, 1H). | C₃₃H₃₈N₄O₃S | 69.45 69.23 | 6.71 6.71 | 9.82 9.77 |
| 144 | 3-indolinyl-CH₂ | MeCO | 102–105 | 556 (M + 1⁺) Exact Mass FAB (M + 1): calc.: 556.3287 found: 556.3280 | CDCl₃ 1:1 mixture of diastereomers 1.57–2.08 (m, 2H), 2.15(s, 1/2.3H), 2.17(s, 1/2.3H), 2.75–3.60(m, 13H), 3.65–4.00(m, 2H), 3.82(s, 1/2.3H), 3.85(s, 1/2.3H), 4.18–4.48(m, 2H), 4.58(s, 2H), 6.70–7.40(m, 13H), 7.67(m, 1H) | C₃₃H₄₁N₅O₃ | | | |
| 145 | N-Ac-3-indolinyl-CH₂ | MeCO | 80–84 | 597 (M⁺) Exact Mass FAB (M + 1): calc.: 598.3393 found: 598.3397 | CDCl₃ 1:1 mixture of diastereomers 1.70–2.00 (m, 2H), 2.13(s, 1/2.3H), 2.17(s, 1/2.3H), 2.23(s, 1/2.3H), 2.27(s, 1/2.3H), 2.57–3.53 (m, 12H), 3.63–4.03(m, 2H), 3.82(s, 1/2.3H), 3.85(s, 1/2.3H), 4.03–4.33(m, 2H), 4.52(s, 1/2.1H), 4.54(s, 1/2.1H), 6.80–7.40(m, 12H), 7.57(m, 1H), 8.19(m, 1H) | C₃₅H₄₃N₅O₄ | | | |

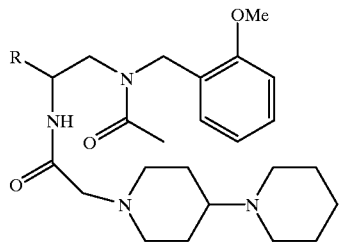

| | | | | | | | Analysis Theory/Found | | |
|---|---|---|---|---|---|---|---|---|---|
| Example No. | R | | Mp °C. | MS | ¹H NMR | Formula | C | H | N |
| 146 | Ph | | oil | 506 (M⁺) | DMSO-d₆ 2:1 mixture of amide rotamers 1.30–1.76 (m, 11H), 1.90–2.20(m, 4H), 1.96(s, 2/3.3H), 2.00(s, 1/3.3H), 2.35–2.55(m, 4H), 2.60–2.95(m, 4H), 3.78 (s, 3H), 4.43(s, 2/3.2H), 4.43(ABq, J=15 Hz, Δν=49 Hz, 1/3.2H), 4.96(m, 2/3.1H), 5.24(m, 1/3.1H), 6.80–7.05(m, 3H), 7.15–7.40(m, 6H), 8.26(d, J=9 Hz, 1H) | C₃₀H₄₂N₄O₃ | 71.11 71.38 | 8.35 8.25 | 11.06 11.07 |
| 147 | 3,4-diCl-Ph | | oil | FD 574 (M⁺) FAB Exact Mass Theory: 575.2555 Found: 575.2595 (M + 1⁺) | ¹H CDCl₃ 1.40–1.60(m, 2H), 1.60–1.80(m, 4H), 1.80–2.05(m, 5H), 2.17(s, 3H), 2.18(m, 1H), 2.40–2.80(m, 5H), 2.80–3.05(m, 5H), 3.85(s, 3H), 4.23(ABq, J=11 Hz, Δν=14 Hz, 1H), 4.48(ABq, J=17 Hz, Δν=33 Hz, 2H), 4.93(m, 1H), 6.85–7.10(m, 4H), 7.20–7.40(m, 3H), 8.35(m, 1H) | C₃₀H₄₀Cl₂N₄O₃ | 62.60 63.05 | 7.01 6.91 | 9.73 9.78 |
| 148 | PhCH₂ | | oil | 520 (M⁺) | DMSO 3:2 mixture of amide rotamers 1.30–1.63 (m 10H), 1.73–2.00(m, 3H), 1.88(s, 3/5.3H), 2.07(s, 2/5.3H), 2.40(m, 3H), 2.55–2.80(m, 4H), 3.15–3.50 (m, 5H), 3.76(s, 3H), 4.20–4.60(m, 3H), 6.80–7.00(m, 3H), 7.05–7.30(m, 6H), 7.49(d, J=9 Hz, 3/5.1H), 7.62(d, J=9 Hz, 2/5.1H) | C₃₁H₄₄N₄O₃ | 71.51 71.50 | 8.52 8.25 | 10.76 10.51 |
| 149 | 3-benzo[b]thienyl-CH₂ | | foam | 576 (M⁺) | ¹H CDCl₃ 1.41–1.78(m, 9H), 2.00–2.21(m, 7H), 2.41–2.48(m, 4H), 2.59(d, J=11.4 Hz, 1H), 2.74(d, J=12.6 Hz, 1H), 2.88(s, 3H), 3.04(dd, J=4.3, 13.9 Hz, 1H), | C₃₃H₄₄N₄O₃S | 68.72 68.47 | 7.69 7.79 | 9.71 9.77 |

-continued 3.20(dd, J=6.1, 14.5 Hz, 1H), 3.70(s, 3H), 4.04(dd, J=10.5, 18.9 Hz, 1H), 4.40(ABq, J=16.5 Hz, Δv=46.1 Hz, 2H), 4.50(m, 1H), 6.73(m, 2H), 6.78(d, J=8.2 Hz, 1H), 7.13(s, 1H), 7.19(m, 1H), 7.27(m, 2H), 7.57(d, J=8.1 Hz, 1H), 7.84(d, J=7.5 Hz, 1H), 7.96 (d, J=7.6 Hz, 1H)

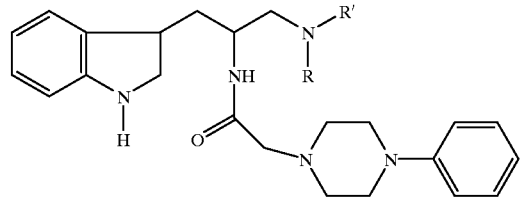

| Example No. | R | R' | Mp °C. | MS | ¹H NMR | Formula | Analysis % Theory/Found C | H | N |
|---|---|---|---|---|---|---|---|---|---|
| 150 | H | H | 144–145 | 391 (M⁺) | CDCl₃ 2.18–2.42(m, 2H), 2.42–2.77(m, 4H), 2.77–3.50(m, 10H), 4.43(m, 1H), 6.73–7.00(m, 3H), 7.07–7.59(m, 7H), 7.64(d, J=8 Hz, 1H), 8.24(br s, 1H) | $C_{23}H_{29}N_5O$ | 70.56 70.51 | 7.47 7.60 | 17.89 17.91 |
| 151 | t-Bu-O(CO) | H | 121–122 | 491 (M⁺) | CDCl₃ 1.63(s, 9H), 2.22–2.67(m, 4H), 2.75–3.23(m, 8H), 3.30(m, 1H), 3.40(m, 1H), 4.41(m, 1H), 5.03(m, 1H), 6.75–7.00(m, 4H), 7.07–7.70(m, 6H), 7.65(d, J=8 Hz, 1H), 8.18(br s, 1H) | $C_{28}H_{37}N_5O_3$ | 68.40 68.16 | 7.59 7.56 | 14.25 14.05 |
| 152 | PhCO | H | 188–189 | 495 (M⁺) | CDCl₃/DMSOd₆ 1.90–2.74(m, 6H), 2.74–3.40(m, 4H), 3.11(d, J=7 Hz, 2H), 3.58–3.82(m, 2H), 4.55(m, 1H), 6.63–6.96(m, 3H), 7.00–7.53(m, 10H), 7.68(d, J=8 Hz, 1H), 7.60–8.00(m, 3H), 9.28 (br s, 1H) | $C_{30}H_{33}N_5O_2$ | 72.70 72.46 | 6.71 6.71 | 14.13 13.84 |
| 153 | H | (c-hexyl)CH₂ | foam | 487 (M⁺) | CDCl₃ 0.73–1.41(m, 6H), 1.41–2.08(m, 8H), 2.10–3.38(m, 14H), 4.56(m, 1H), 6.81(d, J=8 Hz, 1H), 6.81–6.97(m, 4H), 7.02–7.40 (m, 4H), 7.57–7.73(m, 2H), 8.10 (br s, 1H) | $C_{30}H_{41}N_5O$ | 73.88 73.60 | 8.47 8.36 | 14.36 14.24 |

| Example No. | R | R' | Purification | Yield % | Mp °C. | MS | ¹H NMR | Formula | Analysis, % Theory/Found C | H | N |
|---|---|---|---|---|---|---|---|---|---|---|---|
| 154 | t-Bu-O(CO)NH—CH₂CO | (c-hexyl) CH₂ | chrom (EtOH/EtOAc) | 84 mg 43% | foam | 644 (M⁺) | CDCl₃ 0.75–1.00(m, 2H), 1.00–1.94(m, 10H), 1.44(s, 9H), 2.40–2.65(m, 3H), 2.65–3.66(m, 11H), 3.76–4.20(m, 3H), 4.60(m, 1H), 5.54(m, 1H), 6.75–7.05(m, 3H), 7.05–7.46(m, 7H), 7.67(d, J=8 Hz, 1H), 8.13(br s, 1H) | $C_{37}H_{52}N_6O_4$ | 68.92 68.93 | 8.13 8.28 | 13.03 13.11 |

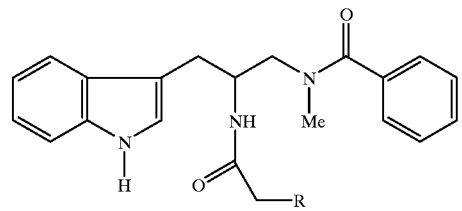

| Example No. | R | Mp °C. | MS | ¹H NMR | Formula | Analysis Theory/Found C | H | N |
|---|---|---|---|---|---|---|---|---|
| 155 | 1-(4-(1-piperidinyl)-piperidinyl | foam | 515 (M⁺) | CDCl₃ 1.3–2.1(m, 11H), 2.30(m, 1H), 2.4–3.3(m, 12H), 3.00(s, | $C_{31}H_{41}N_5O_2$ | 72.20 72.12 | 8.01 8.22 | 13.58 13.82 |

-continued

| | | | | 3H), 4.28(m, 1H), 4.74(m, 1H), 7.1–7.5(m, 10H), 7.68(d, J=8 Hz, 8.83(br s, 1H) | | | | |
|---|---|---|---|---|---|---|---|---|
| 156 | 1-(4-AcNH-4-Ph-piperidinyl) | 168–9 | 565 (M⁺) | CDCl₃ 1.97(s, 3H), 2.0–2.6(m, 8H), 2.8–3.3(m, 4H), 2.99(s, 3H), 3.52(m, 1H), 4.30(m, 1H), 4.72 (m, 1H), 5.48(m, 1H), 7.0–7.7(m, 15H), 7.68(m, 1H), 8.41(br s, 1H) | C₃₄H₃₉N₅O₃ | 72.19 72.47 | 6.95 7.08 | 12.38 12.63 |
| 157 | 1-(4-Ph-piperazinyl) | foam | 509 (M⁺) | CDCl₃ 2.3–2.7(m, 3H), 2.7–3.7(m, 10H), 8.02(s, 3H), 4.30(m, 1H), 4.78(m, 1H), 6.7–6.9(m, 3H), 7.1–7.5(m, 12H), 7.70(d, J=7 Hz, 1H), 8.22(br s, 1H) | C₃₁H₃₅N₅O₂ | 73.06 72.91 | 6.92 6.96 | 13.74 13.70 |
| 158 | 1-(4-cyclohexyl-piperazinyl) | foam | 515 (M⁺) | CDCl₃ 1.0–1.3(m, 6H), 1.6–2.0(m, 4H), 2.2–2.6(m, 9H), 2.9–3.2(m, 5H), 2.99(s, 3H), 4.38(m, 1H), 4.75(m, 1H), 7.1–7.5(m, 10H), 7.69(d, J=6 Hz, 1H), 8.23(br s, 1H) | C₃₁H₄₁N₅O₂ | 72.40 72.20 | 8.00 8.01 | 13.66 13.58 |

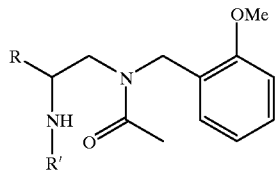

| | | | | | | Analysis Theory/Found | | |
|---|---|---|---|---|---|---|---|---|
| Example No. | R | R' | Mp °C. | MS | ¹H NMR | Formula | C | H | N |
| 159 | PhCH₂ | H | oil | 312 (M⁺) | CDCl₃ 3:1 mixture of amide rotamers 1.90–2.15(m, 2H), 2.17 (s, 3/4.3H), 2.23(s, 1/4.3H), 2.62 (dd, J=8, 13 Hz, 1H), 2.83(dd, J=5, 13 Hz, 1H), 3.26–3.55(m, 3H), 3.84(s, 3H), 4.55(d, J=14 Hz, 3/4.2H), 4.63(d, J=11 Hz, 1/4.2H), 6.80–7.03(m, 3H), 7.13–7.36(m, 6H) | C₁₉H₂₄N₂O₂ | 73.05 72.82 | 7.74 7.68 | 8.97 8.80 |
| 160 | 1-Me-3-indolyl-CH₂ | H | oil | 365 (M⁺) | CDCl₃ 2.00–2.30(m, 4H), 2.78 (dd, J=7, 15 Hz, 1H), 2.93(m, 1H), 3.30–3.60(m, 4H), 3.75(s, 3H), 3.82(s, 3H), 4.60(ABq, J=16 Hz, Δν=30, 2H), 6.83–7.00(m, 4H), 7.10(m, 1H), 7.16–7.33(m, 3H), 7.55(m, 1H) | C₂₂H₂₇N₃O₂ | 72.30 72.02 | 7.45 7.43 | 11.50 11.24 |
| 161 | Ph | BrCH₂CO | oil | 418, 420 (M⁺'s for Br isotopes) | CDCl₃ 2.22(s, 3H), 3.06(dd, J=3, 14 Hz, 1H), 3.83(s, 2H), 3.87(s, 3H), 4.26(dd, J=11, 15 Hz, 1H), 4.45(ABq, J=17 Hz, Δν=62 Hz, 2H), 4.93(m, 1H), 6.88–7.06(m, 3H), 7.23–7.36(m, 6H), 8.23(d, J=6 Hz, 1H) | C₂₀H₂₃BrN₂O₃ | 57.29 57.24 | 5.53 5.48 | 6.68 6.49 |
| 161a | PhCH₂ | BrCH₂CO | oil | 432, 434 (M⁺'s for Br isotopes) | CDCl₃ 2.17(s, 3H), 2.66(dd, J=8, 14 Hz, 1H), 2.84(dd, J=9, 14 Hz, 1H), 2.97(dd, J=5, 14 Hz, 1H), 3.73–3.85(m, 5H), 4.05(m, 1H), 4.18(m, 1H), 4.40(ABq, J=16 Hz, Δν=39 Hz, 2H), 6.79–6.90(m, 3H), 7.16–7.40(m, 7H) | C₂₁H₂₅BrN₂O₃ | 58.21 58.28 | 5.81 5.80 | 6.46 6.32 |
| 162 | 1-Me-3-indolylCH₂ | BrCH₂CO | foam | 485, 487 (M⁺'s for Br isotopes), | ¹H CDCl₃ 2.15(s, 3H), 2.90(dd, J=8, 14 Hz, 1H), 2.92(dd, J=6, 14 Hz, 1H), 3.10(dd, J=4, 14 Hz, 1H), 3.72(s, 3H), 3.74(s, 3H), 3.80(s, 2H), 4.07(m, 1H), 4.23–4.40(m, 2H), 4.46(m, 1H), 6.70–6.90(m, 4H), 7.13(d, J=8 Hz, 1H), 7.20–7.33(m, 3H), 7.33(d, J=12 Hz, 1H), 7.68(d, J=8 Hz, 1H). | C₂₄H₂₈BrN₃O₃ | 59.26 59.50 | 5.80 5.76 | 8.64 8.52 |

-continued

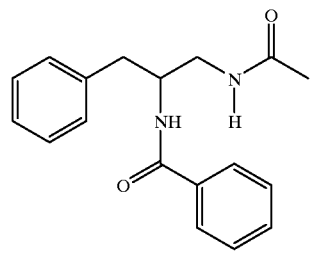

| Example No. | Mp, °C. | MS | ¹H NMR | Formula | Analysis, % Theory/Found C | H | N |
|---|---|---|---|---|---|---|---|
| 163 | 203–205 | 358 (M⁺) | CDCl₃ 2.89(dd, J=9, 14 Hz, 1H), 3.19(dd, J=6, 14 Hz, 1H), 3.54(dt, J=4, 14 Hz, 1H), 3.75(m, 1H), 4.54(m, 1H), 7.01(m, 1H), 7.15(m, 1H), 7.18–7.35(m, 4H), 7.35–7.55(m, 7H), 8.65–8.79(m, 4H) | $C_{23}H_{22}N_2O_2$ | 77.07 / 76.83 | 6.19 / 6.21 | 7.81 / 7.88 |

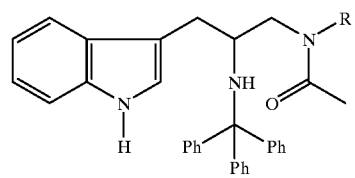

| Example No. | R | Mp °C. | MS | ¹H NMR | Formula | Analysis Theory/Found C | H | N |
|---|---|---|---|---|---|---|---|---|
| 164 | Me | 183–184 | 488 (M + 1⁺) | CDCl₃ 1.56(s, 3H), 1.90(m, 1H), 2.10(m, 1H), 2.35(m, 1H), 2.5–2.6(br s, 3H), 2.75 (m, 1H), 2.95(m, 1H), 3.20(m, 1H), 6.9–7.1(m, 2H), 7.1–7.6(m, 17H), 7.85(m, 1H), 7.96(br s, 1H) | $C_{33}H_{33}N_3O_3$ | 81.28 / 81.26 | 6.82 / 6.91 | 8.62 / 8.71 |
| 165 | n-Bu | foam | 530 (M + 1⁺) | ¹H CDCl₃ 0.51–0.81(m, 3H), 0.85–1.31 (m, 3H), 1.58(s, 1H), 1.88(s, 2H), 1.98 (s, 1H), 2.00–2.10(m, 1H), 2.40–2.78(m, 3H), 2.86–3.00(m, 2H), 3.20–3.40(m, 2H), 6.88(s, 1H), 6.89–7.08(m, 2H), 7.09–7.38 (m, 11H), 7.40–7.60(m, 5H), 7.80–8.00 (m, 2H). | $C_{36}H_{39}N_3O$ | 81.63 / 81.90 | 7.42 / 7.44 | 7.93 / 8.03 |
| 166 | n-Hex | foam | 558 (M + 1⁺) | ¹H CDCl₃ 0.80–0.88(m, 6H), 0.88–1.30 (m, 7H), 1.92(s, 2H), 1.98(s, 1H), 2.20–2.72(m, 3H), 2.85–3.02(m, 1H), 3.06–3.38 (m, 2H), 6.92(s, 1H), 6.97–7.06(m, 2H), 7.11–7.38((m, 12H), 7.38–7.58(m, 5H), 7.85–7.98(m, 1H) | $C_{38}H_{43}N_3O$ | 81.83 / 82.10 | 7.77 / 7.74 | 7.53 / 7.24 |
| 167 | Ph | 182–183 | 550 (M + 1⁺) | ¹H DMSO 1.64(s, 3H), 2.55(m, 1H), 2.59–2.82(m, 3H), 3.30(m, 1H), 3.63(dd, J=7, 14 Hz, 1H), 6.72(d, J=2 Hz, 1H), 6.74–6.82(m, 2H), 6.84(t, J=8 Hz, 1H), 6.99(t, J=8 Hz, 1H), 7.05–7.21(m, 10H), 7.21–7.64(m, 10H), 10.67(br s, 1H). | $C_{38}H_{35}N_3O$ | 83.03 / 82.80 | 6.42 / 6.65 | 7.64 / 7.39 |
| 168 | PhCH₂CH₂ | 174–175 | 577 (M⁺) | ¹H DMSO (3:2 mixture of amide rotamers) 1.77(s, 3/5.3H), 1.97(s, 2/5.3H), 2.06–2.44(m, 4H), 2.64–3.04(m, 4H), 3.18(m, 1H), 3.38–3.61(m, 1H), 6.61–6.71(m, 2H), 6.88(m, 1H), 6.96–7.08 (m, 2H), 7.08–7.34(m, 14H), 7.41–7.56 (m, 6H), 10.78(br s, 1H). | $C_{40}H_{39}N_3O$ | 83.15 / 82.92 | 6.80 / 6.83 | 7.27 / 7.57 |

-continued

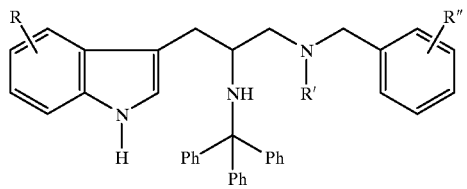

| Example No. | R | R' | R'' | Mp, ° C. | MS | ¹H NMR | Formula | Analysis, % Theory/Found C | H | N |
|---|---|---|---|---|---|---|---|---|---|---|
| 169 | 6-Me | H | 2-OMe | oil | 566 (M + 1⁺) | CDCl₃ 1.90(m, 1H), 2.18–2.33(m, 2H), 2.44(s, 3H), 2.60(m, 1H), 2.68–2.96(m, 2H), 3.48–3.68(m, 3H), 3.80(s, 3H), 6.86(d, J=8 Hz, 3H), 6.99–7.46(m, 15H), 7.46–7.73(m, 5H), 7.76(s, 1H) | C₃₉H₃₉N₃O | 82.80 / 82.81 | 6.95 / 7.02 | 7.43 / 7.32 |
| 170 | H | MeCO | 2-Cl | foam | 598 (M + 1) | CDCl₃ 3:2 mixture of amide rotamers 1.80(s, 3/5.3H), 2.05(s, 2/5.3H), 2.30–2.53(m, 2H), 2.65(m, 1H), 3.00–3.33(m, 3H), 3.91(ABq, J=20 Hz, Δν=30 Hz, 3/5.2H), 4.61(ABq, J=18 Hz, Δν=77 Hz, 2/5.2H), 6.58–6.67(m, 3/5.1H), 6.80–6.89(m, 2/5.1H), 6.94–7.33(m, 18H), 7.42–7.56(m, 5H), 7.86(br s, 1H) | C₃₉H₃₆ClN₃O | 78.37 / 78.10 | 6.07 / 6.25 | 7.02 / 6.78 |
| 171 | 6-Me | MeCO | 2-OMe | oil | 608 (M + 1⁺) | CDCl₃ 3:1 mixture of amide rotamers 1.92(s, 3/4.3H), 1.97(s, 1/4.3H), 2.44(s, 3H), 2.56–2.76(m, 2H), 3.04–3.36(m, 4H), 3.62(s, 1H), 3.72(s, 3H), 4.03(d, J=18 Hz, 1H), 6.43(d, J=9 Hz, 1H), 6.58–7.00(m, 4H), 7.00–7.28(m, 11H), 7.40–7.60(m, 7H), 7.74(br s, 1H) | C₄₁H₄₁N₃O₂ | 81.02 / 80.90 | 6.80 / 6.66 | 6.91 / 7.16 |

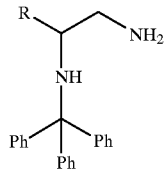

| Example No. | R | Mp, ° C. | MS | ¹H NMR | Formula | Analysis, % Theory/Found C | H | N |
|---|---|---|---|---|---|---|---|---|
| 172 | 3,4-diCl-Ph | oil | 447 (M + 1⁺) | ¹H CDCl₃ 1.56–1.95(m, 2H), 2.04 (dd, J=6, 13 Hz, 1H), 2.52(dd, J= 4, 12 Hz, 1H), 2.90(m, 1H), 3.67 (m, 1H), 7.03(m, 1H), 7.06–7.36 (m, 12H), 7.40–7.55(m, 5H). | C₂₇H₂₄Cl₂N₂ | 72.48 / 72.45 | 5.41 / 5.38 | 6.26 / 6.02 |

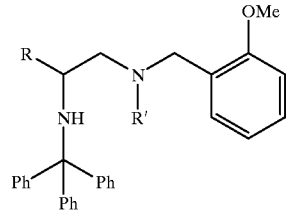

| Example No. | R | R' | Mp ° C. | MS | ¹H NMR | Formula | Analysis Theory/Found C | H | N |
|---|---|---|---|---|---|---|---|---|---|
| 173 | Ph | H | oil | 499 (M + 1⁺) | CDCl₃ 2.25–2.36(m, 2H), 3.06(m, 1H), 3.40–3.50(m, 2H), 3.54(s, 3H), 3.75–3.90 (m, 2H), 6.74(d, J=8 Hz, 1H), 6.85(m, 1H), 6.98(m, 3H), 7.03–7.40(m, 15H), 7.45–7.60(m, 6H) | C₃₅H₃₄N₂O | 84.30 / 84.47 | 6.87 / 6.87 | 5.62 / 5.74 |
| 174 | PhCH₂ | H | oil | 513 (M + 1⁺) | CDCl₃ 1.93–2.10(m, 2H), 2.20(m, 1H), 2.23–2.40(m, 2H), 2.60(m, 1H), 2.75(m, 1H), 3.55–3.65(m, 2H), 3.82(s, 3H), 6.83– | C₃₆H₃₆N₂O | 84.34 / 84.41 | 7.08 / 6.95 | 5.46 / 5.76 |

-continued

| | | | | | | | | | |
|---|---|---|---|---|---|---|---|---|---|
| | | | | | 6.98(m, 4H), 7.03–7.40(m, 14H), 7.53–7.66(m, 6H) | | | | |
| 175 | Ph | MeCO | foam | 540 (M$^+$) | CDCl$_3$ 2:1 mixture of amide rotamers 1.9 (s, 2/3.3H), 1.96(s, 1/3.3H), 2.93(m, 1H), 3.05(m, 1H), 3.67(s, 2/3.3H), 3.75 (s, 1/3.3H), 3.75(m, 1H), 3.93(d, J=18 Hz, 2H), 4.21(ABq J=14 Hz, Δv=21 Hz, 1H), 6.66–6.90(m, 3H), 6.90–7.35(m, 15H), 7.35–7.55(m, 6H) | C$_{37}$H$_{36}$N$_2$O$_2$ | 82.19 82.37 | 6.71 6.69 | 5.18 5.03 |
| 176 | 3,4-diCl-Ph | MeCO | 181–182.5 | 608 (M$^+$ for Cl isotope), Exact M.S. Theory: 609.2075, Found: 609.2053 | $^1$H CDCl$_3$ 1.99(s, 3H), 2.96(dd, J=6, 14 Hz, 1H), 3.12(m, 1H), 3.60(dd, J=8, 14 Hz 1H), 3.81(s, 3H), 3.90–4.16(m, 8H), 6.73–6.96(m, 4H), 6.96–7.30(m, 12H), 7.30–7.49(m, 6H) | C$_{37}$H$_{34}$Cl$_2$N$_2$O$_2$ | 72.90 73.56 | 5.62 5.70 | 4.59 4.66 |
| 177 | PhCH$_2$ | MeCO | foam | 554 (M$^+$) | CDCl$_3$ 2:1 mixture of amide rotamers 1.90(s, 2/3.3H), 1.95(s, 1/3.3H), 2.36–2.53(m, 2H), 2.63(dd, J=4, 18 Hz, 1H), 3.00(m, 1H), 3.06–3.23(m, 2H), 3.66(s, 1/3.3H), 3.76(s, 2/3.3H), 3.85(ABq, J=17 Hz, Δv=110 Hz, 2/3.2H), 4.59(Al3q, J=17 Hz, Δv=100 Hz, 1/3.2H), 6.42(d, J=7 Hz, 1H), 6.68–6.85(m, 3H), 6.92–7.05 (m, 2H), 7.05–7.43(m, 12H), 7.50–7.63 (m, 6H) | C$_{38}$H$_{38}$N$_2$O$_2$ | 82.28 82.01 | 6.90 6.96 | 5.05 5.25 |

The compounds of formula I are potent effective inhibitors of neutrophil mediated oxidant production. As such, they are useful in treating conditions associated with excessive or unregulated neutrophil accumulation, such as, but not limited to, the following: smoking, chronic bronchitis, emphysema, asthma, cystic fibrosis, cancer, adult respiratory distress syndrome, Wegener's granulomatosis, idiopathic pulmonary fibrosis, collagen vascular disorders, interstitial lung disease, hypersensitivity pneumonitis: sarcoidosis, bronchiolitis obliterans with organizing pneumonia, Crohn's Disease, Secondary Sjörgren's Syndrome, rheumatoid arthritis, progressive systemic sclerosis, dermatopolymyositis, mixed connective tissue disease, familial idiopathic pulmonary fibrosis, systemic lupus erythematosus, progressive systemic sclerosis, autoimmune thyroid disease, inflammatory bowel disease, juvenile periodontitis, myocardial infarction, hemorrhagic schock, septic shock, ischemic shock, cerebral ischemia, stroke, hypertension, unstable angina, diabetes complications, thrombotic stroke, fibrosing alveolitis, bronchiectasis, periodontal disease, glomerulonephritis, alcoholic hepatitis, Kawasaki Disease, gingivitis, chronic obstructive pulmonary disease, pulmonary infections (staphylococcal or klebsiella pneumonia), ulcerative colitis, psoriasis, artherosclerosis, gout, gastroesophageal reflux disease, carditis, Barrett's Esophagus, Behcet's Disease, iritis, acute glomerulonephritis, periarteritis nodosa, unstable angina, coronary artery disease, coronary angioplasty, immune complex disease, cryoglobulinemic glomerulonephritis, anti-gbm glomerulonephritis, Goodpasture's Syndrome, myositis, and acute pancreatitis.

It is known that excess accumulation of neutrophils may lead to release of toxic oxygen radicals that potentiate tissue damage. Accordingly, representative compounds of the formula I were evaluated and found to effectively inhibit adhesion dependent oxidant production in the Inhibition of Adhesion-Dependent Oxidant Production test system described below.

Isolation of Human Neutrophils

Venous blood was drawn from healthy donors into citrate-phosphate dextrose anti-coagulant. Five ml of the collected blood were mixed with 1.5 ml 6% dextran in 0.87% NaCl solution (Macrodex®) and incubated at 37° C. for 25–35 minutes until the erythrocytes agglutinated and settled to the bottom of the tube. The supernatant fluid was removed and centrifuged at room temperature for 5 minutes at 300 g. The resulting cell pellet was resuspended in a volume of Dulbeccol's phosphate buffered saline (PBS) containing 0.2% glucose that was equal to the original blood volume. In 10 ml portions, the suspension was layered over 5 ml of Ficoll-Paque® and centrifuged at room temperature for 20 minutes at 675 g. All of the supernatant fluid and the resulting mononuclear cell layer were carefully removed and discarded. The pellet was resuspended as above, the cell density determined with a Cell-Dyne 1600 and the suspension centrifuged at 300 g for 5 minutes. The differential white blood cell (WBC) count was >90% granulocytes. After discarding the supernatant fluid, the cell pellet was resuspended as above at 1 million granulocytes/ml and used promptly in the assay.

Inhibition of Adhesion-Denendent Oxidant Production

Compounds were evaluated for their ability to inhibit hydrogen peroxide produced by neutrophils after the cells had been stimulated with formyl-L-methionyl-L-leucyl-L-phenylalanine (fMLP) to adhere and spread on a keyhole limpet hemocyanin (KLH)-coated surface. The amount of peroxide produced was measured by reacting it enzymatically with the fluorescent substrate, scopoletin. The reaction was carried out in 96-well plates using a protocol very similar to that reported by Shappell et al., *J. Immunol.*, 144, 2702–2711 (1990). Tissue culture plates (Linbro/ICN Flow) were prepared by filling each well with 250 µl of a filtered solution of 0.5 mg/ml KLH in carbonate-bicarbonate buffer containing 0.02% sodium azide. Plates were tightly sealed, incubated at 37° C. for 2–18 hours and then stored at 4° C. for up to 6 weeks. Just prior to being used, plates were washed twice with 250 µl Dulbecco's PBS per well and patted dry. All reagents were dissolved in a Krebs-Ringer-Phosphate (KRP) buffer containing 0.1% glucose, pH 7.35, 145 mM NaCl, 4.86 mM KCl, 0.54 mM CaCl$_2$, 1.22 mM MgSO$_4$, and 5.77 mM Na$_2$HPO$_4$. Compounds were initially dissolved in dimethyl sulfoxide (DMSO) at 50 mM and stored at 4° C. until used. Appropriate dilutions were made with the KRP buffer to yield working solutions containing 0.2% DMSO. To start the reaction, wells were initially filled with 100 μl of buffer containing 0.2% DMSO or appropriate stock inhibitor solution. Next, 25 μl of fluorescent indicator mixture containing 5.6 mM sodium azide, 136 μM scopoletin and 28.8 μg/ml of horseradish peroxidase was added to each well. Then 25 μl of 240 nM fMLP in PBS was dispensed into the wells. The reaction was started by adding 50 μl of cell suspension (1×10$^6$ cells per ml). All experiments were carried out at 37° C. Spontaneous oxidation of scopoletin was monitored by observing the loss of fluorescence in wells to which no cells had been added. Fluorescence readings were made with either a Millipore Cytofluor 2350 or PerSeptive Biosystems Cytofluor II using an excitation wavelength of 360 nm and an emission wavelength of 460 nm. Inhibition concentration studies were carried out by testing five, 3-fold dilutions of each compound. After a lag period of 15–30 minutes, cells stimulated in the absence of any inhibitor began to produce H$_2$O$_2$ and the fluorescence decreased rapidly for the next 30–45 minutes. The time points that bracketed the steepest drop in fluorescence of these positive control wells were used to determine the extent of reaction in all wells. The fluorescence decrease (f.d.) during this time period at all compound concentrations was measured and the percent inhibition determined with the following formula:

$$100 \times \frac{(\text{f.d. of positive control} - \text{f.d. of compound-treated cells})}{(\text{f.d. of positive control} - \text{f.d. of no cells control})}$$

The IC$_{50}$ value was calculated assuming a linear relationship between percent inhibition and compound concentration in the region between 25% and 75% inhibition.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The active compound is effective over a wide dosage range. For example, dosages per day normally fall within the range of about 0.5 to about 30 mg/kg of body weight. In the treatment of adult humans, the range of about 1 to about 15 mg/kg/day, in single or divided doses, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A method for the treatment of gout, which method comprises administering to a mammal in need of said treatment an effective amount of a compound of the formula I

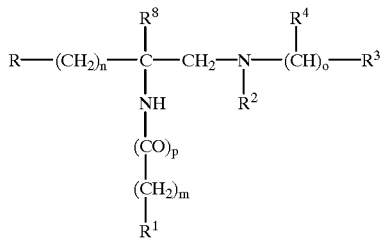

wherein
m is 0 or 1;
n is 0 or 1;
o is 0, 1, or 2;
p is 0 or 1;
R is phenyl, 2- or 3-indolyl, 2- or 3-indolinyl, benzothienyl, benzofuranyl, or naphthyl;
  any one of which groups may be substituted with one or two halo, C$_1$–C$_3$ alkoxy, trifluoromethyl, C$_1$–C$_4$ alkyl, phenyl-C$_1$–C$_3$ alkoxy, or C$_1$–C$_4$ alkanoyl groups;
R$^1$ is trityl, phenyl, diphenylmethyl, phenoxy, phenylthio, piperazinyl, hexamethyleneiminyl, piperidinyl, pyrrolidinyl, morpholinyl, indolinyl, indolyl, benzothienyl, benzofuranyl, quinolinyl, isoquinolinyl, tetrahydropyridinyl, reduced quinolinyl, reduced isoquinolinyl, phenyl-(C$_1$–C$_4$ alkyl)-, phenyl-(C$_1$–C$_4$ alkoxy)-, quinolinyl-(C$_1$–C$_4$ alkyl)-, isoquinolinyl-(C$_1$–C$_4$ alkyl)-, reduced quinolinyl-(C$_1$–C$_4$ alkyl)-, reduced isoquinolinyl-(C$_1$–C$_4$ alkyl)-, benzoyl-(C$_1$–C$_3$ alkyl)-, C$_1$–C$_4$ alkyl, or —NH—CH$_2$–R$^5$;
  any one of which R$^1$ groups may be substituted with halo, C$_1$–C$_4$ alkyl, C$_1$–C$_4$ alkoxy, trifluoromethyl, amino, C$_1$–C$_4$ alkylamino, or di(C$_1$–C$_4$ alkyl) amino;
  or any one of which R$^1$ groups may be substituted with phenyl, piperazinyl, C$_3$–C$_8$ cycloalkyl, benzyl, C$_1$–C$_4$ alkyl, piperidinyl, pyridinyl, pyrimidinyl, C$_2$–C$_6$ alkanoylamino, pyrrolidinyl, C$_2$–C$_6$ alkanoyl, or C$_1$–C$_4$ alkoxycarbonyl;
    any one of which groups may be substituted with halo, C$_1$–C$_4$ alkyl, C$_1$–C$_4$ alkoxy, trifluoromethyl, amino, C$_1$–C$_4$ alkylamino, di(C$_1$–C$_4$ alkyl)amino, or C$_2$–C$_4$ alkanoylamino;
or R$^1$ is amino, a leaving group, hydrogen, C$_1$–C$_4$ alkylamino, or di(C$_1$–C$_4$ alkyl)amino;
R$^5$ is pyridyl, anilino-(C$_1$–C$_3$ alkyl)-, or anilinocarbonyl;
R$^2$ is hydrogen, C$_1$–C$_4$ alkyl, arylsulfonyl, C$_1$–C$_4$ alkylsulfonyl, carboxy-(C$_1$–C$_3$ alkyl)-, C$_1$–C$_3$ alkoxycarbonyl-(C$_1$–C$_3$ alkyl)-, or —CO—R$^6$;
R$^6$ is hydrogen, C$_1$–C$_4$ alkyl, C$_1$–C$_3$ haloalkyl, phenyl, C$_1$–C$_3$ alkoxy, C$_1$–C$_3$ hydroxyalkyl, amino, C$_1$–C$_4$ alkylamino, di(C$_1$–C$_4$ alkyl)amino, or —(CH$_2$)$_q$—R$^7$;
q is 0 to 3;
R$^7$ is phenoxy, phenylthio, piperazinyl, piperidinyl, pyrrolidinyl, morpholinyl, indolinyl, indolyl, benzothienyl, benzofuranyl, quinolinyl, isoquinolinyl, reduced quinolinyl, reduced isoquinolinyl, phenyl-(C$_1$–C$_4$ alkyl)-, quinolinyl-(C$_1$–C$_4$ alkyl)-, isoquinolinyl-($C_1$–$C_4$ alkyl)-, reduced quinolinyl-($C_1$–$C_4$ alkyl)-, reduced isoquinolinyl-($C_1$–$C_4$ alkyl)-, benzoyl-$C_1$–$C_3$ alkyl;

any one of which $R^7$ groups may be substituted with halo, trifluoromethyl, $C_1$–$C_4$ alkoxy, amino, $C_1$–$C_4$ alkylamino, di($C_1$–$C_4$ alkyl)amino, or $C_2$–$C_4$ alkanoylamino;

or any one of which $R^7$ groups may be substituted with phenyl, piperazinyl, $C_3$–$C_8$ cycloalkyl, benzyl, piperidinyl, pyridinyl, pyrimidinyl, pyrrolidinyl, $C_2$–$C_6$ alkanoyl, $C_1$–$C_4$ alkyl, or $C_1$–$C_4$ alkoxycarbonyl;

any of which groups may be substituted with halo, trifluoromethyl, amino, $C_1$–$C_4$ alkoxy, $C_1$–$C_4$ alkyl, $C_1$–$C_4$ alkylamino, di($C_1$–$C_4$ alkyl)amino, or $C_2$–$C_4$ alkanoylamino;

or $R^7$ is carboxy, $C_1$–$C_4$ alkoxycarbonyl, $C_1$–$C_4$ alkylcarbonyloxy, amino, $C_1$–$C_4$ alkylamino, di($C_1$–$C_4$ alkyl)amino, $C_1$–$C_6$ alkoxycarbonylamino;

$R^8$ is hydrogen or $C_1$–$C_6$ alkyl;

$R^3$ is phenyl, phenyl-($C_1$–$C_6$ alkyl)-, $C_3$–$C_8$ cycloalkyl, $C_5$–$C_8$ cycloalkenyl, $C_1$–$C_8$ alkyl, naphthyl, $C_2$–$C_8$ alkenyl, or hydrogen;

any one of which groups except hydrogen may be substituted with one or two halo, $C_1$–$C_3$ alkoxy, $C_1$–$C_3$ alkylthio, nitro, trifluoromethyl, or $C_1$–$C_3$ alkyl groups;

and $R^4$ is hydrogen or $C_1$–$C_3$ alkyl;

with the proviso that if $R^1$ is hydrogen or halo, $R^3$ is phenyl, phenyl-($C_1$–$C_6$ alkyl)-, $C_3$–$C_8$ cycloalkyl, $C_5$–$C_8$ cycloalkenyl, or naphthyl;

or a pharmaceutically acceptable salt or solvate thereof.

2. The method as claimed in claim 1 employing a compound wherein R is phenyl, naphthyl, or 2- or 3-indolyl which group may be optionally substituted.

3. The method as claimed in claim 2 employing a compound wherein n is 1.

4. The method as claimed in claim 3 employing a compound wherein $R^2$ is —CO—$R^6$, arylsulfonyl, or $C_1$–$C_4$ alkylsulfonyl.

5. The method as claimed in claim 4 employing a compound wherein $R^2$ is acetyl or methylsulfonyl.

6. The method as claimed in claim 5 employing a compound of the formula

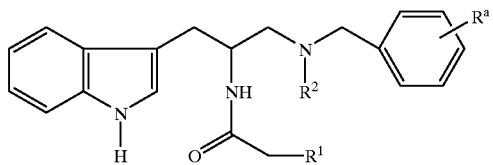

wherein $R^a$ is halo, $C_1$–$C_3$ alkoxy, $C_1$–$C_3$ alkylthio, nitro, trifluoromethyl, or $C_1$–$C_3$ alkyl.

7. The method as claimed in claim 6 employing a compound wherein $R^a$ is $C_1$–$C_3$ alkoxy, chloro, fluoro, trifluoromethyl or $C_1$–$C_3$ alkylthio.

8. The method as claimed in claim 7 employing a compound wherein $R^a$ is methoxy, ethoxy, chloro, trifluoromethyl, or methylthio.

9. The method as claimed in claim 8 employing a compound wherein $R^1$ is piperazinyl, piperidinyl, substituted piperazinyl, or substituted piperidinyl.

10. The method as claimed in claim 9 employing a compound wherein $R^1$ is 1-(4-phenyl)piperazinyl.

11. The method as claimed in claim 9 employing a compound wherein $R^1$ is 1-(4-cyclohexyl)piperazinyl.

12. The method as claimed in claim 9 employing a compound wherein $R^1$ is 1-(4-phenyl)piperidinyl.

13. The method as claimed in claim 9 employing a compound wherein $R^1$ is 1-(4-cyclohexyl)piperidinyl.

14. The method as claimed in claim 9 employing a compound wherein $R^1$ is 1-(4-isopropyl)piperazinyl.

15. The method as claimed in claim 9 employing a compound wherein $R^1$ is 1-[4-(1-piperidinyl)]piperidinyl.

* * * * *